United States Patent
Huch Ortega et al.

(10) Patent No.: US 11,034,935 B2
(45) Date of Patent: Jun. 15, 2021

(54) LIVER ORGANOID, USES THEREOF AND CULTURE METHOD FOR OBTAINING THEM

(71) Applicant: Koninklijke Nederlandse Akademie van Wetenschappen, Utrecht (NL)

(72) Inventors: Meritxell Huch Ortega, Utrecht (NL); Johannes Carolus Clevers, Huis Ter Heide (NL)

(73) Assignee: Koninklijke Nederlandse Akademie van Wetenschappen, Utrecht (NL)

( * ) Notice: Subject to any disclaimer, the term of this patent is extended or adjusted under 35 U.S.C. 154(b) by 0 days.

(21) Appl. No.: 15/665,363

(22) Filed: Jul. 31, 2017

(65) Prior Publication Data

US 2018/0066233 A1    Mar. 8, 2018

Related U.S. Application Data

(63) Continuation of application No. 13/812,614, filed as application No. PCT/IB2011/002167 on Jul. 29, 2011, now Pat. No. 9,765,301.

(60) Provisional application No. 61/520,569, filed on Jun. 10, 2011, provisional application No. 61/368,736, filed on Jul. 29, 2010.

(30) Foreign Application Priority Data

Jul. 29, 2010 (EP) ..................... 10171265

(51) Int. Cl.
*C12N 5/071*     (2010.01)
*A61K 35/407*    (2015.01)

(52) U.S. Cl.
CPC .......... *C12N 5/0671* (2013.01); *A61K 35/407* (2013.01); *C12N 5/0672* (2013.01); *C12N 2500/38* (2013.01); *C12N 2501/11* (2013.01); *C12N 2501/119* (2013.01); *C12N 2501/12* (2013.01); *C12N 2501/155* (2013.01); *C12N 2501/415* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 5,464,758 A | 11/1995 | Gossen et al. | |
| 5,981,483 A | 11/1999 | Dennis et al. | |
| 6,165,782 A | 12/2000 | Naldini et al. | |
| 6,207,455 B1 | 3/2001 | Chang | |
| 6,218,181 B1 | 4/2001 | Verma et al. | |
| 6,277,633 B1 | 8/2001 | Olsen | |
| 6,323,031 B1 | 11/2001 | Cichutek | |
| 6,432,705 B1 | 8/2002 | Yee et al. | |
| 6,743,626 B2 | 6/2004 | Baum et al. | |
| 7,056,685 B1 | 6/2006 | Chen et al. | |
| 7,411,052 B2 | 8/2008 | Tang | |
| 7,439,927 B2 | 10/2008 | Lenart et al. | |
| 7,541,431 B2 | 6/2009 | Yoon | |
| 8,642,339 B2 | 2/2014 | Clevers et al. | |
| 8,685,726 B2 | 4/2014 | Schulz et al. | |
| 8,906,631 B2 | 12/2014 | Clevers et al. | |
| 9,752,124 B2 | 9/2017 | Sato et al. | |
| 9,765,301 B2 | 9/2017 | Ortega et al. | |
| 9,833,496 B2 | 12/2017 | Clevers et al. | |
| 10,006,904 B2 | 6/2018 | Beekman et al. | |
| 10,597,633 B2 | 3/2020 | Huch Ortega et al. | |
| 2003/0003088 A1 | 1/2003 | Tsao et al. | |
| 2003/0032034 A1 | 2/2003 | Tang | |
| 2003/0129751 A1 | 7/2003 | Grikscheit et al. | |
| 2003/0138951 A1* | 7/2003 | Yin ...................... | C12N 5/0676 435/370 |
| 2004/0175367 A1 | 9/2004 | Herlyn et al. | |
| 2004/0191902 A1 | 9/2004 | Hambor et al. | |
| 2004/0229355 A1 | 11/2004 | Chen et al. | |
| 2005/0054829 A1 | 3/2005 | Wiley et al. | |
| 2005/0058687 A1 | 3/2005 | Guarino et al. | |
| 2005/0265980 A1 | 12/2005 | Chen et al. | |
| 2006/0182724 A1 | 8/2006 | Riordan | |
| 2007/0010008 A1 | 1/2007 | Tseng et al. | |
| 2007/0020637 A1 | 1/2007 | Isogai et al. | |
| 2007/0036769 A9 | 2/2007 | Li et al. | |
| 2007/0122903 A1 | 5/2007 | Rezania et al. | |
| 2007/0244061 A1 | 10/2007 | Niehrs et al. | |
| 2007/0254359 A1 | 11/2007 | Rezania et al. | |
| 2008/0112890 A1 | 5/2008 | Lelkes et al. | |
| 2008/0113433 A1 | 5/2008 | Robins et al. | |
| 2008/0166327 A1 | 7/2008 | Asahara et al. | |
| 2008/0182328 A1 | 7/2008 | Snyder et al. | |
| 2008/0233088 A1 | 9/2008 | Guha et al. | |
| 2008/0242594 A1 | 10/2008 | McKay et al. | |

(Continued)

FOREIGN PATENT DOCUMENTS

| | | |
|---|---|---|
| EA | 7611 B1 | 12/2006 |
| EP | 0953633 A1 | 11/1999 |

(Continued)

OTHER PUBLICATIONS

Sarkozi et al., Am J Physiol Renal Physiol, 2011, vol. 301: F1014-F1025.*
Tanimizu et al., Journal of Cell Science, vol. 117 (15), 2004.*
Tojo et al., Cancer Sci, 2005, vol. 96, No. 11, pp. 791-800.*
Crawford et al., Developmental Dynamics, vol. 236: 886-892, 2007.*
U.S. Appl. No. 16/113,445, filed Aug. 27, 2018, Pending.
U.S. Appl. No. 14/111,091, filed Oct. 31, 2013, Abandoned, 2014-0044713.
U.S. Appl. No. 14/124,884, filed May 9, 2014, Published, 2014-0243227.

(Continued)

*Primary Examiner* — Scott Long
*Assistant Examiner* — Evelyn Y Pyla
(74) *Attorney, Agent, or Firm* — Wolf, Greenfield & Sacks, P.C.

(57) ABSTRACT

The invention relates to a liver organoid, uses thereof and method for obtaining them.

19 Claims, 36 Drawing Sheets

Specification includes a Sequence Listing.

(56) References Cited

U.S. PATENT DOCUMENTS

| | | |
|---|---|---|
| 2009/0275067 A1 | 11/2009 | Taniguchi et al. |
| 2009/0311748 A1 | 12/2009 | Isogai et al. |
| 2009/0325289 A1 | 12/2009 | Hatzfeld |
| 2010/0047853 A1 | 2/2010 | Kuo et al. |
| 2010/0071078 A1 | 3/2010 | Niehrs |
| 2010/0137210 A1 | 6/2010 | Funk et al. |
| 2010/0166713 A1 | 7/2010 | Dalton et al. |
| 2010/0247648 A1 | 9/2010 | Grubb et al. |
| 2010/0275280 A1 | 10/2010 | Clevers et al. |
| 2010/0278800 A1 | 11/2010 | Boyle et al. |
| 2011/0002897 A1 | 1/2011 | Snyder et al. |
| 2011/0191868 A1 | 8/2011 | Gupta |
| 2012/0028355 A1 | 2/2012 | Sato et al. |
| 2012/0196312 A1 | 8/2012 | Sato et al. |
| 2012/0207744 A1 | 8/2012 | Mendlein et al. |
| 2013/0005737 A1 | 1/2013 | Prabhu et al. |
| 2013/0052729 A1 | 2/2013 | Pourquie et al. |
| 2013/0089562 A1 | 4/2013 | French et al. |
| 2013/0189327 A1 | 7/2013 | Ortega et al. |
| 2013/0280809 A1 | 10/2013 | Efe et al. |
| 2014/0044713 A1 | 2/2014 | De Lau et al. |
| 2014/0243227 A1 | 8/2014 | Clevers et al. |
| 2014/0256037 A1 | 9/2014 | Sato et al. |
| 2015/0011420 A1 | 1/2015 | Beekman et al. |
| 2015/0231201 A1 | 8/2015 | Clevers et al. |
| 2017/0151308 A9 | 6/2017 | Clevers et al. |
| 2017/0191030 A1 | 7/2017 | Huch Ortega et al. |
| 2017/0275592 A1 | 9/2017 | Sachs et al. |
| 2017/0342385 A1 | 11/2017 | Sachs et al. |
| 2018/0072995 A1 | 3/2018 | Sato et al. |
| 2018/0221441 A1 | 8/2018 | Clevers et al. |
| 2019/0100728 A1 | 4/2019 | Sato et al. |
| 2019/0383799 A1 | 12/2019 | Beekman et al. |
| 2019/0390171 A1 | 12/2019 | Sato et al. |

FOREIGN PATENT DOCUMENTS

| | | |
|---|---|---|
| EP | 1347046 A1 | 9/2003 |
| EP | 1440981 A2 | 7/2004 |
| EP | 1792979 A1 | 6/2007 |
| EP | 2157192 A1 | 2/2010 |
| EP | 1673475 B1 | 4/2010 |
| EP | 2228443 A1 | 9/2010 |
| EP | 2412800 A1 | 2/2012 |
| EP | 1427747 B1 | 4/2012 |
| EP | 1727560 B1 | 9/2012 |
| EP | 2772534 A1 | 9/2014 |
| JP | 2002-247978 A | 9/2002 |
| JP | 2006-325444 A | 12/2006 |
| JP | 2007-504823 A | 3/2007 |
| JP | 2007-116926 A | 5/2007 |
| JP | 2008-061569 A | 3/2008 |
| JP | 2009-520474 A | 5/2009 |
| JP | 2013-521247 | 9/2015 |
| RU | 2323252 C1 | 4/2008 |
| RU | 2465323 C2 | 10/2012 |
| WO | WO 97/34999 A1 | 9/1997 |
| WO | WO 01/23528 A1 | 4/2001 |
| WO | WO 01/077169 A2 | 10/2001 |
| WO | WO 02/18544 A2 | 3/2002 |
| WO | WO 03/029405 A2 | 4/2003 |
| WO | WO 03/029437 A2 | 4/2003 |
| WO | WO 03/054152 A2 | 7/2003 |
| WO | WO 03/055911 A2 | 7/2003 |
| WO | WO 2004/050827 A2 | 6/2004 |
| WO | WO 2004/087896 A2 | 10/2004 |
| WO | WO 2005/034625 A1 | 4/2005 |
| WO | WO 2005/040391 A1 | 5/2005 |
| WO | WO 2005/040418 A2 | 5/2005 |
| WO | WO 2005/072419 A2 | 8/2005 |
| WO | WO 2005/110009 A2 | 11/2005 |
| WO | WO 2005/117994 A2 | 12/2005 |
| WO | WO 2006/104536 A2 | 10/2006 |
| WO | WO 2007/013666 A2 | 2/2007 |
| WO | WO 2007/030290 A2 | 3/2007 |
| WO | WO 2007/050043 A2 | 5/2007 |
| WO | WO 2007/071339 A1 | 6/2007 |
| WO | WO 2007/100357 A2 | 9/2007 |
| WO | WO 2007/127454 A2 | 11/2007 |
| WO | WO 2007/127927 A2 | 11/2007 |
| WO | WO 2007/149182 A2 | 12/2007 |
| WO | WO 2008/020942 A2 | 2/2008 |
| WO | WO 2008/046649 A1 | 4/2008 |
| WO | WO 2008/075796 A1 | 6/2008 |
| WO | WO 2008/088524 A2 | 7/2008 |
| WO | WO 2008/101215 A1 | 8/2008 |
| WO | WO 2008/120218 A2 | 10/2008 |
| WO | WO 2008/155120 A2 | 12/2008 |
| WO | WO 2009/005809 A2 | 1/2009 |
| WO | WO 2009/012428 A2 | 1/2009 |
| WO | WO 2009/022907 A2 | 2/2009 |
| WO | WO 2010/011352 A2 | 1/2010 |
| WO | WO 2010/016766 A2 | 2/2010 |
| WO | WO 2010/049752 A1 | 5/2010 |
| WO | WO 2010/077681 A1 | 7/2010 |
| WO | WO 2010/077955 A1 | 7/2010 |
| WO | WO 2010/090513 A2 | 8/2010 |
| WO | WO 2010/108001 A2 | 9/2010 |
| WO | WO 2010/121923 A1 | 10/2010 |
| WO | WO 2010/129294 A3 | 4/2011 |
| WO | WO 2012/014076 A2 | 2/2012 |
| WO | WO 2012/044992 A2 | 4/2012 |
| WO | WO 2012/087965 A2 | 6/2012 |
| WO | WO 2012/140274 A2 | 10/2012 |
| WO | WO 2012/168930 A1 | 12/2012 |
| WO | WO 2013/054112 A1 | 4/2013 |
| WO | WO 2013/061608 A1 | 5/2013 |
| WO | WO 2013/093812 A2 | 6/2013 |
| WO | WO 2014/066649 A1 | 5/2014 |
| WO | WO 2014/124527 A1 | 8/2014 |
| WO | WO 2014/127170 A1 | 8/2014 |
| WO | WO 2014/127219 A1 | 8/2014 |
| WO | WO 2014/145389 A1 | 9/2014 |
| WO | WO 2014/159356 A1 | 10/2014 |
| WO | WO 2014/170411 A1 | 10/2014 |
| WO | WO 2015/173425 A1 | 11/2015 |
| WO | WO 2016/016894 A1 | 2/2016 |
| WO | WO 2016/056999 A1 | 4/2016 |
| WO | WO 2016/083613 A2 | 6/2016 |

OTHER PUBLICATIONS

U.S. Appl. No. 16/003,293, filed Jun. 8, 2018, Pending.
Partial European Search Report dated May 19, 2016 for Application No. EP 16151949.1.
[No Author Listed] Cambridge Dictionary, definition for "sealed", http://dictionary.cambridge.org/us/dictionary/english/sealed , Sep. 24, 2016, p. 1.
[No Author Listed] An open label dose-escalation study of a self-complementary adeno-associated viral vector (scAAV2/8-LP1-hFIXco) for gene transfer in hemophilia B. ClinicalTrials.gov Archive. Jun. 29, 2010. Identifier NCT00979238. http://clinicaltrials.gov/archive/NTC00979238/2010_06_29. 3 pages.
Apelqvist et al., Notch signalling controls pancreatic cell differentiation. Nature. Aug. 26, 1999;400(6747):877-81.
Azuma et al., Robust expansion of human hepatocytes in Fah-/-/Rag2-/-/Il2rg-/-mice. Nat Biotechnol. Aug. 2007;25(8):903-10. Epub Jul. 29, 2007. Author manuscript available in PMC Jul. 25, 2012.
Hayflick., The cell biology of aging. J Invest Dermatol. Jul. 1979;73(1):8-14.
Hirata et al., Establishment and characterization of hepatic stem-like cell lines from normal adult rat liver. J Biochem. Jan. 2009;145(1):51-8. doi: 10.1093/jb/mvn146. Epub Oct. 30, 2008.
Itoh et al., Inducible expression of Wnt genes during adult hepatic stem/progenitor cell response. FEBS Lett. Feb. 18, 2009;583(4):777-81. doi: 10.1016/j.febslet.2009.01.022. Epub Jan. 25, 2009.
Sen Majumdar et al., Generation of insulin-producing islet-like clusters from human embryonic stem cells. Diabetologia. 2007;50(1):5222-223, Abstract 0530.
International Search Report and Written Opinion for Application No. PCT/EP2015/060815 dated Jul. 28, 2015.

(56) References Cited

OTHER PUBLICATIONS

International Search Report and Written Opinion for Application No. PCT/EP2015/077988 dated Apr. 20, 2016.
International Search Report and Written Opinion for Application No. PCT/EP2015/077990 dated Jul. 6, 2016.
International Search Report and Written Opinion for Application No. PCT/EP2017/054797 dated May 31, 2017.
International Search Report and Written Opinion for Application No. PCT/EP2017/065101 dated Oct. 6, 2017.
European Search Report for Application No. EP 18182285.9 dated Jan. 14, 2019.
"The Wnt Family of Secreted Proteins", R&D Systems' 2004 Catalog, 7 pages (Jan. 1, 2004).
Afroze et al., "The physiological roles of secretin and its receptor." Ann Transl Med. Oct. 2013; 1(3):29. doi: 10.3978/j.issn.2305-5839. 2012.12.01.
Anders et al., Differential expression analysis for sequence count data. Genome Biol. 2010; 11(10):R106. doi: 10.1186/gb-2010-11-10-r106. Epub Oct. 27, 2010.
Brockbank et al., Cryopreservation Guide. 2007. Retrieved from the Internet: https://www.thermofisher.co.nz/Uploads/file/Scientific/Applications/Equipment-Furniture/Cryopreservation-Guide.pdf on May 2, 2019. 30 pages.
Buczacki et al., Intestinal label-retaining cells are secretory precursors expressing Lgr5. Nature. Mar. 7, 2013; 495(7439):65-9. doi: 10.1038/nature11965. Epub Feb. 27, 2013.
Carraway et al., Neuregulin-2, a new ligand of ErbB3/ErbB4-receptor tyrosine kinases. Nature. May 29, 1997; 387(6632):512-6.
Cheng et al., Central and peripheral administration of secretin inhibits food intake in mice through the activation of the melanocortin system. Neuropsychopharmacology. Jan. 2011; 36(2):459-71. doi: 10.1038/npp.2010.178. Epub Oct. 6, 2010.
Cole et al., Measuring GSK3 expression and activity in cells. Methods Mol Biol. 2008; 468:45-65. doi: 10.1007/978-1-59745-249-6_4.
Cuny et al., Structure-activity relationship study of bone morphogenetic protein (BMP) signaling inhibitors. Bioorg Med Chem Lett. Aug. 1, 2008; 18(15):4388-92. doi: 10.1016/j.bmcl.2008.06.052. Epub Jun. 27, 2008.
De Lau et al., The R-spondin/Lgr5/Rnf43 module: regulator of Wnt signal strength. Genes Dev. Feb. 15, 2014;28(4):305-16. doi: 10.1101/gad.235473.113.
Dekkers et al., A functional CFTR assay using primary cystic fibrosis intestinal organoids. Nat Med. Jul. 2013; 19(7):939-45. doi: 10.1038/nm.3201. Epub Jun. 2, 2013.
Dorrell et al., Surface markers for the murine oval cell response. Hepatology. Oct. 2008; 48(4):1282-91. doi: 10.1002/hep.22468.
Eccles, The epidermal growth factor receptor/Erb-B/HER family in normal and malignant breast biology. Int J Dev Biol. 2011; 55(7-9):685-96. doi: 10.1387/ijdb.113396se.
Eden et al., GOrilla: a tool for discovery and visualization of enriched GO terms in ranked gene lists. BMC Bioinformatics. Feb. 3, 2009;10:48. doi: 10.1186/1471-2105-10-48.
Egerod et al., A major lineage of enteroendocrine cells coexpress CCK, secretin, GIP, GLP-1, PYY, and neurotensin but not somatostatin. Endocrinology. Dec. 2012; 153(12):5782-95. doi: 10.1210/en.2012-1595. Epub Oct. 12, 2012.
Farin et al., Redundant sources of Wnt regulate intestinal stem cells and promote formation of Paneth cells. Gastroenterology. Dec. 2012; 143(6):1518-1529.e7. doi: 10.1053/j.gastro.2012.08.031. Epub Aug. 23, 2012.
Farin et al., Visualization of a short-range Wnt gradient in the intestinal stem-cell niche. Nature. Feb. 18, 2016; 530(7590):340-3. doi: 10.1038/nature16937. Epub Feb. 10, 2016.
Gerbal-Chaloin et al., The WNT/β-catenin pathway is a transcriptional regulator of CYP2E1, CYP1A2, and aryl hydrocarbon receptor gene expression in primary human hepatocytes. Mol Pharmacol. Dec. 2014; 86(6):624-34. doi: 10.1124/mol.114.094797. Epub Sep. 16, 2014.
Ghosh et al., Activity assay of epidermal growth factor receptor tyrosine kinase inhibitors in triple-negative breast cancer cells using peptide-conjugated magnetic beads. Assay Drug Dev Technol. Feb. 2013; 11(1):44-51. doi: 10.1089/adt.2012.454. Epub Sep. 20, 2012.
Grün et al., Single-cell messenger RNA sequencing reveals rare intestinal cell types. Nature. Sep. 10, 2015; 525(7568):251-5. doi: 10.1038/nature14966. Epub Apr. 19, 2015.
Gunawardene et al., Classification and functions of enteroendocrine cells of the lower gastrointestinal tract. Int J Exp Pathol. Aug. 2011; 92(4):219-31. doi: 10.1111/j.1365-2613.2011.00767.x. Epub Apr. 25, 2011.
Hashimshony et al., CEL-Seq: single-cell RNA-Seq by multiplexed linear amplification. Cell Rep. Sep. 27, 2012; 2(3):666-73. doi: 10.1016/j.celrep.2012.08.003. Epub Aug. 30, 2012.
Hayashi et al., Establishment and characterization of a parietal endoderm-like cell line derived from Engelbreth-Holm-Swarm tumor (EHSPEL), a possible resource for an engineered basement membrane matrix. Matrix Biol. Apr. 2004;23(1):47-62.
Heuberger et al., Shp2/MAPK signaling controls goblet/paneth cell fate decisions in the intestine. Proc Natl Acad Sci U S A. Mar. 4, 2014; 111(9):3472-7. doi: 10.1073/pnas.1309342111. Epub Feb. 18, 2014.
Höfer et al., Cytoskeletal markers allowing discrimination between brush cells and other epithelial cells of the gut including enteroendocrine cells. Histochem Cell Biol. May 1996; 105(5):405-12.
Hou et al., Pluripotent stem cells induced from mouse somatic cells by small-molecule compounds. Science. Aug. 9, 2013; 341(6146):651-4. doi: 10.1126/science.1239278. Epub Jul. 18, 2013.
Howitt et al., Tuft cells, taste-chemosensory cells, orchestrate parasite type 2 immunity in the gut. Science. Mar. 18, 2016; 351(6279):1329-33. doi: 10.1126/science.aaf1648. Epub Feb. 4, 2016.
Huschtscha et al., Normal human mammary epithelial cells proliferate rapidly in the presence of elevated levels of the tumor suppressors p53 and p21(WAF1/CIP1). J Cell Sci. Aug. 15, 2009; 122(Pt 16):2989-95. doi: 10.1242/jcs.044107. Epub Jul. 28, 2009.
Hynds et al., Concise review: the relevance of human stem cell-derived organoid models for epithelial translational medicine. Stem Cells. Mar. 2013; 31(3):417-22. doi: 10.1002/stem.1290.
Janssen et al., Nutrient sensing in the gut: new roads to therapeutics? Trends Endocrinol Metab. Feb. 2013; 24(2):92-100. doi: 10.1016/j.tem.2012.11.006. Epub Dec. 21, 2012. Author manuscript.
Jeong et al., Neuregulin-1 induces cancer stem cell characteristics in breast cancer cell lines. Oncol Rep. Sep. 2014; 32(3):1218-24. doi: 10.3892/or.2014.3330. Epub Jul. 11, 2014.
Kan et al., p53-mediated growth suppression in response to Nutlin-3 in cyclin D1 transformed cells occurs independently of p21. Cancer Res. Oct. 15, 2007; 67(20):9862-8.
Kogata et al., Neuregulin 3 and erbb signalling networks in embryonic mammary gland development. J Mammary Gland Biol Neoplasia. Jun. 2013; 18(2):149-54. doi: 10.1007/s10911-013-9286-4. Epub May 7, 2013.
Koo et al., Stem cells marked by the R-spondin receptor LGR5. Gastroenterology. Aug. 2014; 147(2):289-302. doi: 10.1053/j.gastro. 2014.05.007. Epub May 21, 2014.
Latorre et al., Enteroendocrine cells: a review of their role in brain-gut communication. Neurogastroenterol Motil. May 2016; 28(5):620-30. doi: 10.1111/nmo.12754. Epub Dec. 21, 2015.
Lee et al., Lung stem cell differentiation in mice directed by endothelial cells via a BMP4-NFATc1-thrombospondin-1 axis. Cell. Jan. 30, 2014; 156(3):440-55. doi: 10.1016/j.cell.2013.12.039.
Lee et al., Neuregulin autocrine signaling promotes self-renewal of breast tumor-initiating cells by triggering HER2/HER3 activation. Cancer Res. Jan. 1, 2014; 74(1):341-52. doi: 10.1158/0008-5472. CAN-13-1055. Epub Oct. 31, 2013.
Manandhar et al., Glucagon-like peptide-1 (GLP-1) analogs: recent advances, new possibilities, and therapeutic implications. J Med Chem. Feb. 12, 2015; 58(3):1020-37. doi: 10.1021/jm500810s. Epub Nov. 13, 2014.
Morin et al., Activation of beta-catenin-Tcf signaling in colon cancer by mutations in beta-catenin or APC. Science. Mar. 21, 1997;275(5307):1787-90.

(56) References Cited

OTHER PUBLICATIONS

Muñoz et al., The Lgr5 intestinal stem cell signature: robust expression of proposed quiescent '+4' cell markers. EMBO J. Jun. 12, 2012; 31(14):3079-91. doi: 10.1038/emboj.2012.166.
Nakamura et al., Anti-patched-1 antibodies suppress hedgehog signaling pathway and pancreatic cancer proliferation. Anticancer Res. Nov.-Dec. 2007; 27(6A):3743-7.
Nakamura et al., Crosstalk between Wnt and Notch signaling in intestinal epithelial cell fate decision. J Gastroenterol. Sep. 2007; 42(9):705-10. Epub Sep. 25, 2007.
Nakanishi et al., Dclk1 distinguishes between tumor and normal stem cells in the intestine. Nat Genet. Jan. 2013; 45(1):98-103. doi: 10.1038/ng.2481. Epub Dec. 2, 2012.
Namkung et al., Small-molecule activators of TMEM16A, a calcium-activated chloride channel, stimulate epithelial chloride secretion and intestinal contraction. FASEB J. Nov. 2011; 25(11):4048-62. doi: 10.1096/fj.11-191627. Epub Aug. 11, 2011.
Oeztuerk-Winder et al., Regulation of human lung alveolar multipotent cells by a novel p38α MAPK/miR-17-92 axis. EMBO J. Aug. 15, 2012; 31(16):3431-41. doi: 10.1038/emboj.2012.192. Epub Jul. 24, 2012.
Pasic et al., Sustained activation of the HER1-ERK1/2-RSK signaling pathway controls myoepithelial cell fate in human mammary tissue. Genes Dev. Aug. 1, 2011; 25(15):1641-53. doi: 10.1101/gad.2025611.
Pin et al., Modelling the spatio-temporal cell dynamics reveals novel insights on cell differentiation and proliferation in the small intestinal crypt. PLoS One. 2012; 7(5):e37115. doi: 10.1371/journal.pone.0037115. Epub May 18, 2012.
Sangiorgi et al., Bmi1 is expressed in vivo in intestinal stem cells. Nat Genet. Jul. 2008; 40(7):915-20. doi: 10.1038/ng.165. Epub Jun. 8, 2008.
Shibue et al., Fatty acid-binding protein 5 regulates diet-induced obesity via GIP secretion from enteroendocrine K cells in response to fat ingestion. Am J Physiol Endocrinol Metab. Apr. 1, 2015; 308(7):E583-91. doi: 10.1152/ajpendo.00543.2014. Epub Jan. 27, 2015.
Smith et al., Comparison of Biosequences, Advances in Applied Mathematics 1981; 2(4):482-489.
Spence et al., Directed differentiation of human pluripotent stem cells into intestinal tissue in vitro. Nature. Feb. 3, 2011; 470(7332):105-9. doi: 10.1038/nature09691. Epub Dec. 12, 2010.
Stepniak et al., c-Jun/AP-1 controls liver regeneration by repressing p53/p21 and p38 MAPK activity. Genes Dev. Aug. 15, 2006; 20(16):2306-14.
Supek et al., REVIGO summarizes and visualizes long lists of gene ontology terms. PLoS One. 2011; 6(7):e21800. doi: 10.1371/journal.pone.0021800. Epub Jul. 18, 2011.
Takeda et al., Interconversion between intestinal stem cell populations in distinct niches. Science. Dec. 9, 2011; 334(6061):1420-4. doi: 10.1126/science.1213214. Epub Nov. 10, 2011.
Terry et al., Impaired enteroendocrine development in intestinal-specific Islet1 mouse mutants causes impaired glucose homeostasis. Am J Physiol Gastrointest Liver Physiol. Nov. 15, 2014; 307(10):G979-91. doi: 10.1152/ajpgi.00390.2013. Epub Sep. 11, 2014.
Tetteh et al., Replacement of Lost Lgr5-Positive Stem Cells through Plasticity of Their Enterocyte-Lineage Daughters. Cell Stem Cell. Feb. 4, 2016; 18(2):203-13. doi: 10.1016/j.stem.2016.01.001. Epub Jan. 28, 2016.
Tisato et al., Upregulation of SOCS-1 by Nutlin-3 in acute myeloid leukemia cells but not in primary normal cells. Clinics (Sao Paulo). Jan. 2014; 69(1):68-74. doi: 10.6061/clinics/2014(01)10.
Trierweiler et al., The transcription factor c-JUN/AP-1 promotes HBV-related liver tumorigenesis in mice. Cell Death Differ. Apr. 2016; 23(4):576-82. doi: 10.1038/cdd.2015.121. Epub Oct. 16, 2015.
Tsai et al., LGR4 and LGR5 Function Redundantly During Human Endoderm Differentiation. Cell Mol Gastroenterol Hepatol. Jun. 23, 2016;2(5):648-662.e8. doi: 10.1016/j.jcmgh.2016.06.002. eCollection Sep. 2016.

Van Es et al., Dll1+ secretory progenitor cells revert to stem cells upon crypt damage. Nat Cell Biol. Oct. 2012; 14(10):1099-1104. doi: 10.1038/ncb2581. Epub Sep. 23, 2012.
Vaughan et al., Lineage-negative progenitors mobilize to regenerate lung epithelium after major injury. Nature. Jan. 29, 2015; 517(7536):621-5. doi: 10.1038/nature14112. Epub Dec. 24, 2014.
Verbeke et al., Humanization of the mouse mammary gland by replacement of the luminal layer with genetically engineered preneoplastic human cells. Breast Cancer Res. Dec. 20, 2014; 16(6):504. doi: 10.1186/s13058-014-0504-9.
Voronkov et al., Wnt/beta-catenin signaling and small molecule inhibitors. Curr Pharm Des. 2013; 19(4):634-64.
Wang et al., Dissecting signaling pathways that govern self-renewal of rabbit embryonic stem cells. J Biol Chem. Dec. 19, 2008;283(51):35929-40.
Wouters et al., Evolution of distinct EGF domains with specific functions. Protein Sci. Apr. 2005;14(4):1091-103.
Yan et al., The intestinal stem cell markers Bmi1 and Lgr5 identify two functionally distinct populations. Proc Natl Acad Sci U S A. Jan. 10, 2012; 109(2):466-71. doi: 10.1073/pnas.1118857109. Epub Dec. 21, 2011.
Yang et al.,β-catenin signaling in murine liver zonation and regeneration: a Wnt-Wnt situation! Hepatology. Sep. 2014; 60(3):964-76. doi: 10.1002/hep.27082. Epub Jul. 25, 2014.
Yin et al., Niche-independent high-purity cultures of Lgr5+ intestinal stem cells and their progeny. Nat Methods. Jan. 2004; 11(1):106-12. doi: 10.1038/nmeth.2737. Epub Dec. 1, 2013.
Yoshimura et al., Vascular endothelial cells and smooth muscle cells mediate carbachol-induced hepatocyte proliferation via muscarinic receptors and IP3/PKC signaling cascades. Cell Biol Int. Apr. 2009; 33(4):516-23.
Yu et al., Cancer therapy. Ex vivo culture of circulating breast tumor cells for individualized testing of drug susceptibility. Science. Jul. 11, 2014; 345(6193):216-20. doi: 10.1126/science.1253533.
Zauli et al., MDM2 antagonist Nutlin-3 suppresses the proliferation and differentiation of human pre-osteoclasts through a p53-dependent pathway. J Bone Miner Res. Oct. 2007; 22(10):1621-30.
Zimmerman, Lung organoid culture. Differentiation. 1987; 36(1):86-109.
Zuo el al., p63(+)Krt5(+) distal airway stem cells are essential for lung regeneration. Nature. Jan. 29, 2015; 517(7536):616-20. doi: 10.1038/nature13903. Epub Nov. 12, 2014.
Couchie et al., In vitro differentiation of WB-F344 rat liver epithelial cells into the biliary lineage. Differentiation. Jan. 2002;69(4-5):209-15. doi: 10.1046/j.1432-0436.2002.690414.x.
Imahori et al., Seikagaku Jiten [Dictionary of Biochemistry]. Oct. 8, 1998;3:808-9.
Nagai et al., Differentiation of liver epithelial (stem-like) cells into hepatocytes induced by coculture with hepatic stellate cells. Biochem Biophys Res Commun. May 24, 2002;293(5):1420-5. doi: 10.1016/S0006-291X(02)00406-0.
Zhang et al., Receptor specificity of the fibroblast growth factor family. The complete mammalian FGF family. J Biol Chem. Jun. 9, 2006;281(23):15694-700. doi: 10.1074/jbc.M601252200. Epub Apr. 4, 2006.
U.S. Appl. No. 12/705,336, filed May 10, 2010, Granted, U.S. Pat. No. 8,906,631.
U.S. Appl. No. 14/494,511, filed Sep. 23, 2014, Granted, U.S. Pat. No. 9,833,496.
U.S. Appl. No. 15/813,863, filed Nov. 15, 2017, Published, 2018-0221441.
U.S. Appl. No. 13/147,163, filed Sep. 14, 2011, Granted, U.S. Pat. No, 8,642,339.
U.S. Appl. No. 14/079,545, filed Nov. 13, 2013, Published, 2014-0256037.
U.S. Appl. No. 16/113,445, filed Aug. 27, 2018, Published, 2019-0100728.
U.S. Appl. No. 13/194,866, filed Jul. 29, 2011, Granted, U.S. Pat. No. 9,752,124.
U.S. Appl. No. 15/654,243, filed Jul. 19, 2017, Published, 2018-0072995.
U.S. Appl. No. 13/812,614, filed Apr. 8, 2013, Granted, U.S. Pat. No. 9,765,301.

(56) References Cited

OTHER PUBLICATIONS

U.S. Appl. No. 14/124,884, filed May 9, 2014, Published, 2014-02432272.
U.S. Appl. No. 14/367,061, filed Jun. 19, 2014, Granted, U.S. Pat. No. 10,006,904.
U.S. Appl. No. 16/003,293, filed Jun. 8, 2018, Published, 2019-0383799.
U.S. Appl. No. 15/310,905, filed Nov. 14, 2016, Granted, U.S. Pat. No. 10,597,633.
U.S. Appl. No. 15/529,346, filed May 24, 2017, Published, 2017-0275592.
U.S. Appl. No. 15/529,150, filed May 24, 2017, Published, 2017-0342385.
Hay et al., Efficient differentiation of hepatocytes from human embryonic stem cells exhibiting markers recapitulating liver development in vivo. Stem Cells. Apr. 2008;26(4):894-902. doi: 10.1634/stemcells.2007-0718. Epub Jan. 31, 2008.
[No Author Listed] Notch Signaling Pathway. Retrieved from the internet <https://www.sinobiological.com/pathways/notch-pathway> Nov. 5, 2020. 3 pages.
[No Author Listed] TGF-beta Inhibitor. Retrieved from the internet <https://kr.sinobiological.com/resource/cytokines/tgf-beta-inhibitors> Nov. 5, 2020. 6 pages.
[No Author Listed] TGF-beta Signaling Pathway. Retrieved from the internet <https://www.sinobiological.com/pathways/tgf-beta-pathway> Nov. 5, 2020. 3 pages.
[No Author Listed] "Art Levinson, Sergey Brin and Anne Wojcicki, Mark Zuckerberg and Priscilla Chan, and Yuri Milner Announce the Breakthrough Prize in Life Sciences", Breakthrough Prize. Feb. 20, 2013: 3pgs. https://breakthroughprize.org/News/12.
Boutten et al., Oncostatin M is a potent stimulator of alpha1-antitrypsin secretion in lung epithelial cells: modulation by transforming growth factor-beta and interferon-gamma. Am J Respir Cell Mol Biol. Apr. 1998;18(4):511-20. doi: 10.1165/ajrcmb.18.4.2772.
Sarzoki et al., Oncostatin M Inhibits TGF-β1-induced CTGF Expression via STAT3 in Human Proximal Tubular Cells. Biochem Biophys Res Commun. Aug. 10, 2012;424(4):801-6. doi: 10.1016/j.bbrc.2012.07.042. Epub Jul. 16, 2012.
U.S. Appl. No. 60/339,739, Tang et al., filed Dec. 10, 2001.
Partial European Search Report dated Jun. 12, 2009 for Application No. EP 9151970.2.
Extended European Search Report for dated Aug. 4, 2009 for Application No. EP 9151970.2.
International Search Report and Written Opinion dated Oct. 8, 2010 for Application No. PCT/NL2010/000017.
International Preliminary Report on Patentability dated Aug. 18, 2011 for Application No. PCT/NL2010/000017.
Partial European Search Report dated Oct. 5, 2010 for Application No. EP 10171265.
International Search Report and Written Opinion dated Jul. 11, 2012 for Application No. PCT/IB2011/002167.
International Preliminary Report on Patentability dated Feb. 7, 2013 for Application No. PCT/IB2011/002167.
Search Report dated Sep. 27, 2011 for Application No. GB 1111244.8.
International Search Report dated Feb. 4, 2013 for Application No. PCT/IB2012/052950.
Notice of Reasons for Rejection dated Sep. 3, 2012 for Application No. JP 2011-547839.
Notice of Reasons for Rejection dated Oct. 3, 2013 for Application No. JP 2012-158676.
Notice of Reasons for Rejection dated Sep. 7, 2015 for Application No. JP 2013-521247.
[No Author Listed] An open label dose-escalation study of a self-complementary adeno-associated viral vector (scAAV2/8-LP1-hFIXco) for gene transfer in hemophilia B. ClinicalTrials.gov Archive. Jun. 29, 2010. Identifier NCT00979238. http://clinicaltrials.gov/archive/NTC00979238/2010_06_29. 3 pages.

[No Author Listed] Definition of "Organoid", MediLexicon Dictionary. 2006, p. 1. http://www.medilexicon.com/medicaldictionary.php?t=63274.
[No Author Listed] Gastroenterology. 2005;128(4):Suppl. 2, A702. Abstract S1225.
[No Author Listed] Ministry of Health, Labour and Welfare, Ethical guidelines for clinical studies. Dated Jul. 30, 2003: p. 3. Accessed from <http://www.mhlw.go.jp/general/seido/kousei/i-kenkyu/rinsyo/dl/shishin.pdf.> Japanese.
[No Author Listed] Purified Human Pancreatic Islets, In Vivo Islets Function. Document No. 3104, A04, Effective Date Jul. 7, 2008. DAIT, NIAID, NIH.
[No Author Listed] The Wnt family of secreted proteins. R&D Systems. Jan. 1, 2004. http://www.rndsystems.com/mini_review_detail_objectname_MR04_WntFamily.aspx. 7 pages.
Abe et al., Apoptosis of mouse pancreatic acinar cells after duct ligation. Arch Histol Cytol. Jun. 1995;58(2):221-9.
Abud et al., Growth of intestinal epithelium in organ culture is dependent on EGF signalling. Exp Cell Res. Feb. 15, 2005;303(2):252-62.
Amado et al., Lentiviral vectors—the promise of gene therapy within reach? Science. Jul. 30, 1999;285(5428):674-6.
Anderson, Human gene therapy. Nature. Apr. 30, 1998;392(6679 Suppl):25-30.
Apelqvtst et al., Notch signalling controls pancreatic cell differentiation. Nature. Aug. 26, 1999;400(6747):877-81.
Apte et al., Wnt/beta-catenin signaling mediates oval cell response in rodents. Hepatology. Jan. 2008;47(1):288-95.
Azuma et al., Robust expansion of human hepatocytes in Fah-/-/Rag2-/-/I12rg-/-mice. Nat Biotechnol. Aug. 2007;25(8):903-10. Epub Jul. 29, 2007. Author manuscript available in PMC Jul. 25, 2012.
Bainbridge et al., Effect of gene therapy on visual function in Leber's congenital amaurosis. N Engl J Med. May 22, 2008;358(21):2231-9. doi: 10.1056/NEJMoa0802268. Epub Apr. 27, 2008.
Bakkebø et al., TGF-β-induced growth inhibition in B-cell lymphoma correlates with Smad1/5 signalling and constitutively active p38 MAPK. BMC Immunol. Nov. 23, 2010;11:57. doi: 10.1186/1471-2172-11-57.
Barker et al., Identification of stem cells in small intestine and colon by marker gene Lgr5. Nature. Oct. 25, 2007;449(7165):1003-7. Epub Oct. 14, 2007.
Barker et al., Lgr5(+ve) stem cells drive self-renewal in the stomach and build long-lived gastric units in vitro. Cell Stem Cell. Jan. 8, 2010;6(1):25-36.
Barker et al., The intestinal stem cell. Genes Dev. Jul. 15, 2008;22(14):1856-64.
Barker et al., Tissue-resident adult stem cell populations of rapidly self-renewing organs. Cell Stem Cell. Dec. 3, 2010;7(6):656-70.
Batlle et al., Beta-catenin and TCF mediate cell positioning in the intestinal epithelium by controlling the expression of EphB/ephrinB. Cell. Oct. 18, 2002; 111(2):251-63.
Binnerts et al., R-Spondin1 regulates Wnt signaling by inhibiting internalization of LRP6. Proc Natl Acad Sci U S A. Sep. 11, 2007;104(37):14700-5. Epub Sep. 2007.
Bjerknes et al., Clonal analysis of mouse intestinal epithelial progenitors. Gastroenterology. Jan. 1999;116(1):7-14.
Bjerknes et al., Intestinal epithelial stem cells and progenitors. Methods Enzymol. 2006;419:337-83.
Bjerknes et al., Multipotential stem cells in adult mouse gastric epithelium. Am J Physiol Gastrointest Liver Physiol. Sep. 2002;283(3):G767-77.
Bodnar et al., Characterization of human islet-like structures generated from pancreatic precursor cells in culture. Biotechnol Bioeng. Apr. 5, 2006;93(5):980-8.
Bonaguidi et al., LIF and BMP signaling generate separate and discrete types of GFAP-expressing cells. Development. Dec. 2005;132(24):5503-14.
Bonaguidi et al., Noggin expands neural stem cells in the adult hippocampus. J Neurosci. Sep. 10, 2008;28(37):9194-204. doi: 10.1523/JNEUROSCI.3314-07.2008.

(56) References Cited

OTHER PUBLICATIONS

Bonner-Weir et al., In vitro cultivation of human islets from expanded ductal tissue. Proc Natl Acad Sci U S A. Jul. 5, 2000;97(14):7999-8004.
Bonner-Weir et al., New sources of pancreatic beta-cells. Nat Biotechnol. Jul. 2005;23(7):857-61.
Booth et al., Maintenance of functional stem cells in isolated and cultured adult intestinal epithelium. Exp Cell Res. Jun. 15, 1999;249(2):359-66.
Booth et al., The isolation and culture of adultmouse colonic epithelium. Epithelial Cell Biol. 1995;4(2):76-86.
Bottenstein et al., Growth of a rat neuroblastoma cell line in serum-free supplemented medium. Proc Natl Acad Sci U S A. Jan. 1979;76(1):514-7.
Bouwens et al., Regulation of pancreatic beta-cell mass. Physiol Rev. Oct. 2005;85(4):1255-70.
Brewer et al., Optimized survival of hippocampal neurons in B27-supplemented Neurobasal, a new serum-free medium combination. J Neurosci Res. Aug. 1, 1993;35(5):567-76.
Brinster et al., Regulation of metallothionein—thymidine kinase fusion plasmids injected into mouse eggs. Nature. Mar. 4, 1982;296(5852):39-42.
Buset et al., Defining conditions to promote the attachment of adult human colonic epithelial cells. In Vitro Cell Dev Biol. Jun. 1987;23(6):403-12. of adult human colonic epithelial cells. In Vitro Cell Dev Biol. Jun. 1987;23(6):403-12.
Capaccio et al., Modern management of obstructive salivary diseases. Acta Otorhinolaryngol Ital. Aug. 2007;27(4):161-72.
Caplen et al., Specific inhibition of gene expression by small double-stranded RNAs in invertebrate and vertebrate systems. Proc Natl Acad Sci U S A. Aug. 14, 2001;98(17):9742-7. Epub Jul. 31, 2001.
Chapman et al., Analysis of spatial and temporal gene expression patterns in blastula and gastrula stage chick embryos. Dev Biol. May 1, 2002;245(1):187-99.
Chen et al., Small molecule-mediated disruption of Wnt-dependent signaling in tissue regeneration and cancer. Nat Chem Biol. Feb. 2009:5(2):100-7. Epub Jan. 4, 2009.
Cheng et al., Origin, differentiation and renewal of the four main epithelial cell types in the mouse small intestine. I. Columnar cell. Am J Anat. Dec. 1974;141(4):461-79.
Chun et al., A new selective and potent inhibitor of human cytochrome P450 1B1 and its application to antimutagenesis. Cancer Res. Nov. 15, 2001;61(22):8164-70. Erratum in: Cancer Res Feb. 15, 2002;62(4):1232.
Clarke et al., Cancer stem cells—perspectives on current status and future directions: AACR Workshop on Cancer Stem Cells. Cancer Res. 2006;66:9339-44.
Clevers et al. Cell Technology. 2009; 28(7):702-03. Japanese.
Clotman et al., Control of liver cell fate decision by a gradient of TGFβ signaling modulated by Onecut transcription factors. Genes & Dev. 2005;19:1849-54.
Crosnier et al., Organizing cell renewal in the intestine: stem cells, signals and combinatorial control. Nat Rev Genet. May 2006;7(5):349-59.
De Gouville et al., Inhibition of TGF-β signaling by an ALK5 inhibitor protects rats from dimethylnitrosamine-induced liver fibrosis. Br J Pharmacol. May 2005;145(2):166-77.
De Lau et al., Lgr5 homologues associate with Wnt receptors and mediate R-spondin signalling. Nature. Jul. 4, 2011;476(7360):293-7. doi: 10.1038/nature10337.
Denu, Vitamin B3 and sirtuin function. Trends Biochem Sci. Sep. 2005;30(9):479-83.
Deveney et al., Establishment of human colonic epithelial cells in long-term culture. J Surg Res. Aug. 1996;64(2):161-9.
Dey et al., Phenotypic and functional characterization of human mammary stem/progenitor cells in long term culture. PLoS One. 2009;4(4):e5329. doi: 10.1371/journal.pone.0005329. Epub Apr. 24, 2009.

Dignass et al., Peptide growth factors in the intestine. Eur J Gastroenterol Hepatol. Jul. 2001;13(7):763-70.
Dong et al.,The epithelial-mesenchymal transition promotes transdifferentiation of subcutaneously implanted hepatic oval cells into mesenchymal tumor tissue. Stem Cells Dev. Nov. 2009;18(9):1293-8. doi: 10.1089/scd.2008.0321.
Dontu et al., Role of Notch signaling in cell-fate determination of human mammary stem/progenitor cells. Breast Cancer Res. 2004:6(6):R605-15. Epub Aug. 16, 2004.
Dor et al., Adult pancreatic beta-cells are formed by self-duplication rather than stem-cell differentiation. Nature. May 6, 2004;429(6987):41-6.
Drew et al., Comparison of 2 cell-based phosphoprotein assays to support screening and development of an ALK inhibitor. J Biomol Screen. Feb. 2011;16(2):164-73. doi: 10.1177/1087057110394657.
Egan et al., Notch receptors, partners and regulators—from conserved domains to powerful functions. Experimental Med. 1998;16(3):200-229. Japanese.
Elbashir et al., Duplexes of 21-nucleotide RNAs mediate RNA interference in cultured mammalian cells. Nature. May 24, 2001;411(6836):494-8.
Evans et al., The development of a method for the preparation of rat intestinal epithelial cell primary cultures. J Cell Sci. Jan. 1992;101 ( Pt 1):219-31.
Federico, Lentiviruses as gene delivery vectors. Curr Opin Biotechnol. Oct. 1999;10(5):448-53.
Fuchs, Inhibition of TGF-β signaling for the treatment of tumor metastasis and fibrotic diseases. Curr Signal Transduction Ther. 2011;6:29-43.
Fukamachi, Proliferation and differentiation of fetal rat intestinal epithelial cells in primary serum-free culture. J Cell Sci. Oct. 1992;103 ( Pt 2):511-9.
Furth et al., Temporal control of gene expression in transgenic mice by a tetracycline-responsive promoter. Proc Natl Acad Sci U S A. Sep. 27, 1994;91(20):9302-6.
Furuyama et al., Continuous cell supply from a Sox9-expressing progenitor zone in adult liver, exocrine pancreas and intestine. Nat Genet. Jan. 2011;43(1):34-41. doi: 10.1038/ng.722. Epub 2010.
Gao et al., Biology of AAV serotype vectors in liver-directed gene transfer to nonhuman primates. Mol Ther. Jan. 2006;13(1):77-87. Epub Oct. 10, 2005.
Garraway et al., Human prostate sphere-forming cells represent a subset of basal epithelial cells capable of glandular regeneration in vivo. Prostate. Apr. 1, 2010;70(5):491-501. doi: 10.1002/pros. 21083.
Geiduschek et al., Transcription by RNA polymerase III. Annu Rev Biochem. 1988:57:873-914.
Githens et al., Rat pancreatic interlobular duct epithelium: isolation and culture in collagen gel. In Vitro Cell Dev Biol. Aug. 1989;25(8):679-88.
Gonçalves et al., Adeno-associated virus: from defective virus to effective vector. Virol J. 2005;2:43. 17 pages.
Gossen et al., Tight control of gene expression in mammalian cells by tetracycline-responsive promoters. Proc Natl Acad Sci U S A. Jun. 15, 1992;89(12):5547-51.
Gradwohl et al., neurogenin3 is required for the development of the four endocrine cell lineages of the pancreas. Proc Natl Acad Sci U S A. Feb. 15, 2000;97(4):1607-11.
Gregorieff et al., Expression pattern of Wnt signaling components in the adult intestine. Gastroenterology. Aug. 2005;129(2):626-38.
Gregorieff et al., Wnt signaling in the intestinal epithelium: from endoderm to cancer. Genes Dev. Apr. 15, 2005;19(8):877-90.
Grossmann et al., Progress on isolation and short-term ex-vivo culture of highly purified non-apoptotic human intestinal epithelial cells (IEC). Eur J Cell Biol. May 2003;82(5):262-70.
Gu et al., Direct evidence for the pancreatic lineage: NGN3+ cells are islet progenitors and are distinct from duct progenitors. Development. May 2002;129(10):2447-57.
Gupta et al., Compilation of small RNA sequences. Nucleic Acids Res. Apr. 25, 1991;19 Suppl:2073-5.
Hao et al., Beta-cell differentiation from nonendocrine epithelial cells of the adult human pancreas. Nat Med. Mar. 2006;12(3):310-6. Epub Feb. 19, 2006.

(56) References Cited

OTHER PUBLICATIONS

Harada et al., Rapid formation of hepatic organoid in collagen sponge by rat small hepatocytes and hepatic nonparenchymal cells. J Hepatol. Nov. 2003;39(5):716-23.
Haramis et al., De novo crypt formation and juvenile polyposis on BMP inhibition in mouse intestine. Science. Mar. 12, 2004;303(5664):1684-6.
Hayflick., The cell biology of aging. J Invest Dermatol. Jul. 1979;73(l):8-14.
Herbst, Review of epidermal growth factor receptor biology. Int J Radiat Oncol Biol Phys. 2004;59(2 Suppl):21-6.
Hernandez, Small nuclear RNA genes: a model system to study fundamental mechanisms of transcription. J Biol Chem. Jul. 20, 2001;276(29):26733-6. Epub Jun. 4, 2001.
Hirata et al., Establishment and characterization of hepatic stem-like cell lines from normal adult rat liver. J Biochem. Jan. 2009;145(1):51-8. doi: 10.1093/jh/mvn146. Epub Oct. 30, 2008.
Hodin et al., Immediate-early gene expression in EGF-stimulated intestinal epithelial cells. J Surg Res. Jun. 1994;56(6):500-4.
Hofmann et al., Cell-cell contacts prevent anoikis in primary human colonic epithelial cells. Gastroenterology. Feb. 2007;132(2):587-600.
Hong et al., Proteomic analysis of differential protein expression in response to epidermal growth factor in neonatal porcine pancreatic cell monolayers. J Cell Biochem. Jul. 1, 2005;95(4):769-81.
Horikoshi et al., High-Speed Knock-In, Functional analyses of secreted proteins by high-speed knock-in (HSKI) system II: intestinotrophic activities of R-spondin family proteins. Seikagaku. 2007:3P-1232.
Howe et al., The responsiveness of a tetracycline-sensitive expression system differs in different cell lines. J Biol Chem. Jun. 9, 1995;270(23):14168-74.
Hsieh et al., Truncated mammalian Notch1 activates CBF1/RBPJk-repressed genes by a mechanism resembling that of Epstein-Barr virus EBNA2. Mol Cell Biol. Mar. 1996;16(3):952-9.
Hu et al., Wnt/β-catenin signaling in murine hepatic transit amplifying progenitor cells. Gastroenterology. Nov. 2007;133(5):1579-91. Epub Aug. 28, 2007.
Huch et al., In vitro expansion of single Lgr5+ liver stem cells induced by Wnt-driven regeneration. Nature. Feb. 14, 2013;494(7436):247-50. doi: 10.1038/nature11826. Epub Jan. 27, 2013.
Huch et al., Long-term culture of genome-stable bipotent stem cells from adult human liver. Cell. Jan. 15, 2015;160(1-2):299-312.doi: 10.1016/j.cell.2014.11.050. Epub Dec. 18, 2014.
Huch et al., Urokinase-type plasminogen activator receptor transcriptionally controlled adenoviruses eradicate pancreatic tumors and liver metastasis in mouse models. Neoplasia. Jun. 2009;11(6):518-28, 4 p following 528.
Igarashi et al., Characterization of recombinant human fibroblast growth factor (FGF)-10 reveals functional similarities with keratinocyte growth factor (FGF-7). J Biol Chem. May 22, 1998;273(21):13230-5.
Itoh et al., Inducible expression of Wnt genes during adult hepatic stein/progenitor cell response. FEBS Lett. Feb. 18, 2009;583(4):777-81. doi: 10.1016/j.febslet.2009.01.022. Epub Jan. 25, 2009.
Jaks et al., Lgr5 marks cycling, yet long-lived, hair follicle stem cells. Nat Genet. Nov. 2008;40(11):1291-9. Epub Oct. 12, 2008.
Jensen et al., t-box Genes in Early Embryogenesis, Developmental Dynamics, 2004. vol. 229, 201-18.
Jiang, et al., Generation of insulin-producing islet-like clusters from human embryonic stem cells, Stem Cells. Aug. 2007;25(8):1940-53.
Kadesch, Notch signaling: a dance of proteins changing partners. Exp Cell Res. Oct. 10, 2000;260(1):1-8.
Kaplitt et al., Safety and tolerability of gene therapy with an adeno-associated virus (AAV) borne GAD gene for Parkinson's disease: an open label, phase I trial. Lancet. Jun. 23, 2007;369(9579):2097-105.
Kawasaki et al., Effects of growth factors on the growth and differentiation of mouse fetal liver epithelial cells in primary cultures. J Gastroenterol Hepatol. Jun. 2005;20(6):857-64.
Kay et al., Viral vectors for gene therapy: the art of turning infectious agents into vehicles of therapeutics. Nat Med. Jan. 2001;7(1):33-40.
Kedinger et al., Intestinal epithelial-mesenchymal cell interactions. Ann N Y Acad Sci. Nov. 17, 1998;859:1-17.
Kemp et al. The Roles of Wnt Signaling in Early Mouse Development and Embryonic Stem Cells. Functional Development and Embryology. 2007. 1(1): 1-13. Last accessed at http://www.globalsciencebooks.info/JournalsSup/images/SF/FDE_1(1)1-13.pdf Jan. 21, 2014.
Kerr-Conte et al., Ductal cyst formation in collagen-embedded adult human islet preparations. A means to the reproduction of nesidioblastosis in vitro. Diabetes. Aug. 1996;45(8):1108-14.
Kim et al., In vivo functioning and transplantable mature pancreatic islet-like cell clusters differentiated from embryonic stem cell. Pancreas. Aug. 2003;27(2):e34-41.
Kim et al., Mitogenic influence of human R-spondin1 on the intestinal epithelium. Science. Aug. 19, 2005;309(5738):1256-9.
Kirikoshi et al., WNT10A and WNT6, clustered in human chromosome 2q35 region with head-to-tail manner, are strongly coexpressed in SW480 cells. Biochem Biophys Res Commun. May 18, 2001;283(4):798-805.
Kitisin et al., Hepatocellular stem cells. Cancer Biomark. 2007;3(4-5):251-62.
Korinek et al., Constitutive transcriptional activation by a beta-catenin-Tcf complex in APC-/- colon carcinoma. Science. Mar. 21, 1997;275(5307):1784-7.
Korinek et al., Depletion of epithelial stem-cell compartments in the small intestine of mice lacking Tcf-4. Nat Genet. Aug. 1998;19(4):379-83.
Kuhnert et al., Essential requirement for Wnt signaling in proliferation of adult small intestine and colon revealed by adenoviral expression of Dickkopf-1. Proc Natl Acad Sci U S A. Jan. 6, 2004;101(1):266-71. Epub Dec. 26, 2003.
Latella et al., Characterization of the mucins produced by normal human colonocytes in primary culture. Int J Colorectal Dis. 1996;11(2):76-83.
Lee et al., In vitro hepatic differentiation of human mesenchymal stem cells. Hepatology. Dec. 2004;40(6):1275-84.
Lee et al., The role of gremlin, a BMP antagonist, and epithelial-to-mesenchymal transition in proliferative vitreoretinopathy. Invest Ophthalmol Vis Sci. Sep. 2007;48(9):4291-9.
Lefebvre et al., Culture of adult human islet preparations with hepatocyte growth factor and 804G matrix is mitogenic for duct cells but not for beta-cells. Diabetes. Jan. 1998;47(1):134-7.
Lemaigre, Mechanisms of liver development: concepts for understanding liver disorders and design of novel therapies. Gastroenterology. Jul. 2009;137(1):62-79.
Leost et al., Paullones are potent inhibitors of glycogen synthase kinase-3beta and cyclin-dependent kinase 5/p25. Eur J Biochem. Oct. 2000;267(19):5983-94.
Li et al., Stem cell niche: structure and function. Annu Rev Cell Dev Biol. 2005;21:605-31.
Li et al., The human homolog of rat Jagged1 expressed by marrow stroma inhibits differentiation of 32D cells through interaction with Notch1. Immunity. Jan. 1998;8(1):43-55.
Liao et al., Glycogen synthase kinase-3beta activity is required for androgen-stimulated gene expression in prostate cancer. Endocrinology. Jun. 2004;145(6):2941-9. Epub Feb. 26, 2004.
Little et al., Engineering biomaterials for synthetic neural stem cell microenvironments. Chem Rev. May 2008;108(5):1787-96.
Liu et al., A novel chemical-defined medium with bFGF and N2B27 supplements supports undifferentiated growth in human embryonic stem cells. Biochem Biophys Res Commun. Jul. 21, 2006;346(1):131-9. Epub May 24, 2006.
Liu et al., A small-molecule agonist of the Wnt signaling pathway. Angew Chem Int Ed Engl. Mar. 18, 2005;44(13):1987-90.
Lowes et al., Oval cell-mediated liver regeneration: Role of cytokines and growth factors. J Gastroenterol Hepatol. Jan. 2003;18(1):4-12.

(56) References Cited

OTHER PUBLICATIONS

Lustig et al., Negative feedback loop of Wnt signaling through upregulation of conductin/axin2 in colorectal and liver tumors. Mol Cell Biol. Feb. 2002;22(4):1184-93.
Macchiarini et al., Clinical transplantation of a tissue-engineered airway. Lancet. Dec. 13, 2008;372(9655):2023-30. doi: 10.1016/S0140-6736(08)61598-6. Epub Nov. 18, 2008.
Mader et al., A steroid-inducible promoter for the controlled overexpression of cloned genes in eukaryotic cells. Proc Natl Acad Sci U S A. Jun. 15, 1993;90(12):5603-7.
Maguire et al., Safety and efficacy of gene transfer for Leber's congenital amaurosis. N Engl J Med. May 22, 2008;358(21):2240-8. Epub Apr. 27, 2008. Author manuscript available in PMC Mar. 1, 2010.
Malorni et al., The antioxidant N-acetyl-cysteine protects cultured epithelial cells from menadione-induced cytopathology. Chem Biol Interact. May 19, 1995;96(2):113-23.
Manno et al., Successful transduction of liver in hemophilia by AAV-Factor IX and limitations imposed by the host immune response. Nat Med. Mar. 2006;12(3):342-7. Epub Feb. 12, 2006. Erratum in: Nat Med. May 2006:12(5):592. Rasko, John [corrected to Rasko, John JE]; Rustagi, Pradip K [added].
Marin et al., Towards efficient cell targeting by recombinant retroviruses. Mol Med Today. Sep. 1997;3(9):396-403.
Martin-Belmonte et al., Cell-polarity dynamics controls the mechanism of lumen formation in epithelial morphogenesis. Curr Biol. Apr. 8, 2008;18(7):507-13. doi: 10.1016/j.cub.2008.02.076. Erratum in: Curr Biol. Jul. 8, 2008;18(13):1016. Curr Biol. Apr. 22, 2008;18(8):630.
Mason et al., Entrapped collagen type 1 promotes differentiation of embryonic pancreatic precursor cells into glucose-responsive beta-cells when cultured in three-dimensional PEG hydrogels. Tissue Eng Part A. Dec. 2009;15(12):3799-808. doi: 10.1089/ten.TEA.2009.0148.
Mattaj et al., Changing the RNA polymerase specificity of U snRNA gene promoters. Cell. Nov. 4, 1988;55(3):435-42.
Mayo et al., The mouse metallothionein-I gene is transcriptionally regulated by cadmium following transfection into human or mouse cells. Cell. May 1982;29(1):99-108.
McEwen et al., Regulation of the fibroblast growth factor receptor 3 promoter and intron I enhancer by Sp1 family transcription factors. J Biol Chem. Feb. 27, 1998;273(9):5349-57.
Meijer et al., GSK-3-selective inhibitors derived from Tyrian purple indirubins. Chem Biol. Dec. 2003;10(12):1255-66.
Meijer et al., Pharmacological inhibitors of glycogen synthase kinase 3. Trends Pharmacol Sci. Sep. 2004:25(9):471-80.
Menke et al., Conversion of metaplastic Barrett's epithelium into post-mitotic goblet cells by gamma-secretase inhibition. Dis Model Mech. Jan.-Feb. 2010:3(1-2):104-10. doi: 10.1242/dmm.003012.
Metzger et al., The human oestrogen receptor functions in yeast. Nature. Jul. 7, 1988:334(6177):31-6.
Miralles et al., Signaling through fibroblast growth factor receptor 2b plays a key role in the development of the exocrine pancreas. Proc Natl Acad Sci U S A. May 25, 1999;96(11):6267-72.
Mirochnik et al., Androgen receptor drives cellular senescence. PLoS One. 2012;7(3):e31052. doi: 10.1371/journal.pone.0031052. Epub Mar. 5, 2012.
Mitaka, Reconstruction of hepatic organoid by hepatic stem cells. J Hepatobiliary Pancreat Surg. 2002;9(6):697-703.
Mizuochi et al., Infection, inflammation and immunity. 2004;34(2):40-52. Japanese.
Montesano et al., Collagen matrix promotes reorganization of pancreatic endocrine cell monolayers into islet-like organoids. J Cell Biol. Sep. 1983:97(3):935-9.
Mori et al., Micropatterned organoid culture of rat hepatocytes and HepG2 cells. J Biosci Bioeng. Sep. 2008;106(3):237-42.
Myslinski et al., An unusually compact external promoter for RNA polymerase III transcription of the human H1RNA gene. Nucleic Acids Res. Jun. 15, 2001;29(12):2502-9.
Naftalin et al., Progesterone stimulation of fluid absorption by the rat uterine gland. Reproduction. May 2002;123(5):633-8.
Nasonkin et al., Nonhuman sialic acid Neu5Gc is very low in human embryonic stem cell-derived neural precursors differentiated with B27/N2 and noggin: implications for transplantation. Exp Neurol. Oct. 2006;201(2):525-9.
Niu et al., Differential androgen receptor signals in different cells explain why androgen-deprivation therapy of prostate cancer fails. Oncogene. Jun. 24, 2010;29(25):3593-604. doi: 10.1038/onc.2010.121. Epub May 3, 2010.
Odze, Barrett esophagus: histology and pathology for the clinician. Nat Rev Gastroenterol Hepatol. Aug. 2009;6(8):478-90. doi: 10.1038/nrgastro.2009.103. Epub Jul. 7, 2009.
Ootani et al., Foveolar differentiation of mouse gastric mucosa in vitro. Am J Pathol. Jun. 2003;162(6):1905-12.
Ootani et al., Sustained in vitro intestinal epithelial culture within a Wnt-dependent stem cell niche. Nat Med. Jun. 2009;15(6):701-6. doi: 10.1038/nm.1951. Epub Apr. 27, 2009.
Otsuka et al., Distinct effects of p38alpha deletion in myeloid lineage and gut epithelia in mouse models of inflammatory bowel disease. Gastroenterology. Apr. 2010;138(4):1255-65, 1265.e1-9. doi: 10.1053/j.gastro.2010.01.005. Epub Jan. 18, 2010. Includes Supplemental Information.
Overturf et al., Hepatocytes corrected by gene therapy are selected in vivo in a murine model of hereditary tyrosinaemia type I. Nat Genet. Mar. 1996;12(3):266-73.
Pang et al., Immunologic, functional, and morphological characterization of three new human small intestinal epithelial cell lines. Gastroenterology. Jul. 1996;111(1):8-18.
Panja, A novel method for the establishment of a pure population of nontransformed human intestinal primary epithelial cell (HIPEC) lines in long term culture. Lab Invest. Sep. 2000;80(9):1473-5.
Peng et al., Inhibition of p38 MAPK facilitates ex vivo expansion of skin epithelial progenitor cells. In Vitro Cell Dev Biol Anim. Oct. 2009;45(9):558-65. doi: 10.1007/s11626-009-9223-4. Epub Jun. 24, 2009. expansion of skin epithelial progenitor cells. In Vitro Cell Dev Biol Anim. Oct. 2009;45(9):558-65. doi: 10.1007/s11626-009-9223-4. Epub Jun. 24, 2009.
Peng et al., Viral vector targeting. Curr Opin Biotechnol. Oct. 1999;10(5):454-7.
Perreault et al., Use of the dissociating enzyme thermolysin to generate viable human normal intestinal epithelial cell cultures. Exp Cell Res. May 1, 1996;224(2):354-64.
Petersen et al., Interaction with basement membrane serves to rapidly distinguish growth and differentiation pattern of normal and malignant human breast epithelial cells. Proc Natl Acad Sci U S A. Oct. 1, 1992:89(19):9064-8.
Pettipher et al., Antagonism of the prostaglandin D2 receptors DP1 and CRTH2 as an approach to treat allergic diseases. Nat Rev Drug Discov. Apr. 2007;6(4):313-25.
Pinto et al., Canonical Wnt signals are essential for homeostasis of the intestinal epithelium. Genes Dev. Jul. 15, 2003;17(14):1709-13.
Planutis et al., Regulation of norrin receptor frizzled-4 by Wnt2 in colon-derived cells. BMC Cell Biol. Mar. 26, 2007;8:12.
Powell et al., Myofibroblasts. II. Intestinal subepithelial myofibroblasts. Am J Physiol. Aug. 1999;277(2 Pt 1):C183-201.
Ramiya et al., Reversal of insulin-dependent diabetes using islets generated in vitro from pancreatic stem cells. Nat Med. Mar. 2000;6(3):278-82.
Reiser, Production and concentration of pseudotyped HIV-1-based gene transfer vectors. Gene Ther. Jun. 2000;7(11):910-3.
Resnitzky et al., Acceleration of the G1/S phase transition by expression of cyclins D1 and E with an inducible system. Mol Cell Biol. Mar. 1994;14(3):1669-79.
Robinton et al., The promise of induced pluripotent stem cells in research and therapy. Nature. Jan. 18, 2012:481(7381):295-305. doi: 10.1038/nature10761.
Rogler et al., Differential activation of cytokine secretion in primary human colonic fibroblast/myofibroblast cultures. Scand J Gastroenterol. Apr. 2001;36(4):389-98.
Rokutan et al., Epidermal growth factor-induced mitogen signals in cultured intestinal epithelial cells. J Gastroenterol. Jul. 1994;29 Suppl 7:59-62.

(56) References Cited

OTHER PUBLICATIONS

Rooman et al., Mitogenic effect of gastrin and expression of gastrin receptors in duct-like cells of rat pancreas.Gastroenterology. Oct. 2001;121(4):940-9.

Rooman et al., Modulation of rat pancreatic acinoductal transdifferentiation and expression of PDX-1 in vitro. Diabetologia. Jul. 2000;43(7):907-14.

Russell, Update on adenovirus and its vectors. J Gen Virol. Nov. 2000;81(Pt 11):2573-604.

Saha et al., Designing synthetic materials to control stem cell phenotype. Curr Opin Chem Biol. Aug. 2007;11(4):381-7. Epub Jul. 31, 2007.

Saha et al., Substrate modulus directs neural stem cell behavior. Biophys J. Nov. 1, 2008;95(9):4426-38. Epub Jul. 25, 2008.

Sansom et al., Loss of Apc in vivo immediately perturbs Wnt signaling, differentiation, and migration. Genes Dev. Jun. 15, 2004;18(12):1385-90.

Sasaki et al., Expression and distribution of laminin alpha1 and alpha2 chains in embryonic and adult mouse tissues: an immunochemical approach. Exp Cell Res. May 1, 2002;275(2):185-99.

Sato et al., Long-term expansion of epithelial organoids from human colon, adenoma, adenocarcinoma, and Barrett's epithelium. Gastroenterology. Nov. 2011;141(5):1762-72.

Sato et al., Paneth cells constitute the niche for Lgr5 stem cells in intestinal crypts. Nature. Jan. 20, 2011;469(7330):415-8. doi: 10.1038/nature09637. Epub Nov. 28, 2010.

Sato et al., Single Lgr5 stem cells build crypt-villus structures in vitro without a mesenchymal niche. Nature. May 14, 2009;459(7244):262-5.

Sato et al., G.I Research. 2004;12(2):3-10. Japanese.

Sawada et al., Selective killing of Paneth cells by intravenous administration of dithizone in rats. Int J Exp Pathol. Aug. 1991;72(4):407-21.

Schroter et al., Detection of myosin light chain phosphorylation—a cell-based assay for screening Rho-kinase inhibitors. Biochem Biophys Res Commun. Sep. 19, 2008;374(2):356-60. Epub Jul. 16, 2008.

Schwitzgebel et al., Expression of neurogenin3 reveals an islet cell precursor population in the pancreas. Development. Aug. 2000;127(16):3533-42.

Seaberg et al., Clonal identification of multipotent precursors from adult mouse pancreas that generate neural and pancreatic lineages. Nat Biotechnol. Sep. 2004;22(9):1115-24. Epub Aug. 22, 2004.

Segev et al., Differentiation of human embryonic stem cells into insulin-producing clusters. Stem Cells. 2004;22(3):265-74.

Semler et al., Mechanochemical manipulation of hepatocyte aggregation can selectively induce or repress liver-specific function. Biotechnol Bioeng. Aug. 20, 2000;69(4):359-69.

Sen Majumdar et al., Generation of insulin-producing islet-like clusters from human embryonic stem cells. Diabetologia. 2007;50(1):S222-223. Abstract 0530.

Shay et al., Telomerase therapeutics for cancer: challenges and new directions. Nat Rev Drug Discov. Jul. 2006;5(7):577-84. Epub Jun. 9, 2006.

Shockett et al., A modified tetracycline-regulated system provides autoregulatory, inducible gene expression in cultured cells and transgenic mice. Proc Natl Acad Sci U S A. Jul. 3, 1995;92(14):6522-6.

Showell et al., T-box genes in early embryogenesis. Dev Dyn. Jan. 2004;229(1):201-18.

Snippert et al., Intestinal crypt homeostasis results from neutral competition between symmetrically dividing Lgr5 stem cells. Cell. Oct. 1, 2010;143(1):134-44. doi: 10.1016/j.cell.2010.09.016.

Snippert et al., Lgr6 marks stem cells in the hair follicle that generate all cell lineages of the skin. Science. Mar. 12, 2010;327(5971):1385-9. doi: 10.1126/science.1184733.

Snykers et al., Differentiation of neonatal rat epithelial cells from biliary origin into immature hepatic cells by sequential exposure to hepatogenic cytokines and growth factors reflecting liver development. Toxicol In Vitro. Oct. 2007;21(7):1325-31. Epub Apr. 4, 2007.

Snykers et al., In vitro differentiation of embryonic and adult stem cells into hepatocytes: state of the art. Stem Cells. Mar. 2009;27(3):577-605.

Sommerfelt, Retrovirus receptors. J Gen Virol. Dec. 1999;80 ( Pt 12):3049-64.

Soriano, Generalized lacZ expression with the ROSA26 Cre reporter strain. Nat Genet. Jan. 1999;21(1):70-1.

Spradling, Drummond-Barbosa D, Kai T. Stem cells find their niche. Nature.Nov. 1, 2001;414(6859):98-104.

Srinivas et al., Cre reporter strains produced by targeted insertion of EYFP and ECFP into the ROSA26 locus. BMC Dev Biol. 2001;1:4. Epub Mar. 27, 2001.

St Clair et al., Crypt fission and crypt number in the small and large bowel of postnatal rats. Cell Tissue Kinet. May 1985;18(3):255-62.

St Clair et al., Inhibition by ganciclovir of cell growth and DNA synthesis of cells biochemically transformed with herpesvirus genetic information. Antimicrob Agents Chemother. Jun. 1987;31(6):844-9.

Stingl et al., Characterization of bipotent mammary epithelial progenitor cells in normal adult human breast tissue. Breast Cancer Res Treat. May 2001;67(2):93-109.

Stingl et al., Purification and unique properties of mammary epithelial stem cells. Nature. Feb. 23, 2006;439(7079):993-7. Epub Jan. 4, 2006.

Stroes et al., Intramuscular administration of AAV1-lipoprotein lipase S447X lowers triglycerides in lipoprotein lipase-deficient patients. Arterioscler Thromb Vasc Biol. Dec. 2008;28(12):2303-4. Supplementary Tables and Figures 8 pages.

Suzuki et al., Prospective isolation of multipotent pancreatic progenitors using flow-cytometric cell sorting. Diabetes. Aug. 2004;53(8):2143-52.

Suzuki et al., Role for growth factors and extracellular matrix in controlling differentiation of prospectively isolated hepatic stem cells. Development. Jun. 2003;130(11):2513-24.

Teta et al., Growth and regeneration of adult beta cells does not involve specialized progenitors. Dev Cell. May 2007;12(5):817-26.

Thenappan et al., Role of transforming growth factor beta signaling and expansion of progenitor cells in regenerating liver. Hepatology. Apr. 2010;51(4):1373-82. doi: 10.1002/hep.23449.

Thomas et al., Role of gastrointestinal hormones in the proliferation of normal and neoplastic tissues. Endocr Rev. Oct. 2003;24(5):571-99.

Touhami et al., The role of NGF signaling in human limbal epithelium expanded by amniotic membrane culture. Invest Ophthalmol Vis Sci. Apr. 2002;43(4):987-94.

Trautmann et al., Isolation, culture, and characterization of human pancreatic duct cells. Pancreas. Mar. 1993;8(2):248-54.

Ueno, Morio Biotechnology Journal. 2007;11-12:701-5. Japanese.

Van De Wetering et al., Mutant E-cadherin breast cancer cells do not display constitutive Wnt signaling. Cancer Res. Jan. 1, 2001;61(1):278-84.

Van De Wetering et al., The beta-catenin/TCF-4 complex imposes a crypt progenitor phenotype on colorectal cancer cells. Cell. Oct. 18, 2002;111(2):241-50.

Van Der Flier et al., Transcription factor achaete scute-like 2 controls intestinal stem cell fate. Cell. Mar. 6, 2009;136(5):903-12.

Van Es et al., Notch/gamma-secretase inhibition turns proliferative cells in intestinal crypts and adenomas into goblet cells. Nature. Jun. 16, 2005;435(7044):959-63.

Vigna et al., Lentiviral vectors: excellent tools for experimental gene transfer and promising candidates for gene therapy. J Gene Med. Sep.-Oct. 2000;2(5):308-16.

Vincan et al., Frizzled-7 dictates three-dimensional organization of colorectal cancer cell carcinoids. Oncogene. Apr. 5, 2007;26(16):2340-52. Epub Oct. 2, 2006.

Visco et al., Differential response to keratinocyte growth factor receptor and epidermal growth factor receptor ligands of proliferating and differentiating intestinal epithelial cells. J Cell Physiol. J Cell Physiol. Jul. 2004;200(1):31-44.

Walen, Spontaneous cell transformation: karyoplasts derived from multinucleated cells produce new cell growth in senescent human epithelial cell cultures. In Vitro Cell Dev Biol Anim. May-Jun. 2004;40(5-6):150-8.

(56) References Cited

OTHER PUBLICATIONS

Walther et al., Viral vectors for gene transfer: a review of their use in the treatment of human diseases. Drugs. Aug. 2000;60(2):249-71.
Wang et al., A regulatory system for new use in gene transfer. Proc. Natl. Acad. Sci. USA. 1994;91:8180-4.
Wang et al., Duct- to islet-cell differentiation and islet growth in the pancreas of duct-ligated adult rats. Diabetologia. Dec. 1995;38(12):1405-11.
Wang et al., Regulation of TRAIL expression by the phosphatidylinositol 3-kinase/Akt/GSK-3 pathway in human colon cancer cells. J Biol Chem. Sep. 27, 2002;277(39):36602-10.
Watanabe et al., A ROCK inhibitor permits survival of dissociated human embryonic stem cells. Nat Biotechnol. Jun. 2007;25(6):681-6. Epub May 27, 2007.
Whitehead et al., A method for the isolation and culture of human colonic crypts in collagen gels. In Vitro Cell Dev Biol. Jun. 1987;23(6):436-42.
Whitehead et al., Clonogenic growth of epithelial cells from normal colonic mucosa from both mice and humans. Gastroenterology. Oct. 1999;117(4):858-65.
Willert et al., Wnt proteins are lipid-modified and can act as stem cell growth factors. Nature. May 22, 2003;423(6938):448-52. Epub Apr. 27, 2003.
Williams et al., The role of the Wnt family of secreted proteins in rat oval "stem" cell-based liver regeneration: Wnt1 drives differentiation. Am J Pathol. Jun. 2010;176(6):2732-42. Epub Apr. 22, 2010.
Willis, RNA polymerase III. Genes, factors and transcriptional specificity. Eur J Biochem. Feb. 15, 1993;212(1):1-11.
Xu et al., Beta cells can be generated from endogenous progenitors in injured adult mouse pancreas. Cell. Jan. 25, 2008;132(2):197-207.
Yang et al., In vitro trans-differentiation of adult hepatic stem cells into pancreatic endocrine hormone-producing cells. Proc Natl Acad Sci U S A. Jun. 11, 2002;99(12):8078-83. Epub Jun. 4, 2002.
Yaswen et al., Isolation of oval cells by centrifugal elutriation and comparison with other cell types purified from normal and preneoplastic livers. Cancer Res. Jan. 1984;44(1):324-31.
Yen, The gastrointestinal tract stem cell niche. Stem Cell Rev. 2006;2(3):203-12.
Zaret, Genetic programming of liver and pancreas progenitors: lessons for stem-cell differentiation. Nat Rev Genet. May 2008;9(5):329-40. doi:10.1038/nrg2318.
Zhou et al., Oxidative stress-induced intestinal epithelial cell apoptosis is mediated by p38 MAPK. Biochem Biophys Res Commun. Dec. 1, 2006;350(4):860-5. Epub Sep. 29, 2006.
Zhu et al., Chemical strategies for stem cell biology and regenerative medicine. Annu Rev Biomed Eng. Aug. 15, 2011;13:73-90.
Zilberberg et al., A rapid and sensitive bioassay to measure bone morphogenetic protein activity. BMC Cell Biol. Sep. 19, 2007;8:41.
Zong et al., Notch signaling controls liver development by regulating biliary differentiation. Development. May 2009;136(10):1727-39. doi: 10.1242/dev.029140. Epub Apr. 15, 2009.

* cited by examiner

Day 10 after sort

|  | ER | ENR | ENRW | Liver (adult) |
|---|---|---|---|---|
| G6pc2 | 119.5 | 122 | 125 | 117.5 |
| G6pc3 | 4679.5 | 4340.5 | 4139.5 | 685.5 |
| Glul | 923.5 | 839.5 | 1387 | 18345 |
| Met | 5337 | 5743.5 | 4122 | 1828.5 |
| Hnf1a | 10980 | 9865 | 6176 | 8334 |
| Hnf1b | 2357 | 2632 | 2770.5 | 361 |
| Hnf4a | 1336 | 1283 | 1086 | 4033 |
| Cyp39a1 | 1190.5 | 1167 | 1391 | 1051 |
| Cyp2j6 | 938.5 | 918 | 998.5 | 1164 |
| Cyp3a13 | 344 | 426.5 | 244 | 10787 |
| Cyp4b1 | 1567 | 1567 | 370.5 | 2247 |
| Lap3 | 4704 | 4659.5 | 5069.5 | 20262 |
| Krt7 | 163790 | 161041 | 195354 | 386.5 |
| Krt19 | 88264 | 79467.5 | 54949.5 | 347 |

Fig. 7A
Fig. 7B
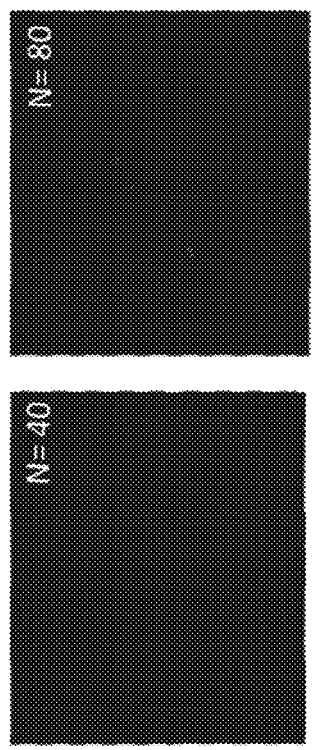

After first split 5 days after differentiation

Fig. 9

Bile duct specific TF

|       | E      | ER     | ER     | ENRW   | Mouse adult liver |
|-------|--------|--------|--------|--------|-------------------|
| Hnf1b | 3118,5 | 2357   | 2632   | 2770,5 | 361               |
| Onecut2 | 34223,5 | 13172 | 21655 | 14926,5 | 6865            |
| Onecut1 | 6435 | 2473,5 | 4083   | 2721   | 1438,5            |
| Foxa2 | 16123  | 10962,5 | 10970 | 11872  | 5789              |
| Hes1  | 1752   | 965    | 1453,5 | 1018   | 194               |
| Sox9  | 4861,5 | 7490   | 6738,5 | 7547   | 426               |

HC specific TF

| Gata6 | 4981,5 | 5381  | 5124  | 5184  | 740   |
|-------|--------|-------|-------|-------|-------|
| Cebpa | 1431   | 1188  | 856   | 946   | 10640 |
| Hnf1a | 11640  | 10980 | 9865  | 6176  | 8334  |
| Hnf4a | 2573   | 1336  | 1283  | 1086  | 4033  |

| Prox1 | 495   | 219,5 | 379,5 | 319   | 2139   |
|-------|-------|-------|-------|-------|--------|
| Tbx3  | 196,5 | 214   | 208   | 180   | 1840,5 |
| Nr5a2 | 132   | 139   | 131,5 | 141   | 1234   |

Notch signaling

| Jag1   | 6832,5 | 3638,5 | 4111   | 3394   | 343   |
|--------|--------|--------|--------|--------|-------|
| Dll1   | 4035   | 3758   | 2791,5 | 2714,5 | 415,5 |
| Notch3 | 557    | 718    | 476    | 788    | 234   |

TGFb signaling

| Tgfbr1 | 3439 | 2971 | 4281  | 3664  | 733  |
|--------|------|------|-------|-------|------|
| Tgfbr1 | 245  | 234  | 243   | 210   | 116  |

| Tgfbr2 | 8442 | 9942 | 13874 | 11392 | 1364 |

E=EGF 50ng/ml
A=A8301 50nM
D=DAPT 10nM
F=FGF10 100ng/ml
H=HGF 50ng/ml

Nic=Nicotinamide 10nM
R=Rspondin1 500ng/ml
Wnt= Wnt conditioned media 50%

E=EGF 50ng/ml
A=A8301 50nM
D=DAPT 10nM
F=FGF10 100ng/ml
H=HGF 50ng/ml

Nic=Nicotinamide 10nM
R=Rspondin1 500ng/ml
Wnt= Wnt conditioned media 50%
De= dexamethasone 10mM

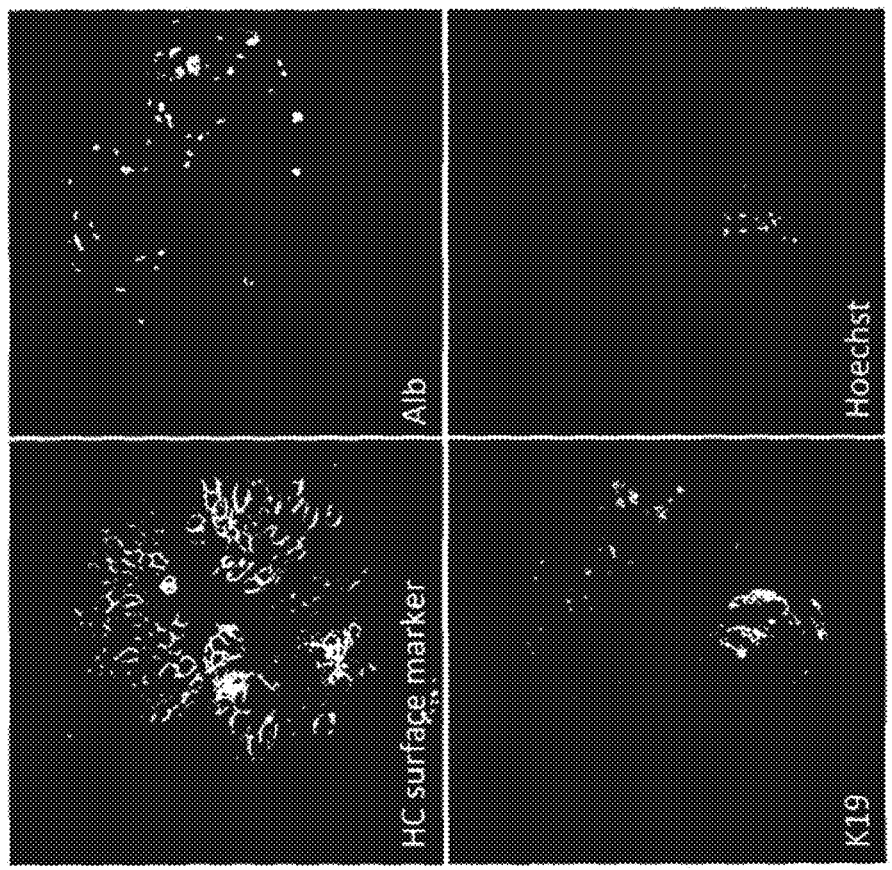
Fig. 10E  Staining for liver markers after 8 days of differentiation condition EADF Fig. 10F
Tamoxifen induced culture
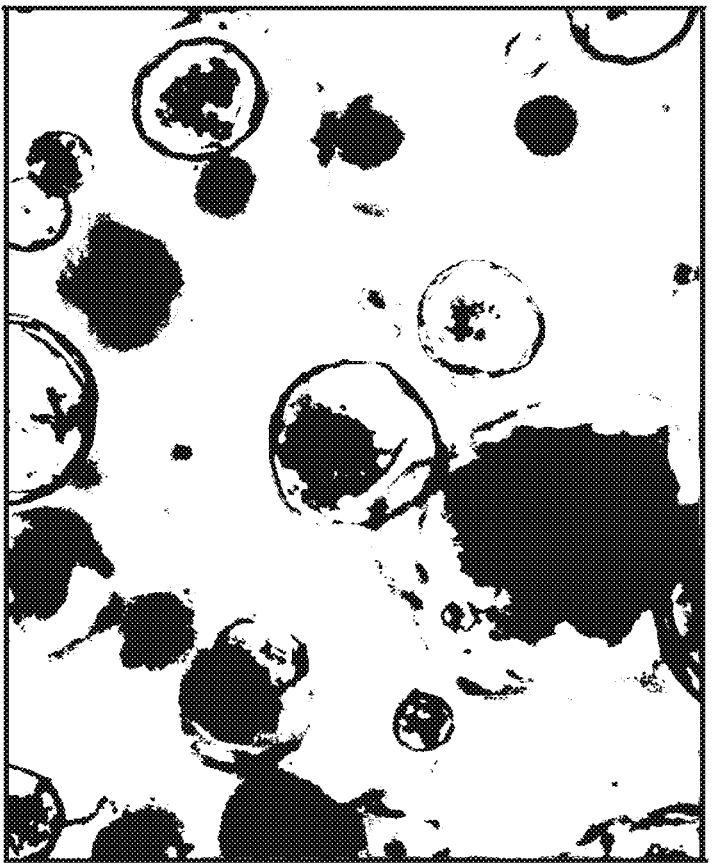
Control not induced with tamoxifen
Albcreert2LacZ derived organoids, (tamoxifen inducible system)

Fig. 11 - Human-derived liver cultures ERFHNic culture conditions
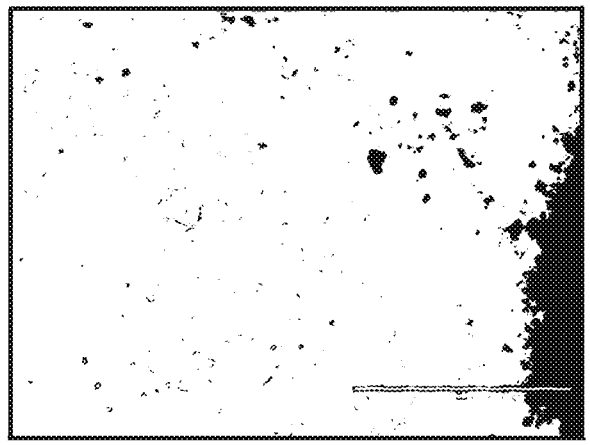
5 days after seeding 4x
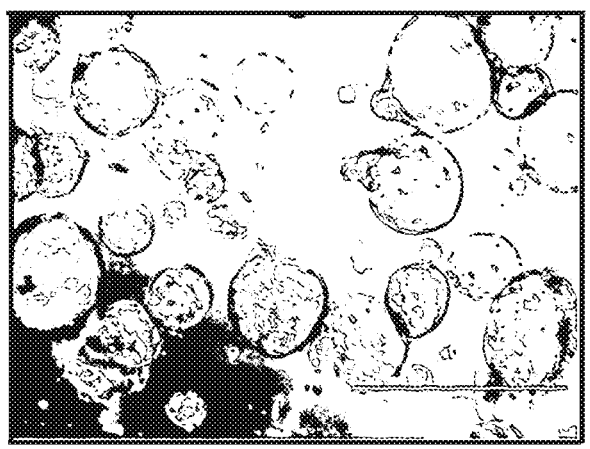
P1 (day 10) 4x
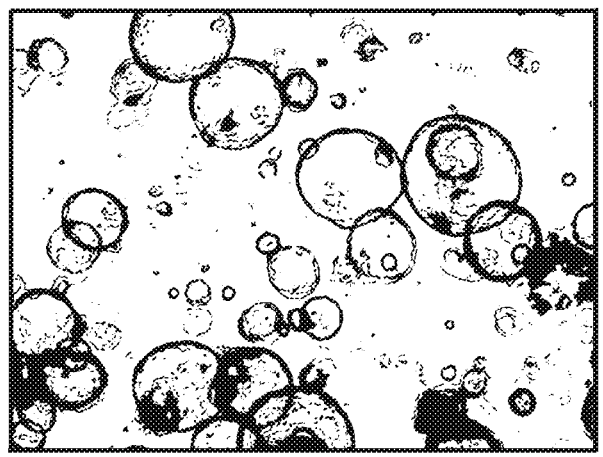
P2 (day 20) 4x

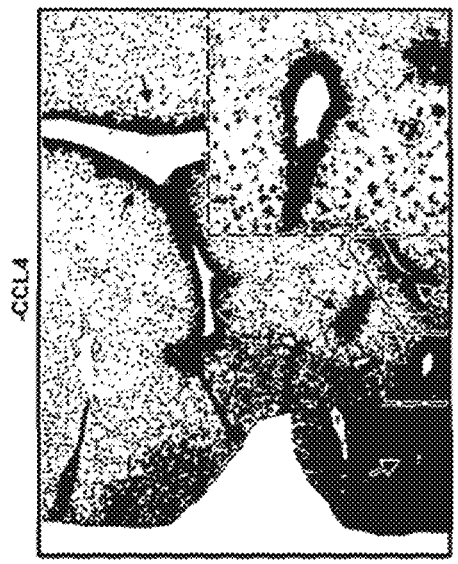
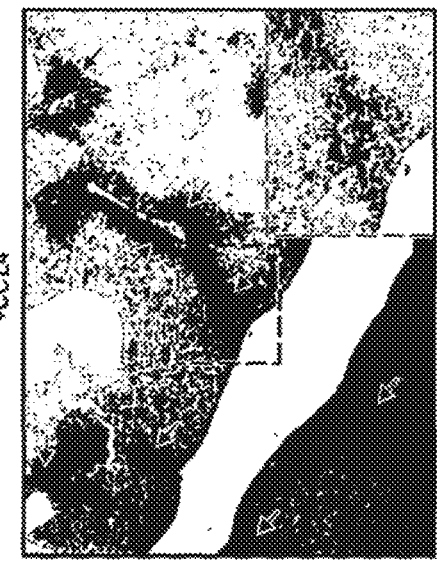
Fig. 12A
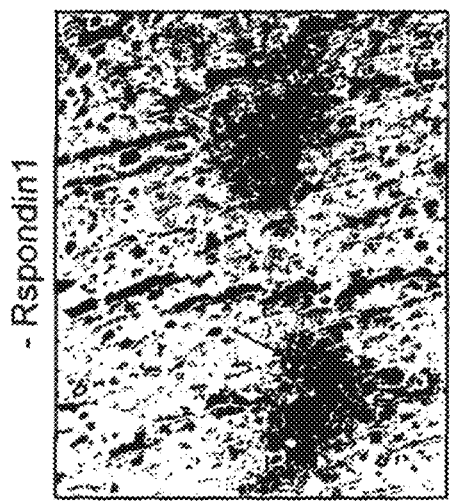
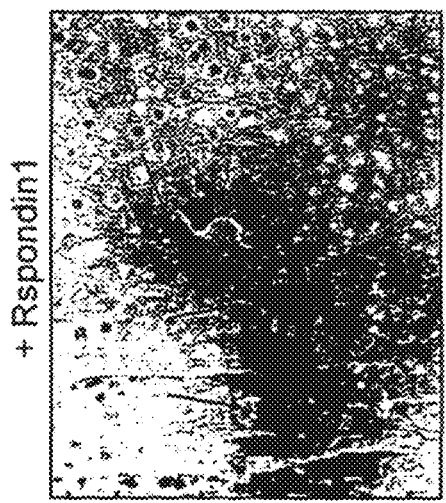
Fig. 12B

Fig. 14

Fig. 16C

| Ductal Markers | | Adult liver | Adult pancreas | Pancreas organoid | Liver organoid |
|---|---|---|---|---|---|
| ref\|Mus musculus leucine aminopeptidase 3 (Lap3), mRNA [N_024434] | Lap3 | 1826 | 922 | 3286 | 2855 |
| ref\|Mus musculus keratin 19 (Krt19), mRNA [NM_008471] | Krt19 | 302 | 566 | 76191 | 29904 |
| ref\|Mus musculus keratin 7 (Krt7), mRNA [NM_033073] | Krt7 | 237 | 369 | 147227 | 108352 |
| ref\|Mus musculus SRY-box containing gene 9 (Sox9), mRNA [NM_011448] | Sox9 | 235 | 185 | 2365 | 2492 |
| ref\|Mus musculus HNF1 homeobox B (Hnf1b), mRNA [NM_009330] | Hnf1b | 234 | 115 | 608 | 764 |
| ref\|Mus musculus one cut domain, family member 1 (Onecut1), mRNA [NM_008262] | Hnf6 | 1239 | 120 | 1297 | 1454 |
| Transcription Factors necessary for Ngn3 expression | | | | | |
| ref\|Mus musculus SRY-box containing gene 9 (Sox9), mRNA [NM_011448] | Sox9 | 235 | 185 | 2365 | 2492 |
| ref\|Mus musculus forkhead box A2 (Foxa2), mRNA [NM_010446] | Foxa2 | 8695 | 1415 | 12948 | 9579 |
| ref\|Mus musculus HNF1 homeobox B (Hnf1b), mRNA [NM_009330] | Hnf1b | 234 | 115 | 608 | 764 |
| ref\|Mus musculus one cut domain, family member 1 (Onecut1), mRNA [NM_008262] | Hnf6 | 1239 | 120 | 1297 | 1454 |
| Endocrine markers | | | | | |
| ref\|Mus musculus neurogenin 3 (Neurog3), mRNA [NM_009719] | Neurog3 | 226.5 | 108 | 110 | 118 |
| gb\|Mouse hepatocyte nuclear factor 1 (HFN-1) mRNA, complete cds. [M57966] | Hnf1a | 5709.5 | 653 | 4929 | 6185 |
| ref\|Mus musculus hepatic nuclear factor 4, alpha (Hnf4a), mRNA [NM_008261] | Hnf4a | 2347 | 90.5 | 385 | 404 |
| ref\|Mus musculus pancreatic and duodenal homeobox 1 (Pdx1), mRNA [NM_008814] | Pdx1 | 137 | 102 | 201.5 | 198.5 |
| ref\|Mus musculus neurogenic differentiation 1 (Neurod1), mRNA [NM_010894] | Neurod1 | 87 | 76 | 88 | 76.5 |
| ref\|Mus musculus ISL1 transcription factor, LIM/homeodomain (isl1), mRNA [NM_021459] | Isl1 | 82 | 88.5 | 93 | 239 |
| ref\|Mus musculus NK2 transcription factor related, locus 2 (Drosophila) (Nkx2-2), mRNA [NM_010919] | Nkx2-2 | 100 | 105 | 158 | 76 |
| ref\|Mus musculus NK2 transcription factor related, locus 6 (Drosophila) (Nkx2-6), mRNA [NM_010920] | Nkx2-6 | 158 | 93 | 94 | 99 |
| ref\|Mus musculus paired box gene 6 (Pax6), mRNA [NM_013627] | Pax6 | 157 | 86.5 | 100.5 | 114 |
| ref\|Mus musculus insulin II (Ins2), mRNA [NM_008387] | Ins2 | 195.5 | 113183 | 107.5 | 85.5 |
| ref\|Mus musculus solute carrier family 2 (facilitated glucose transporter), member 2 (Slc2a2), mRNA [NM_031197] | Slc2a2 | 1212.5 | 100 | 188 | 143 |
| ref\|Mus musculus pyruvate kinase liver and red blood cell (Pklr), transcript variant 1, mRNA [NM_013631] | Pklr | 237 | 124.5 | 388 | 186 |
| ref\|Mus musculus glucokinase (Gck), mRNA [NM_010292] | Gck | 1771 | 184 | 261 | 162 |

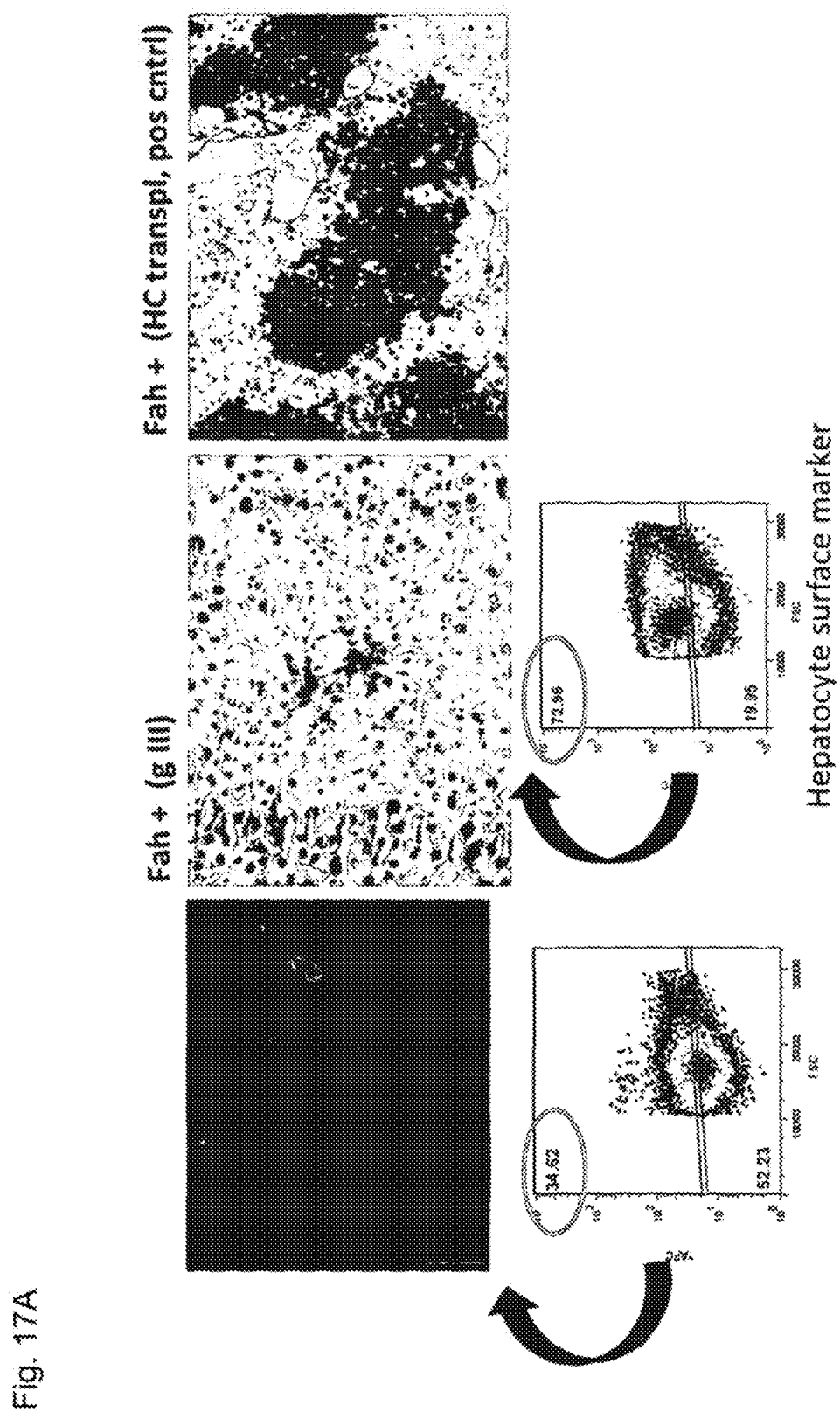

Flow Cytometry analysis for Hepatocyte (HC) surface marker on transplanted cells derived from Clone 1

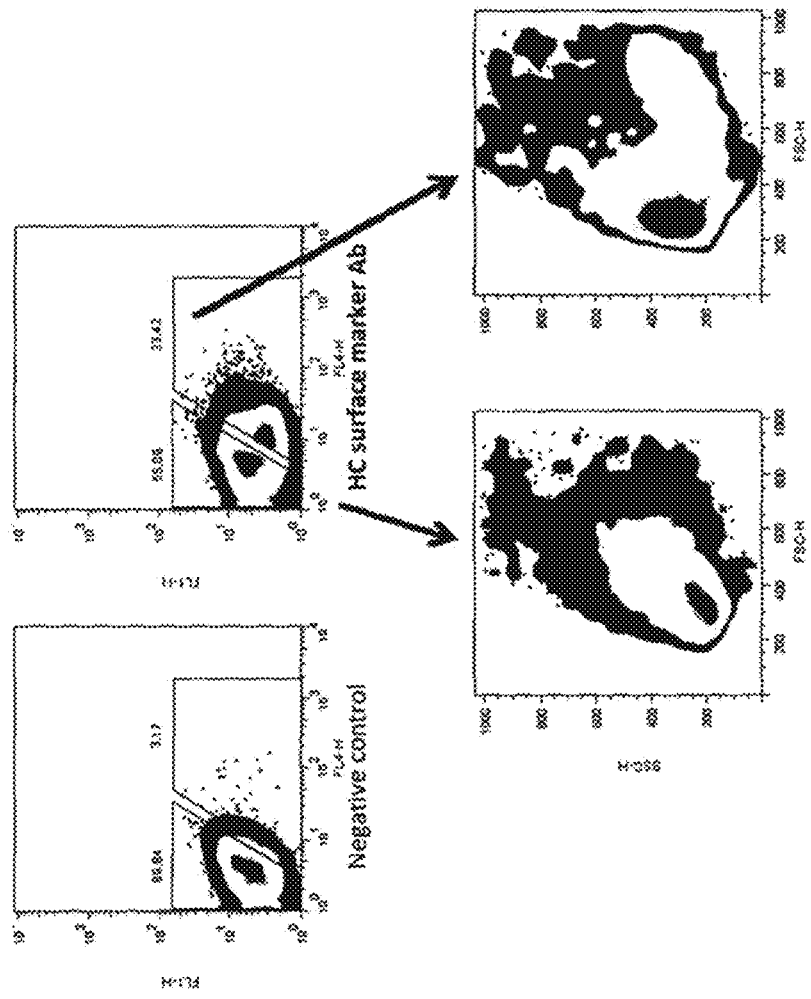

Fig. 18

| stem cell signature mouse liver | | liver/HC CG specific signature | | reprogramming genes | |
|---|---|---|---|---|---|
| positive for | negative for | positive for in expansion | negative for | positive | negative |
| lgr5 | lgr6 | Hnf1a | afp | Klf4 | Pou5f1 |
| lgr4 | | Hnf1b | Ins1 | Myc | Sox2 |
| epcam | | Hnf4a | Ins2 | | |
| Cd44 | | Hhex | Gcg | | |
| Tnfrsf19 | | Onecut1 | Ptf1a | | |
| Sox9 | | Onecut2 | Cela1 | | |
| Sp5 | | Prox1 | Cela2a | | |
| Cd24a | | Cdh1 | Cela3b | | |
| Prom1 | | Foxa2 | Neurod1 | | |
| Cdca7 | | Gata6 | Neurod2 | | |
| Elf3 | | Foxm1 | Neurog1 | | |
| | | Cebpa | Neurog2 | | |
| | | Cebpb | Neurog3 | | |
| | | Cebpd | Amy2a4 | | |
| | | Cebpg | Igf1r | | |
| | | Glul | Igf2 | | |
| | | Krt7 | Cd34 | | |
| | | Krt19 | | | |
| | | Met | | | |

Fig. 19A

*background cutoff >2.5fold (gMedian); dyeswap to Cy3/Cy5 (Cy3-samples, Cy5-reference RNA)

| Feature Number | Systematic Name | Description | Gene Name | ENRW pat1051 7708_1 | ER_pat 10511 7708_2 | EADF pat1051 7708_3 | liver tissue pat1051 Z514S506 7708_4 | | ENRW_pa t10511 gMedian Signal | ER_pan0 511 gMedia nSignal | EADF_pat 10511 gMedia nSignal | liver tissue_pa t10511 gMedia nSignal |
|---|---|---|---|---|---|---|---|---|---|---|---|---|
| Stem cell signature human liver | | | | | | | | | | | | |
| 40197 | NM_003667 | ref|Homo sapiens leucine-rich repeat-containing G protein-coupled receptor 5 (LGR5), mRNA [NM_003667] | LGR5 | 1.3710 | 1.5826 | 1.8852 | 1.1145 | | 85 | 82.5 | 83 | 80 |
| 40602 | NM_018490 | ref|Homo sapiens leucine-rich repeat-containing G protein-coupled receptor 4 (LGR4), mRNA [NM_018490] | LGR4 | 3.09978 | 3.5264 | 4.2412 | -3.2251 | | 1602 | 1684 | 2889 | 190.5 |
| 40067 | NM_002354 | ref|Homo sapiens tumor-associated calcium signal transducer 1 (TACSTD1), mRNA [NM_002354] | TACSTD1/E pcam | 0.8742 | 0.84495 | -1.5025 | -3.8418 | | 16341 | 23939 | 42144 | 110 |
| 18697 | NM_000610 | ref|Homo sapiens CD44 molecule (Indian blood group) (CD44), transcript variant 1, mRNA [NM_000610] | CD44 | 2.2553 | 2.3538 | | | | 10117 | 11624.5 | 25386.5 | 148.5 |
| 33576 | NM_018647 | ref|Homo sapiens tumor necrosis factor receptor superfamily, member 19 (TNFRSF19), transcript variant 1, mRNA [NM_018647] | TNFRSF19 | -0.0589 | 0.4409 | 1.5394 | -2.0445 | | 83 | 85.5 | 81 | 81 |
| 2604 | NM_000346 | ref|Homo sapiens SRY (sex determining region Y)-box 9 (campomelic dysplasia, autosomal sex-reversal) (SOX9), mRNA [NM_000346] | SOX9 | 3.2346 | 3.5288 | 1.95791 | 3.3653 | | 484 | 448.5 | 365 | 88 |
| 6370 | NM_001003 845 | ref|Homo sapiens Sp5 transcription factor (SP5), mRNA [NM_001003845] | SP5 | 3.2512 | 2.6437 | 0.8402 | -2.4236 | | 162 | 217.5 | 199 | 239.5 |
| 40879 | A_23_P6525 0 | gb|Homo sapiens CD24 signal transducer mRNA, complete cds and 3' region. [L33930] | CD24 | | | 1.95791 | | | 15141.5 | 17862 | 7049 | 125 |
| 1705 | NM_006017 | ref|Homo sapiens prominin 1 (PROM1), mRNA [NM_006017] | PROM1 | | | 2.4209 | -1.5356 | | 445 | 340 | 346 | 84 |

Fig. 19B

| | | | | | | | | | | |
|---|---|---|---|---|---|---|---|---|---|---|
| 43572 | NM_031942 | ref\|Homo sapiens cell division cycle associated 7 (CDCA7), transcript variant 1, mRNA [NM_031942] | CDCA7 | -2.4618 | -3.6148 | -7.7366 | -5.0979 | 476 | 218 | 87 | 83 |
| 1228 | NM_004433 | ref\|Homo sapiens E74-like factor 3 (ets domain transcription factor, epithelial-specific ) (ELF3), transcript variant 1, mRNA [NM_004433] | ELF3 | 3.3588 | 3.9163 | 4.2213 | 0.4499 | 6378.5 | 8700.5 | 14527 | 161 |
| Reprogramming genes | | | | | | | | | | | |
| 19017 | NM_004235 | ref\|Homo sapiens Kruppel-like factor 4 (gut) (KLF4), mRNA [NM_004235] | KLF4 | 0.3754 | 2.3397 | 1.9846 | -0.9306 | 291 | 1178.5 | 919 | 105 |
| 6084 | NM_002467 | ref\|Homo sapiens v-myc myelocytomatosis viral oncogene homolog (avian) (MYC), mRNA [NM_002467] | MYC | -1.1416 | -0.8254 | -3.3457 | -2.1032 | 3006 | 3896 | 871 | 323 |
| 11740 | NM_002701 | ref\|Homo sapiens POU class 5 homeobox 1 (POU5F1), transcript variant 1, mRNA [NM_002701] | POU5F1 | -3.9024 | -3.5281 | -3.8577 | -1.8681 | 1843 | 2251.5 | 2261 | 1173 |
| 34630 | NM_003106 | ref\|Homo sapiens SRY (sex determining region Y)-box 2 (SOX2), mRNA [NM_003106] | SOX2 | -4.0411 | -4.0509 | -4.3534 | -2.6317 | 131 | 131.5 | 129 | 96 |
| Liver/HC CG specific signature: positive for expansion | | | | | | | | | | | |
| 22258 | NM_000545 | ref\|Homo sapiens HNF1 homeobox A (HNF1A), mRNA [NM_000545] | HNF1A | 0.1593 | 0.4237 | 0.3115 | 2.1337 | 267.5 | 365.5 | 367.5 | 240 |
| 19971 | NM_000458 | ref\|Homo sapiens HNF1 homeobox B (HNF1B), mRNA [NM_000458] | HNF1B | 3.3524 | 3.3315 | 3.1792 | 0.0000 | 200.5 | 200 | 141 | 88 |
| 7418 | NM_000457 | ref\|Homo sapiens hepatocyte nuclear factor 4, alpha (HNF4A), transcript variant 2, mRNA [NM_000457] | HNF4A | -0.9981 | 1.7188 | 1.0493 | 2.0374 | 84.5 | 113.5 | 108 | 103 |
| 25738 | NM_002729 | ref\|Homo sapiens hematopoietically expressed homeobox (HHEX), mRNA [NM_002729] | HHEX | 0.8347 | 0.9290 | 1.4544 | 0.2789 | 1025 | 1263 | 1931 | 178 |
| 28360 | NM_004498 | ref\|Homo sapiens one cut homeobox 1 (ONECUT1), mRNA [NM_004498] | ONECUT1 | 0.5189 | 2.1647 | 2.9438 | 5.8053 | 120 | 211 | 327 | 387 |

Fig. 19C

| | | | | | | | | | | |
|---|---|---|---|---|---|---|---|---|---|---|
| 30379 | NM_004852 | ref\|Homo sapiens one cut homeobox 2 (ONECUT2) mRNA [NM_004852] | ONECUT2 | 3.4671 | 3.7373 | 3.5642 | 2.8300 | 4693 | 6965 | 6460 | 498 |
| 20882 | NM_002763 | ref\|Homo sapiens prospero homeobox 1 (PROX1), mRNA [NM_002763] | PROX1 | 2.4930 | 1.0227 | 1.1415 | 2.4817 | 98 | 98 | 97.5 | 101 |
| 12860 | NM_004360 | ref\|Homo sapiens cadherin 1, type 1, E-cadherin (epithelial) (CDH1), mRNA [NM_004360] | CDH1 | 3.3253 | 3.6614 | 4.1391 | 2.4935 | 10803 | 16648 | 25328 | 1076.5 |
| 33903 | NM_021784 | ref\|Homo sapiens forkhead box A2 (FOXA2), transcript variant 1, mRNA [NM_021784] | FOXA2 | 2.8637 | 3.2434 | 3.0108 | 2.6774 | 289.5 | 306 | 398 | 129.5 |
| 39806 | NM_005257 | ref\|Homo sapiens GATA binding protein 6 (GATA6), mRNA [NM_005257] | GATA6 | 3.0052 | 3.5536 | 3.8552 | 1.2789 | 1620 | 2038 | 3585 | 136 |
| 16668 | NM_202002 | ref\|Homo sapiens forkhead box M1 (FOXM1), transcript variant 1, mRNA [NM_202002] | FOXM1 | -1.9203 | -3.6288 | -5.0418 | -4.5112 | 329 | 156.5 | 117.5 | 94 |
| 9214 | NM_004364 | ref\|Homo sapiens CCAAT/enhancer binding protein (C/EBP), alpha (CEBPA), mRNA [NM_004364] | CEBPA | -0.9322 | 1.2903 | -0.0086 | 4.2303 | 304 | 1257 | 647 | 1586.5 |
| 14125 | NM_005194 | ref\|Homo sapiens CCAAT/enhancer binding protein (C/EBP), beta (CEBPB), mRNA [NM_005194] | CEBPB | -0.1111 | -0.2252 | 0.4127 | 2.5221 | 5257 | 5653.5 | 10124 | 5163.5 |
| 37458 | NM_005195 | ref\|Homo sapiens CCAAT/enhancer binding protein (C/EBP), delta (CEBPD), mRNA [NM_005195] | CEBPD | -0.1615 | 0.9115 | 0.4583 | 4.1610 | 1525 | 3232 | 2733 | 2661 |
| 145 | NM_001806 | ref\|Homo sapiens CCAAT/enhancer binding protein (C/EBP), gamma (CEBPG), mRNA [NM_001806] | CEBPG | 0.9187 | 2.0261 | 1.8780 | 0.7494 | 2185 | 4317.5 | 4980 | 364 |
| 41435 | NM_002065 | ref\|Homo sapiens glutamate-ammonia ligase (glutamine synthetase) (GLUL), transcript variant 1, mRNA [NM_002065] | GLUL | -0.1834 | 0.0758 | -0.8704 | 0.4736 | 1365.5 | 7538.5 | 876 | 311 |
| 30469 | NM_005556 | ref\|Homo sapiens keratin 7 (KRT7), mRNA [NM_005556] | KRT7 | 5.1396 | 4.8373 | 4.3723 | -0.0401 | 7538.5 | 4712 | 2627 | 96 |
| 13920 | NM_002276 | ref\|Homo sapiens keratin 19 (KRT19), mRNA [NM_002276] | KRT19 | 4.1830 | 3.7196 | 3.6914 | -2.4731 | 365708 | 424694 | 308350 | 1571 |
| 5427 | NM_000245 | ref\|Homo sapiens met proto-oncogene (hepatocyte growth factor receptor) (MET), mRNA [NM_000245] | MET | 1.3614 | 1.0945 | 1.2510 | -0.3692 | 7623.5 | 6839 | 8627 | 406 |

Fig. 19D

| | | | | | | | | | | | |
|---|---|---|---|---|---|---|---|---|---|---|---|
| Liver/HC CG specific signature: negative | | | | | | | | | | | |
| 16839 | NM_001134 | ref|Homo sapiens alpha-fetoprotein (AFP), mRNA [NM_001134] | AFP | -8.2863 | -8.4426 | -8.2926 | -5.5894 | 95 | 141 | 107 | 103 |
| 33640 | NM_002054 | ref|Homo sapiens glucagon (GCG), mRNA [NM_002054] | GCG | 0.0000 | 0.0000 | 0.0000 | 0.0000 | 85 | 90 | 88 | 78 |
| 34885 | NP233946 | gb|Homo sapiens bHLH transcription factor p48 mRNA, partial cds. [AF181999] | PTF1A | 0.1838 | 0.4898 | 0.6162 | 0.7839 | 105 | 111 | 112 | 93 |
| 40134 | NM_024019 | ref|Homo sapiens neurogenin 2 (NEUROG2), mRNA [NM_024019] | NEUROG2 | | | | | 73 | 79.5 | 81.5 | 75 |
| 5505 | NM_003875 | ref|Homo sapiens insulin-like growth factor 1 receptor (IGF1R), mRNA [NM_003875] | IGF1R | | | | | 78.5 | 81 | 82.5 | 78 |
| 5632 | NM_001773 | ref|Homo sapiens CD34 molecule (CD34), transcript variant 2, mRNA [NM_001773] | CD34 | | | | | 74 | 70 | 75 | 79 |
| Hepatocyte specific gene signature | | | | | | | | | | | |
| 991 | NM_000371 | ref|Homo sapiens transthyretin (prealbumin, amyloidosis type I) (TTR), mRNA [NM_000371] | TTR | -0.5692 | 0.0924 | 0.1884 | 9.0077 | 1243.5 | 1660 | 2331 | 107880 |
| 23323 | NM_000477 | ref|Homo sapiens albumin (ALB), mRNA [NM_000477] | ALB | -3.0821 | -2.9215 | -3.2544 | 6.3642 | 5970 | 10841 | 7266 | 306897 |
| 10807 | NM_000137 | ref|Homo sapiens fumarylacetoacetate hydrolase (fumarylacetoacetase) (FAH), mRNA [NM_000137] | FAH | -0.1297 | -0.5453 | -0.2095 | 2.2811 | 716 | 520 | 783 | 618 |
| 29558 | NM_000353 | ref|Homo sapiens tyrosine aminotransferase (TAT), nuclear gene encoding mitochondrial protein, mRNA [NM_000353] | TAT | 0.1829 | 0.3011 | -0.8291 | 6.6911 | 97 | 101 | 95 | 391.5 |
| 2423 | NM_000765 | ref|Homo sapiens cytochrome P450, family 3, subfamily A, polypeptide 7 (CYP3A7), mRNA [NM_000765] | CYP3A7 | 5.5611 | 7.1260 | 6.6750 | 8.9567 | 3649 | 10927 | 9853 | 5989 |

Fig. 19E

| | | | | | | | | | | |
|---|---|---|---|---|---|---|---|---|---|---|
| 1710 | NM_000039 | ref|Homo sapiens apolipoprotein A-1 (APOA1), mRNA [NM_000039] | APOA1 | -3.5478 | -2.8913 | -2.1400 | 5.2314 | 370 | 536 | 1014.5 | 24580 |
| 8511 | NM_002130 | ref|Homo sapiens 3-hydroxy-3-methylglutaryl-Coenzyme A synthase 1 (soluble) (HMGCS1), transcript variant 2, mRNA [NM_002130] | HMGCS1 | 1.9834 | 1.8579 | -1.2536 | 1.9013 | 1518 | 1248 | 264 | 271 |
| 2331 | NM_138711 | ref|Homo sapiens peroxisome proliferator-activated receptor gamma (PPARG), transcript variant 3, mRNA [NM_138711] | PPARG | 1.9376 | 3.5421 | 1.0259 | -0.9723 | 794 | 2225 | 489 | 102 |
| 42261 | NM_000767 | ref|Homo sapiens cytochrome P450, family 2, subfamily B, polypeptide 6 (CYP2B6), mRNA [NM_000767] | CYP2B6 | 3.1696 | 3.8429 | 3.7438 | 7.0424 | 691 | 835 | 1376 | 23535 |
| 40086 | NM_000772 | ref|Homo sapiens cytochrome P450, family 2, subfamily C, polypeptide 18 (CYP2C18), mRNA [NM_000772] | CYP2C18 | 7.6099 | 8.9559 | 7.5195 | 8.1267 | 441 | 938 | 458.5 | 231 |
| 18649 | NM_000771 | ref|Homo sapiens cytochrome P450, family 2, subfamily C, polypeptide 9 (CYP2C9), mRNA [NM_000771] | CYP2C9 | 7.4072 | 9.3744 | 7.5571 | 10.9138 | 371.5 | 1144 | 765 | 3195 |
| 1249 | NM_000775 | ref|Homo sapiens cytochrome P450, family 2, subfamily J, polypeptide 2 (CYP2J2), mRNA [NM_000775] | CYP2J2 | 2.6839 | 2.5692 | 2.5672 | 5.4100 | 839 | 595.5 | 802 | 682.5 |
| 37457 | NM_017460 | ref|Homo sapiens cytochrome P450, family 3, subfamily A, polypeptide 4 (CYP3A4), mRNA [NM_017460] | CYP3A4 | 6.0980 | 6.9956 | 7.3093 | 9.3567 | 430.5 | 1280 | 1142 | 496.5 |
| 33810 | ENST00000439761 | gb|Homo sapiens CYP3A5*3, allele CYP3A5*3, exon 4B and partial cds, alternatively spliced [AF355801] | CYP3A5 | -0.3739 | 0.1067 | 0.0937 | 1.4438 | 736 | 952.5 | 1172 | 403.5 |
| 2423 | NM_000765 | ref|Homo sapiens cytochrome P450, family 3, subfamily A, polypeptide 7 (CYP3A7), mRNA [NM_000765] | CYP3A7 | 5.5511 | 7.1260 | 6.6750 | 8.9567 | 3649 | 10927 | 9853 | 5989 |
| 14586 | NM_007253 | ref|Homo sapiens cytochrome P450, family 4, subfamily F, polypeptide 8 (CYP4F8), mRNA [NM_007253] | CYP4F8 | 2.7132 | 4.1535 | 2.5950 | 5.9628 | 686 | 2541.5 | 825.5 | 1176 |
| 14415 | NM_207352 | ref|Homo sapiens cytochrome P450, family 4, subfamily V, polypeptide 2 (CYP4V2), mRNA [NM_207352] | CYP4V2 | 2.9194 | 2.9333 | 2.7663 | 5.2822 | 853 | 995 | 923.5 | 822 |
| 29103 | NM_005505 | ref|Homo sapiens scavenger receptor class B, member 1 (SCARB1), transcript variant 1, mRNA [NM_005505] | SCARB1 | -0.6468 | -0.4215 | -1.0325 | 2.0324 | 14042 | 23763 | 13137 | 22012 |

SEQUENCE LISTING

<160> NUMBER OF SEQ ID NOS: 26

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
tggtcaaacg cctctccttg ctg                                          23

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
actgggccaa aatcccgccg                                              20

```
<210> SEQ ID NO 3
<211> LENGTH: 19
<212> TYPE: DNA
<213> ORGANISM: Artificial Sequence
<220> FEATURE:
<223> OTHER INFORMATION: primer

<400> SEQUENCE: 3
gaattaccaa gactccagg                                                    19

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
tgagacaata cttccggagg                                                   20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gtcctacaga ttgacaatgc                                                   20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
cacgctctgg atctgtgaca                                                   20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
gcgcagatga cagggcggaa                                                   20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
gtgccgtagc atgcgggagg                                                   20

<210> SEQ ID NO 9
<211> LENGTH: 20
<212> TYPE: DNA
<213> ORGANISM: Artificial Sequence
<220> FEATURE:
<223> OTHER INFORMATION: primer
```

```
<400> SEQUENCE: 9
agcgatcacg caacgtggca                                              20

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
ggcttcgctg ggacacagat cttt                                         24

<210> SEQ ID NO 11
<211> LENGTH: 18
<212> TYPE: DNA
<213> ORGANISM: Artificial Sequence
<220> FEATURE:
<223> OTHER INFORMATION: primer

<400> SEQUENCE: 11
ttcaacagat gcattacc                                                18

<210> SEQ ID NO 12
<211> LENGTH: 18
<212> TYPE: DNA
<213> ORGANISM: Artificial Sequence
<220> FEATURE:
<223> OTHER INFORMATION: primer

<400> SEQUENCE: 12
tctttgcccg cgatgatg                                                18

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
acgactggag cgcacgagac                                              20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
agggctggct gtggcagaga                                              20

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
tttggcagtg gctgaaaggc a                                            21

<210> SEQ ID NO 16
```

```
<211> LENGTH: 20
<212> TYPE: DNA
<213> ORGANISM: Artificial Sequence
<220> FEATURE:
<223> OTHER INFORMATION: primer

<400> SEQUENCE: 16
gggcccagga tccgctgact                                                  20

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
actccccgta gaaggcagcg a                                                21

<210> SEQ ID NO 18
<211> LENGTH: 22
<212> TYPE: DNA
<213> ORGANISM: Artificial Sequence
<220> FEATURE:
<223> OTHER INFORMATION: primer

<400> SEQUENCE: 18
tctttccagc catgcctcca ct                                               22

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
ggaaatgctt tgacacacat tc                                               22

<210> SEQ ID NO 20
<211> LENGTH: 23
<212> TYPE: DNA
<213> ORGANISM: Artificial Sequence
<220> FEATURE:
<223> OTHER INFORMATION: primer

<400> SEQUENCE: 20
ggaagtcatc aaggttatta taa                                              23

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
atggtcaaag tcctggatgc                                                  20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
```

```
aattcatgga acggggaaat                                              20

<210> SEQ ID NO 23
<211> LENGTH: 18
<212> TYPE: DNA
<213> ORGANISM: Artificial Sequence
<220> FEATURE:
<223> OTHER INFORMATION: primer

<400> SEQUENCE: 23
aagatcattg gcggaaag                                                18

<210> SEQ ID NO 24
<211> LENGTH: 19
<212> TYPE: DNA
<213> ORGANISM: Artificial Sequence
<220> FEATURE:
<223> OTHER INFORMATION: primer

<400> SEQUENCE: 24
gagtgctcag gatgttaag                                               19

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
aagcttgctg gtgaaaagga                                              20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
ttgcgctcat cttaggcttt                                              20
```

LIVER ORGANOID, USES THEREOF AND CULTURE METHOD FOR OBTAINING THEM

RELATED APPLICATIONS

This application is a continuation of U.S. application Ser. No. 13/812,614, filed Apr. 8, 2013, which is a national stage filing under 35 U.S.C. § 371 of international application PCT/IB2011/002167, filed Jul. 29, 2011, which was published under PCT Article 21(2) in English, and claims the benefit under 35 U.S.C. § 119(e) and the right of priority to U.S. Provisional Application Ser. No. 61/368,736, filed on Jul. 29, 2010 and U.S. Provisional Application Ser. No. 61/520,569, filed on Jun. 10, 2011, and which also claims priority to European Application Serial No. 10171265.1, filed on Jul. 29, 2010, the entire contents of each of which are incorporated by reference herein in their entireties.

FIELD OF THE INVENTION

The invention relates to a liver organoid, uses thereof and method for obtaining them.

BACKGROUND OF THE INVENTION

The basic architectural unit of the liver is the liver lobule. Each lobule consists of plates of hepatocytes lined by sinusoidal capillaries that radiate toward a central efferent vein. Liver lobules are roughly hexagonal with each of six corners demarcated by the presence of a portal triad (portal vein, bile duct, and hepatic artery). Although hepatocytes are the major parenchymal cell type of the liver they function in concert with cholangiocytes (biliary epithelial cells), endothelial cells, sinusoidal endothelial cells, Kupffer cells, natural killer cells and hepatic stellate cells. This complex architecture is crucial for hepatic function.

The existence of liver stem cells remains controversial. On one hand, tissue maintenance in the liver and liver regeneration upon certain types of injury, are not driven by stem cells but rather by division of the mature cells (hepatocytes or cholangyocytes). However, liver injury models in which hepatocyte proliferation has been inhibited also demonstrated the ability of the organ to regenerate in response to damage. This suggests that the liver can be considered as an organ with facultative stem cells.

So far, liver cultures derived from hepatocytes, or by differentiation of Embryonic Stem cells (ES) or induced Pluripotent Stem Cells, do not expand and self renew for longer periods.

Recently, in the small intestine, the gene Lgr5 was identified which is specifically expressed in cycling Crypt Base Columnar (CBC) cells, which are small cells that are interspersed between the Paneth cells (Barker et al., 2007. Nature 449: 1003-1007). Using a mouse in which a GFP/tamoxifen-inducible Cre recombinase cassette was integrated into the Lgr5 locus, it was shown by lineage tracing that the Lgr5$^+$ CBC cells constitute multipotent stem cells which generate all cell types of the epithelium even when assessed 14 months after Cre induction.

It was recently discovered that also Lgr6, besides Lgr5, but not Lgr4, is a unique marker for adult stem cells. While Lgr5 is expressed in stem cells of brain, kidney, liver, retina, stomach, intestine, pancreas, breast, hair follicle, ovary, adrenal medulla, and skin, Lgr6 is expressed in stem cells of brain, lung, breast, hair follicle, and skin.

Here we have developed a method to culture adult liver progenitors and to obtain a liver organoid that shows longer-lived maintenance, are able to differentiate to both, hepatocyte and cholangiocyte lineages and preserve the basic physiology of isolated liver fragments.

SUMMARY OF THE INVENTION

The invention provides a method for obtaining a liver organoid, wherein the method comprises culturing cells in a first "expansion" culture medium (also referred to herein as EM), preferably followed by culturing the cells in a second "differentiation" culture medium (also referred to herein as DM).

The liver organoid may be obtained by culturing a single Lgr5+ stem cell, a population of cells comprising at least one Lgr5+ stem cell, and/or a liver fragment. Herein, where "cells in/of the culture medium" are referred to, the meaning includes a single Lgr5+ stem cell, a population of cells comprising at least one Lgr5+ stem cell, and/or a liver fragment.

In one embodiment, the expansion medium comprises EGF, a Wnt agonist, FGF, and Nicotinamide. Preferably, the Wnt agonist is R-spondin 1 and so the expansion medium is referred to as "ERFNic". A particularly preferred expansion medium additionally comprises HGF and is referred to as "ERFHNic".

In one embodiment, the differentiation medium comprises EGF, a TGF-beta inhibitor, FGF and a Notch inhibitor. In one embodiment, the TGF-beta inhibitor is A83-01 and/or the Notch inhibitor is DAPT. This differentiation medium is referred to herein as "EAFD" and is a preferred differentiation medium of the invention. FGF may optionally be replaced by HGF or alternatively both FGF and HGF may be present or absent in the differentiation medium. Dexamethasone may also be added.

In a preferred embodiment, the cells may initially be cultured in an expansion medium that additionally contains Wnt and Noggin, for example an "ENRW" medium containing EGF, Noggin, R-spondin and Wnt, and optionally FGF, HGF and Nicotinamide. The inventors have found that this medium is optimum for stimulating initial expansion of cells for the first few days. Therefore, this first expansion medium is sometimes referred to herein as EM1. In some embodiments, the Wnt and Noggin are removed after approximately 1 day, 2 days, 3 days, 4 days, 5 days, 6 days, 7 days or more, for example 2 week, 1 month, 2, 3, 4, 5, 6, 7, 8, 9, 10, 11, 12 months or more, 14 months or more. The cells may then be expanded in an expansion medium of the invention, as described above that does not contain Wnt or Noggin. This second expansion medium is sometimes referred to herein as EM2. In some embodiments, the cells are cultured in EM2 for approximately 1 day, 2 days, 3 days, 4 days, 5 days, 6 days, 7 days or a longer time period, such as 3, 4, 5, 10, 20 or more weeks. The culture medium may then be changed to an optimised differentiation medium, as described above, that contains a TGF-beta inhibitor and a Notch inhibitor. Typically, the differentiation medium does not contain a Wnt agonist, R-spondin or Nicotinamide. This encourages the differentiation of the cells towards mature hepatocytes and cholangyocytes. These cells are suitable for transplantation into humans or animals.

The invention also provides a liver organoid. The present application describes the first time that liver organoids have been grown ex vivo.

DESCRIPTION OF THE INVENTION

In a first aspect, the invention provides a method for obtaining and/or culturing a liver fragment or a liver organoid, wherein said method comprises:

culturing epithelial stem cells, and/or isolated tissue fragments comprising said epithelial stem cells in contact with an extracellular matrix in the presence of a medium, the medium comprising a basal medium for animal or human cells to which is added: Epidermal Growth Factor, an FGF able to bind to FGFR2 or FGFR4, preferably FGF10 as a mitogenic growth factor, Nicotinamide, and preferably, a Wnt agonist, preferably R-spondin 1, R-spondin 2, R-spondin 3 or R-spondin 4 and/or Wnt-3a. Preferably, HGF is also added.

For example, in one embodiment, the invention provides a method for obtaining and/or culturing a liver fragment or a liver organoid, wherein said method comprises:

culturing epithelial stem cells, and/or isolated tissue fragments comprising said epithelial stem cells in contact with an extracellular matrix in the presence of a medium, the medium comprising a basal medium for animal or human cells to which is added a BMP inhibitor, a Wnt agonist, Epidermal Growth Factor, a FGF able to bind to FGFR2 or FGFR4, preferably FGF10 and HGF as mitogenic growth factors, gastrin, Nicotinamide, B27, N2 and N-Acetylcysteine.

It has surprisingly been found by the present inventors that a method of the invention allows culturing of epithelial stem cells, and/or isolated fragments from the liver comprising said stem cells, while preserving the presence of stem cells that retain an undifferentiated phenotype and self-maintenance capabilities. Even more surprising was the observation that a method of the invention allows the outgrowth of a single, isolated epithelial stem cell into a liver organoid in the absence of a stem cell niche.

Stem cells are found in many organs of adult humans and mice. Although there may be great variation in the exact characteristics of adult stem cells in individual tissues, adult stem cells share at least the following characteristics: they retain an undifferentiated phenotype; their offspring can differentiate towards all lineages present in the pertinent tissue; they retain self-maintenance capabilities throughout life; and they are able to regenerate the pertinent tissue after injury. Stem cells reside in a specialized location, the stem cell niche, which supplies the appropriate cell-cell contacts and signals for maintenance of said stem cell population.

Epithelial stem cells are able to form the distinct cell types of which the epithelium is composed. Some epithelia, such as skin or intestine, show rapid cell turnover, indicating that the residing stem cells must be continuously proliferating. Other epithelia, such as the liver or pancreas, show a very slow turnover under normal conditions.

The isolation of liver epithelial stem cells may be carried out by a number of different protocols. Although the inventors do not wish to be bound by any particular theory, it is hypothesised herein that a population of stem cells exists within the liver that upon tissue injury, is responsible for liver regeneration. It is thought that the cell population responsible for this injury-responsive regeneration expresses the marker Lgr5 when activated.

By injecting Lgr5-LacZ knock-in mice with the hepatotoxic compound CC14 to simulate liver damage, the inventors have demonstrated for the first time that liver damage induces Lgr5 expression in the liver at sites of active regeneration (see example 4). The inventors have also shown that injection of the Wnt agonist R-spondin causes upregulation of Wnt signalling expression in the liver ducts. Although the inventors do not wish to be bound by any particular theory, it is hypothesised herein that regenerative stem cells/progenitors may be activated by Wnt signalling after liver injury. The Lgr5 positive cells may then be isolated from the liver/liver fragment, if required, as described herein. Thus the invention provides a method for obtaining/isolating Lgr5+ cells from the liver comprising inducing liver injury or by stimulating Wnt signalling, for example with R-spondin. This is useful because in some embodiments Lgr5+ cells are the starting point for obtaining liver organoids in vitro (although the use of a culture medium of the invention allows generation of a Lgr5+ cell by adding a Wnt agonist such as R-spondin and so it is not essential to obtain an Lgr5+ cell from the liver in order to practice the present invention). Lgr5+ cells obtained by this method are also provided. In some embodiments, such cells preferably do not express markers of stellate cells, for example SMA. Instead, such cells preferably express one or more liver progenitor markers or stem cell markers such as Sox9. Preferably, the expression of one or more liver progenitor markers or stem cell markers such as Sox9 is upregulated in said cells compared to adult liver.

The invention also provides a method for regenerating the liver comprising stimulating Wnt signalling. Such a method may be useful in the treatment of liver disorders. The induction of Lgr5 expression in liver cells by injury or by stimulating Wnt signalling may be carried out in vivo, ex vivo in an isolated liver, or in vitro in a liver fragment or population of liver cells. In embodiments in which the induction of Lgr5 expression is carried out ex vivo or in vitro, the Lgr5 positive cells may be administered to a patient in need thereof by any suitable means, for example, by injection or by implantation. In some embodiments, implanted cells are contained in biocompatible matrix. In some embodiments, the cells are expanded ex vivo prior to being used in therapy.

In a preferred method of the invention, said epithelial stem cells are isolated from a liver fragment or a liver biliary duct, more preferably from biliary duct tissue.

Methods for the isolation of bile duct tissue are known to those of skill in the art. For example, biliary duct may be isolated from a liver as described in the examples enclosed herein. Briefly, an adult liver tissue may be washed in a cold (4-10° C.) culture medium, preferably Advanced-DMEM/F12 (Invitrogen) and then, the tissue can be chopped into pieces of around 5 mm and further washed with cold dissociation buffer (collagenase, dispase, FBS in DMEM media). The tissue fragments are preferably incubated with the dissociation buffer for about 2 h at about 37° C. Then, the tissue fragments can be vigorously suspended in 10 ml of cold (4-10° C.) isolation buffer with a 10 ml pipette. The first supernatant containing dead cells is preferably discarded and the sediment preferably suspended with dissociation buffer (e.g. 10-15 ml). After further vigorous suspension of the tissue fragments the supernatant is enriched in biliary ducts. A suspension containing biliary ducts can in this way be obtained and biliary ducts are collected under the microscope and retained in cold media (DMEM+5-10% FBS). This procedure may be repeated until at least 10-20 biliary ducts/well are collected. Then, the isolated biliary ducts may be precipitated. Isolated bile ducts are preferably seeded in 50 ul of MATRIGEL™ at an approximate ratio of 20 biliary ducts/well.

In contrast to mature hepatocytes, which grow to confluence for a short period of time, before dying, liver epithelial stem cells isolated according to the invention are self-renewing and grow indefinitely. It has been found that the self-renewing population of cells are those which are capable of expressing Lgr5 on their surface. Lgr5 negative cells do not self-renew. The term "self-renewing" should be understood to represent the capacity of a cell to reproduce itself whilst maintaining the original proliferation and differentiation properties of cells of the invention. Such cells proliferate by dividing to form clones, which further divide into clones and therefore expand the size of the cell population without the need for external intervention, without evolving into cells with a more restricted differentiation potential.

A preferred method is based on the fact that liver stem cells according to the invention express Lgr5 and/or Lgr6 on their surface; these proteins belong to the large G protein-coupled receptor (GPCR) superfamily (see, for example, WO2009/022907, the contents of which are incorporated herein in their entirety). The Lgr subfamily is unique in carrying a large leucine-rich ectodomain important for ligand binding. A preferred method therefore comprises preparing a cell suspension from said epithelial tissue as described above, contacting said cell suspension with an Lgr5 and/or 6 binding compound (such as an antibody), isolating the Lgr5 and/or 6 binding compound, and isolating the stem cells from said binding compound.

It is preferred that a single cell suspension comprising the epithelial stem cells is mechanically generated from the isolated biliary duct. Small organoid fragments generated in this way by mechanical disruption are preferably split at a ratio of approximately 1:6. If necessary, such fragments can be incubated for a short time (only 2 or 3 minutes) in trypsin at a dilution of approximately 1:2. It has been found that at this stage epithelial stem cells treated with trypsin yielded rather low survival rates: if the cells are split into individual cells, then only those expressing Lgr5 survive. This fraction is rather small (approximately 12% of the total cell population).

Preferred Lgr5 and/or 6 binding compounds comprise antibodies, such as monoclonal antibodies that specifically recognize and bind to the extracellular domain of either Lgr5 or Lgr6, such as monoclonal antibodies including mouse and rat monoclonal antibodies (see, for example, WO2010/016766, the contents of which are incorporated herein in their entirety). Using such an antibody, Lgr5 and/or Lgr6-expressing stem cells can be isolated, for example with the aid of magnetic beads or through fluorescence-activated cell sorting, as is clear to a skilled person. Using a method of the invention, it is possible to isolate one single Lgr5 and/or Lgr6 expressing cell and to apply a method of the invention to it. A liver organoid may therefore be derived from one single cell.

Stem Cell Niche

Isolated stem cells are preferably cultured in a microenvironment that mimics at least in part a cellular niche in which said stem cells naturally reside. This cellular niche may be mimicked by culturing said stem cells in the presence of biomaterials, such as matrices, scaffolds, and culture substrates that represent key regulatory signals controlling stem cell fate. Such biomaterials comprise natural, semi-synthetic and synthetic biomaterials, and/or mixtures thereof. A scaffold provides a two-dimensional or three dimensional network. Suitable synthetic materials for such a scaffold comprise polymers selected from porous solids, nanofibers, and hydrogels such as, for example, peptides including self-assembling peptides, hydrogels composed of polyethylene glycol phosphate, polyethylene glycol fumarate, polyacrylamide, polyhydroxyethyl methacrylate, polycellulose acetate, and/or co-polymers thereof (see, for example, Saha et al., 2007. Curr Opin Chem Biol. 11(4): 381-387; Saha et al., 2008. Biophysical Journal 95: 4426-4438; Little et al., 2008. Chem. Rev 108, 1787-1796). As is known to a skilled person, the mechanical properties such as, for example, the elasticity of the scaffold influences proliferation, differentiation and migration of stem cells. A preferred scaffold comprises biodegradable (co)polymers that are replaced by natural occurring components after transplantation in a subject, for example to promote tissue regeneration and/or wound healing. It is furthermore preferred that said scaffold does not substantially induce an immunogenic response after transplantation in a subject. Said scaffold is supplemented with natural, semi-synthetic or synthetic ligands, which provide the signals that are required for proliferation and/or differentiation, and/or migration of stem cells. In a preferred embodiment, said ligands comprise defined amino acid fragments. Examples of said synthetic polymers comprise Pluronic® F127 block copolymer surfactant (BASF), and Ethisorb® (Johnson and Johnson).

A cellular niche is in part determined by the stem cells and surrounding cells, and the extracellular matrix (ECM) that is produced by the cells in said niche. In a preferred method of the invention, isolated liver fragments or isolated biliary duct or epithelial stem cells are attached to an ECM. ECM is composed of a variety of polysaccharides, water, elastin, and glycoproteins, wherein the glycoproteins comprise collagen, entactin (nidogen), fibronectin, and laminin. ECM is secreted by connective tissue cells. Different types of ECM are known, comprising different compositions including different types of glycoproteins and/or different combination of glycoproteins. Said ECM can be provided by culturing ECM-producing cells, such as for example fibroblast cells, in a receptacle, prior to the removal of these cells and the addition of isolated liver fragments or isolated biliary duct or isolated epithelial stem cells. Examples of extracellular matrix-producing cells are chondrocytes, producing mainly collagen and proteoglycans, fibroblast cells, producing mainly type IV collagen, laminin, interstitial procollagens, and fibronectin, and colonic myofibroblasts producing mainly collagens (type I, III, and V), chondroitin sulfate proteoglycan, hyaluronic acid, fibronectin, and tenascin-C. Alternatively, said ECM is commercially provided. Examples of commercially available extracellular matrices are extracellular matrix proteins (Invitrogen) and basement membrane preparations from Engelbreth-Holm-Swarm (EHS) mouse sarcoma cells (e.g. MATRIGEL™ (BD Biosciences)). A synthetic extracellular matrix material, such as ProNectin (Sigma Z378666) may be used. Mixtures of extracellular matrix materials may be used, if desired. The use of an ECM for culturing stem cells enhanced long-term survival of the stem cells and the continued presence of undifferentiated stem cells. In the absence of an ECM, stem cell cultures could not be cultured for longer periods and no continued presence of undifferentiated stem cells was observed. In addition, the presence of an ECM allowed culturing of three-dimensional tissue organoids, which could not be cultured in the absence of an ECM. The extracellular matrix material will normally be coated onto a cell culture vessel, but may (in addition or alternatively) be supplied in solution. A fibronectin solution of about 1 mg/ml may be used to coat a cell culture vessel, or between about 1 µg/cm$^2$ to about 250 µg/cm$^2$, or at about 1 µg/cm$^2$ to about 150 µg/cm$^2$. In some embodiments, a cell culture vessel is coated with fibronectin at between 8 µg/cm$^2$ and 125 µg/cm$^2$.

A preferred ECM for use in a method of the invention comprises at least two distinct glycoproteins, such as two different types of collagen or a collagen and laminin. The ECM can be a synthetic hydrogel extracellular matrix or a naturally occurring ECM. A further preferred ECM is provided by MATRIGEL™ (BD Biosciences), which comprises laminin, entactin, and collagen IV.

The compositions of the invention may comprise serum, or may be serum-free and/or serum-replacement free, as described elsewhere herein. Culture media and cell preparations are preferably GMP processes in line with standards required by the FDA for biologics products and to ensure product consistency.

Culture Media

A cell culture medium that is used in a method of the invention comprises any suitable cell culture medium, subject to the limitations provided herein. Cell culture media typically contain a large number of ingredients, which are necessary to support maintenance of the cultured cells. Suitable combinations of ingredients can readily be formulated by the skilled person, taking into account the following disclosure. A culture medium according to the invention will generally be a nutrient solution comprising standard cell culture ingredients, such as amino acids, vitamins, inorganic salts, a carbon energy source, and a buffer, as described in more detail in the literature and below.

A culture medium of the invention will normally be formulated in deionized, distilled water. A culture medium of the invention will typically be sterilized prior to use to prevent contamination, e.g. by ultraviolet light, heating, irradiation or filtration. The culture medium may be frozen (e.g. at −20° C. or −80° C.) for storage or transport. The medium may contain one or more antibiotics to prevent contamination. The medium may have an endotoxin content of less that 0.1 endotoxin units per ml, or may have an endotoxin content less than 0.05 endotoxin units per ml. Methods for determining the endotoxin content of culture media are known in the art.

A preferred cell culture medium is a defined synthetic medium that is buffered at a pH of 7.4 (preferably with a pH 7.2-7.6 or at least 7.2 and not higher than 7.6) with a carbonate-based buffer, while the cells are cultured in an atmosphere comprising between 5% and 10% CO2, or at least 5% and not more than 10% CO2, preferably 5% CO2.

The skilled person will understand from common general knowledge the types of culture media that might be used for as the basal medium in the cell culture mediums of the invention. Potentially suitable cell culture media are available commercially, and include, but are not limited to, Dulbecco's Modified Eagle Media (DMEM), Minimal Essential Medium (MEM), Knockout-DMEM (KO-DMEM), Glasgow Minimal Essential Medium (G-MEM), Basal Medium Eagle (BME), DMEM/Ham's F12, Advanced DMEM/Ham's F12, Iscove's Modified Dulbecco's Media and Minimal Essential Media (MEM), Ham's F-10, Ham's F-12, Medium 199, and RPMI 1640 Media.

A preferred cell culture medium is selected from DMEM/F12 and RPMI 1640 supplemented with glutamine, insulin, Penicillin/streptomycin and transferrin. In a further preferred embodiment, Advanced DMEM/F12 or Advanced RPMI is used, which is optimized for serum free culture and already includes insulin. In this case, said Advanced DMEM/F12 or Advanced RPMI medium is preferably supplemented with glutamine and Penicillin/streptomycin.

In some embodiments, the basal medium comprises Advanced DMEM F12, hepes, penicillin/streptomycin, Glutamin, NAcetyl Cystein, B27, N2 and Gastrin. In some embodiments, culture is initiated with a basal medium comprising N2 and Gastrin and penicillin/streptomycin but these are later withdrawn. For example, in some embodiments, N2 and Gastrin and penicillin/streptomycin are present in an EM1 medium of the invention but not in an EM2 or DM. For example, in some embodiments, N2 and Gastrin and penicillin/streptomycin are present in an EM1 and EM2 medium of the invention but not in a DM. In particularly preferred embodiments, the basal medium is Advanced DMEM/F12 or a DMEM variant supplemented with penicillin/streptomycin, N2, B27, glutamine and gastrin.

In preferred embodiments, the basal medium comprises Gastrin. In some embodiments, the basal medium also comprises NAc and/or B27.

It is furthermore preferred that said cell culture medium is supplemented with a purified, natural, semi-synthetic and/or synthetic growth factor and does not comprise an undefined component such as fetal bovine serum or fetal calf serum. Various different serum replacement formulations are commercially available and are known to the skilled person. Where a serum replacement is used, it may be used at between about 1% and about 30% by volume of the medium, according to conventional techniques.

Expansion Medium (EM2):

In one aspect of the present invention there is provided a cell culture medium which comprises or consists of a basal medium for animal or human cells to which is added: Epidermal Growth Factor, an FGF able to bind to FGFR2 or FGFR4, preferably FGF10 as a mitogenic growth factor, Nicotinamide, and preferably, a Wnt agonist, preferably R-spondin 1. This medium is referred to as EM2.

Preferably, the Wnt agonist is R-spondin 1. A medium comprising EGF, R-spondin 1, FGF and Nicotinamide is referred to herein as ERFNic.

In some embodiments, the EM2 medium does not comprise noggin, and more preferably does not comprise a BMP-inhibitor. In some embodiments, the EM2 medium does not comprise Wnt, for example Wnt-3a.

In some embodiments, HGF is present in addition to FGF. A preferred medium comprising HGF in addition to FGF is ERFHNic (EGF+R-spondin (preferably R-spondin1)+FGF (preferably FGF10)+HGF+Nicotinamide). The inventors have found that the ERFHNic medium is the optimal medium for long-term expansion of cells. In the absence of HGF, cells did not remain viable in culture for longer than three months. Further, in the absence of HGF, after 10 passages, cells showed a growth disadvantage compared to cells cultured in the presence of HGF as evidenced by a lower proliferation ratio. In particular, after 15 passages, the cells were not growing organoids at the same speed ratio in the absence of HGF as in the presence of HGF. Thus, HGF was found to be essential for maintaining a good proliferation rate during long-term culture. Thus the invention provides the use of an ERFHNic medium of the invention for culturing cells for at least 2 weeks, at least 1 month, at least 2 months, more preferably at least 3, at least 4, at least 5, at least 6, at least 7, at least 8, at least 9, at least 10, at least 15, at least 20, at least 24, at least 25, at least 30 or more months, for example 3 or more years. In practice, some embodiments of the invention comprise the use of E2 for around 20-30 passages of the cells. For example, the cells may be split 20-30 times, generally once a week. Preferably the cells will expand at a rate of about 4 fold per week or two population doublings a week. The invention further provides the use of an ERFHNic medium of the invention for culturing cells for at least 10 passages, for example, at least 11, at least 12, at least 15, at least 20, at least 25, at least 30, at least 40, at least 50, at least 60 passages or for between 15-35 passages, for example approximately 20-30 passages. In some embodiments, a TGF-beta inhibitor such as A83-01 is additionally present in the EM2 medium. This is particularly useful when human cells or organoids are being cultured. In some embodiments, the A83-01 is present at a concentration of between 400-600 nM, for example 450-550 nM, 470-530 nM or approximately 500 nM. In embodiments in which a TGF-beta inhibitor is present in EM2, a Notch inhibitor is preferably not present.

Expansion Medium (EM1):

In one aspect, the invention provides a cell culture medium comprising or consisting of a basal medium for animal or human cells to which is added EGF, a BMP inhibitor, R-spondin and Wnt. Preferably, the BMP inhibitor is Noggin and the EM1 medium is termed "ENRW" (EGF, Noggin, R-spondin and Wnt). This medium is referred to as EM1. The inventors have found that a medium containing Wnt and Noggin is ideal for stimulating initial expansion of cells. Thus, in some embodiments, the EM1 medium is used for just 1 passage or 1 week but it is also envisaegd that EM1 medium can be used for around a year because it is not harmful for the cells. Thus, in some embodiments, an EM1 medium is used for culturing cells from day 0 to day 10, for example from days 0-7, days 0-6, days 0-5, days 0-4, days 0-3, days 0-2, days 0-1, wherein day 0 is the day that the cells are isolated from their tissue of origin and day 1 is the subsequent day or is used for 1 or more weeks for example 2, 3, 4 or more weeks or 1, 2, 3, 4, 5, 6, 7, 8, 9, 10, 11, 12 or more months. In some embodiments, the EM1 medium is used only for the first day or first two days of culture. In some embodiments, EM1 medium is used for 1 or more passages, for example, 1, 2, 3, 4, 5, 6, 7, 8, 9, 10, 15, 20, 25, 30 or more passages, for example, 20-30 passages. In some embodiments, the EM1 medium is used subsequent to a freezing step or any other transportation step involving a medium or temperature change that does not combine with optimal growth.

The EM1 medium is supplemented with one or more of the compounds selected from the group consisting of FGF, HGF, Nicotinamide, gastrin, B27, N-acetylcystein and N2. In the case of starting the cultures from a frozen stock or from a single cell, the EM1 media is preferably supplemented with a ROCK inhibitor. Y27632 is the preferred ROCK inhibitor for use in the invention.

Thus, in one embodiment there is provided a cell culture medium which comprises or consists of a basal medium for animal or human cells to which is added: Epidermal Growth Factor, an FGF able to bind to FGFR2 or FGFR4, preferably FGF10 and HGF as mitogenic growth factors, gastrin, Nicotinamide, B27, N2 and N-Acetylcysteine, and preferably;

a BMP inhibitor, preferably Noggin; and a Wnt agonist, preferably R-spondin 1 and/or Wnt-3a.

B27 (Invitrogen), N-Acetylcysteine (Sigma) and N2 (Invitrogen), Gastrin (Sigma) and Nicotinamide (Sigma) are also added to the medium defined above and are believed to stimulate proliferation of the cells. In the context of the invention, Nicotinamide is also referred to herein as "Nic".

'N2 Supplement' is available from Invitrogen, Carlsbad, Calif.; www.invitrogen.com; catalog no. 17502-048; and from PAA Laboratories GmbH, Pasching, Austria; www.paa.com; catalog no. F005-004; Bottenstein & Sato, PNAS, 76(1):514-517, 1979. N2 Supplement is supplied by PAA Laboratories GmbH as a 100× liquid concentrate, containing 500 µg/ml human transferrin, 500 µg/ml bovine insulin, 0.63 µg/ml progesterone, 1611 µg/ml putrescine, and 0.52 µg/ml sodium selenite. N2 Supplement may be added to a culture medium as a concentrate or diluted before addition to a culture medium. It may be used at a 1× final concentration or at other final concentrations. Use of N2 Supplement is a convenient way to incorporate transferrin, insulin, progesterone, putrescine and sodium selenite into a culture medium of the invention.

'B27 Supplement' (available from Invitrogen, Carlsbad, Calif.; www.invitrogen.com; currently catalog no. 17504-044; and from PAA Laboratories GmbH, Pasching, Austria; www.paa.com; catalog no. F01-002; Brewer et al., J Neurosci Res., 35(5):567-76, 1993) may be used to formulate a culture medium that comprises biotin, cholesterol, linoleic acid, linolenic acid, progesterone, putrescine, retinol, retinyl acetate, sodium selenite, tri-iodothyronine (T3), DL-alpha tocopherol (vitamin E), albumin, insulin and transferrin. B27 Supplement is supplied by PAA Laboratories GmbH as a liquid 50× concentrate, containing amongst other ingredients biotin, cholesterol, linoleic acid, linolenic acid, progesterone, putrescine, retinol, retinyl acetate, sodium selenite, tri-iodothyronine (T3), DL-alpha tocopherol (vitamin E), albumin, insulin and transferrin. Of these ingredients at least linolenic acid, retinol, retinyl acetate and tri-iodothyronine (T3) are nuclear hormone receptor agonists. B27 Supplement may be added to a culture medium as a concentrate or diluted before addition to a culture medium. It may be used at a 1× final concentration or at other final concentrations. Use of B27 Supplement is a convenient way to incorporate biotin, cholesterol, linoleic acid, linolenic acid, progesterone, putrescine, retinol, retinyl acetate, sodium selenite, tri-iodothyronine (T3), DL-alpha tocopherol (vitamin E), albumin, insulin and transferrin into a culture medium of the invention.

BMP Inhibitors

A component that is preferably added to the basal culture medium is a BMP inhibitor. BMPs bind as a dimeric ligand to a receptor complex consisting of two different receptor serine/threonine kinases, type I and type II receptors. The type II receptor phosphorylates the type I receptor, resulting in the activation of this receptor kinase. The type I receptor subsequently phosphorylates specific receptor substrates (SMAD), resulting in a signal transduction pathway leading to transcriptional activity.

A BMP inhibitor is defined as an agent that binds to a BMP molecule to form a complex wherein the BMP activity is neutralized, for example by preventing or inhibiting the binding of the BMP molecule to a BMP receptor. Alternatively, said inhibitor is an agent that acts as an antagonist or reverse agonist. This type of inhibitor binds with a BMP receptor and prevents binding of a BMP to said receptor. An example of a latter agent is an antibody that binds a BMP receptor and prevents binding of BMP to the antibody-bound receptor.

A BMP inhibitor may be added to the media in an amount effective to inhibit a BMP-dependent activity in a cell to at most 90%, more preferred at most 80%, more preferred at most 70%, more preferred at most 50%, more preferred at most 30%, more preferred at most 10%, more preferred 0%, relative to a level of a BMP activity in the absence of said inhibitor, as assessed in the same cell type. As is known to a skilled person, a BMP activity can be determined by measuring the transcriptional activity of BMP, for example as exemplified in Zilberberg et al., 2007. BMC Cell Biol. 8:41.

Several classes of natural BMP-binding proteins are known, including Noggin (Peprotech), Chordin and chordin-like proteins (R&D systems) comprising chordin domains, Follistatin and follistatin-related proteins (R&D systems) comprising a follistatin domain, DAN and DAN-like proteins (R&D systems) comprising a DAN cysteine-knot domain, sclerostin/SOST (R&D systems), decorin (R&D systems), and alpha-2 macroglobulin (R&D systems).

A preferred BMP inhibitor for use in a method of the invention is selected from Noggin, DAN, and DAN-like proteins including Cerberus and Gremlin (R&D systems). These diffusible proteins are able to bind a BMP ligand with varying degrees of affinity and inhibit their access to signalling receptors. The addition of any of these BMP inhibitors to the basal culture medium prevents the loss of stem cells.

A preferred BMP inhibitor is Noggin. In the context of a culture medium of the invention, Noggin is also referred to herein as "N". Noggin is preferably added to the basal culture medium at a concentration of at least 10 ng/ml, more preferred at least 20 ng/ml, more preferred at least 50 ng/ml, more preferred at least 100 ng/ml. A still more preferred concentration is approximately 100 ng/ml or exactly 100 ng/ml. During culturing of stem cells, said BMP inhibitor may be added to the culture medium when required, for example, daily or every other day. The BMP inhibitor is preferably added to the culture medium every second day. The culture medium may be refreshed when required, for example, daily or every other day, although is preferably refreshed every fourth day.

Wnt Agonists

A further component that may be added to the basal culture medium is a Wnt agonist. In the context of a culture medium of the invention, the Wnt agonist is also referred to herein as "W". The Wnt signalling pathway is defined by a series of events that occur when a Wnt protein binds to a cell-surface receptor of a Frizzled receptor family member. This results in the activation of Dishevelled family proteins which inhibit a complex of proteins that includes axin, GSK-3, and the protein APC to degrade intracellular β-catenin. The resulting enriched nuclear β-catenin enhances transcription by TCF/LEF family transcription factors.

A Wnt agonist is defined as an agent that activates TCF/LEF-mediated transcription in a cell. Wnt agonists are therefore selected from true Wnt agonists that bind and activate a Frizzled receptor family member including any and all of the Wnt family proteins, an inhibitor of intracellular β-catenin degradation, and activators of TCF/LEF. Said Wnt agonist is added to the media in an amount effective to stimulate a Wnt activity in a cell by at least 10%, more preferred at least 20%, more preferred at least 30%, more preferred at least 50%, more preferred at least 70%, more preferred at least 90%, more preferred at least 100%, relative to a level of said Wnt activity in the absence of said molecule, as assessed in the same cell type. As is known to a skilled person, a Wnt activity can be determined by measuring the transcriptional activity of Wnt, for example by pTOPFLASH and pFOPFLASH Tcf luciferase reporter constructs (Korinek et al., 1997. Science 275:1784-1787).

A Wnt agonist may comprise a secreted glycoprotein including Wnt-1/Int-1; Wnt-2/Irp (Int-1-related Protein); Wnt-2b/13; Wnt-3/Int-4; Wnt-3a (R&D systems); Wnt-4; Wnt-5a; Wnt-5b; Wnt-6 (Kirikoshi H et al. 2001. Biochem Biophys Res Com 283: 798-805); Wnt-7a (R&D systems); Wnt-7b; Wnt-8a/8d; Wnt-8b; Wnt-9a114; Wnt-9b/14b/15; Wnt-10a; Wnt-10b/12; Wnt-11; and Wnt-16. An overview of human Wnt proteins is provided in "THE WNT FAMILY OF SECRETED PROTEINS", R&D Systems Catalog, 2004.

Further Wnt agonists include the R-spondin family of secreted proteins, which is implicated in the activation and regulation of Wnt signaling pathway and which is comprised of 4 members (R-spondin 1 (NU206, Nuvelo, San Carlos, Calif.), R-spondin 2 ((R&D systems), R-spondin 3, and R-spondin-4); and Norrin (also called Norrie Disease Protein or NDP) (R&D systems), which is a secreted regulatory protein that functions like a Wnt protein in that it binds with high affinity to the Frizzled-4 receptor and induces activation of the Wnt signaling pathway (Kestutis Planutis et al. (2007) BMC Cell Biol. 8: 12).

Compounds that mimic the activity of R-spondin may be used as Wnt agonists of the invention. It has recently been found that R-spondin interacts with Lgr5. Thus, Lgr5 agonists such as agonistic anti-Lgr5 antibodies are examples of Wnt agonists that may be used in the invention.

In the context of a culture medium of the invention, R-spondin is also referred to herein as "R".

A small-molecule agonist of the Wnt signaling pathway, an aminopyrimidine derivative, was recently identified and is also expressly included as a Wnt agonist (Liu et al. (2005) Angew Chem Int Ed Engl. 44, 1987-90).

Known GSK-inhibitors comprise small-interfering RNAs (siRNA; Cell Signaling), lithium (Sigma), kenpaullone (Biomol International; Leost, M. et al. (2000) Eur. J. Biochem. 267, 5983-5994), 6-Bromoindirubin-30-acetoxime (Meijer, L. et al. (2003) Chem. Biol. 10, 1255-1266), SB 216763 and SB 415286 (Sigma-Aldrich), and FRAT-family members and FRAT-derived peptides that prevent interaction of GSK-3 with axin.

An overview is provided by Meijer et al., (2004) Trends in Pharmacological Sciences 25, 471-480, which is hereby incorporated by reference. Methods and assays for determining a level of GSK-3 inhibition are known to a skilled person and comprise, for example, the methods and assay as described in Liao et al 2004, Endocrinology, 145(6): 2941-9).

In a preferred embodiment, said Wnt agonist is selected from one or more of a Wnt family member, R-spondin 1-4 (for example, R-spondin 1 or R-spondin 4), Norrin, and a GSK-inhibitor. It was found by the inventors that the addition of at least one Wnt agonists to the basal culture medium is important for proliferation of the liver epithelial stem cells or isolated biliary duct or isolated liver fragments.

In a further preferred embodiment, said Wnt agonist comprises or consists of R-spondin 1. R-spondin 1 is preferably added to the basal culture medium at a concentration of at least 200 ng/ml, more preferred at least 300 ng/ml, more preferred at least 500 ng/ml. A still more preferred concentration of R-spondin 1 is approximately 500 ng/ml or exactly 500 ng/ml. During culturing of stem cells, said Wnt family member may be added to the culture medium when required, for example, daily or every other day. The Wnt family member is preferably added to the culture medium every second day. The culture medium may be refreshed when required, for example, daily or every other day, although is preferably refreshed every fourth day.

In a preferred embodiment, a Wnt agonist is selected from the group consisting of: R-spondin, Wnt-3a and Wnt-6. More preferably, R-spondin and Wnt-3a are both used as a Wnt agonist. This combination is particularly preferred since this combination surprisingly has a synergistic effect on organoid formation. Preferred concentrations are 1-500 ng/ml, for example, 1-10 ng/ml, 10-100 ng/ml, 1-50 ng/ml, 10-200 ng/ml, 200 to 500 ng/ml, 30 ng/ml for R-spondin and 100 ng/ml to 1000 ng/ml, for example, 100 ng/ml or 1000 ng/ml for Wnt3a.

A Wnt agonist is preferably a Wnt ligand, such as for example Wnt3a, and may be freshly added to a culture medium. Alternatively, a Wnt ligand is expressed in a cell line by transfecting or infected a cell line with a suitable expression construct expressing said Wnt ligand. Said cell line is cultured and the culture medium comprising the secreted Wnt ligand is harvested at suitable time intervals. For example, cells will produce Wnt3a as soon as they reach confluency and stop growing. Culture medium from cells that were not transfected or infected with said expression construct is used as a control. The conditioned medium is harvested and tested, for example in an assay wherein luciferase expression in controlled by TCF responsive elements to test for the presence of a Wnt agonist such as Wnt3a (Korinek et al., 1997. Science 275:1784-1787). The medium is diluted when used in the cultures to regenerate tissue. As is known to the skilled person, the addition of an excess of Wnt ligand sometimes is as detrimental for the culture as is the addition of too little Wnt ligand. Therefore, the actual dilution of the conditioned medium will depend on the amount of Wnt ligand that is determined in the test.

Mitogenic Growth Factors

Yet a further component that is added to the basal culture medium is a combination of mitogenic growth factors, selected from the group of epidermal growth factor (EGF; (preferably from Peprotech), a fibroblast growth factor (FGF) able to bind to FGFR2 or FGFR4, and hepatocyte growth factor (HGF) (also preferably from Peprotech). An FGF able to bind to FGFR2 (FGF receptor) or FGFR4 is preferably FGF4, FGF7 or FGF10 (preferably from Peprotech), most preferably FGF10. Preferably all 3 of EGF, an FGF and HGF are used. In the context of a culture medium of the invention, EGF is also referred to herein as "E", FGF is also referred to herein as "F" and HGF is also referred to herein as "H". EGF is a potent mitogenic factor for a variety of cultured ectodermal and mesodermal cells and has a profound effect on the differentiation of specific cells in vivo and in vitro and of some fibroblasts in cell culture. The EGF precursor exists as a membrane-bound molecule which is proteolytically cleaved to generate the 53-amino acid peptide hormone that stimulates cells. EGF exerts its effects in the target cells by binding to the plasma membrane located EGF receptor. The EGF receptor is a transmembrane protein tyrosine kinase. Binding of EGF to the receptor causes activation of the kinase and subsequently receptor autophosphorylation. The autophosphorylation is essential for the interaction of the receptor with its substrates. The signal transduction pathways activated by EGF include the phosphatidylinositol pathway, leading to activation of protein kinase C and to increase in the intracellular $Ca^{2+}$ concentration, and to the ras pathway leading to MAP kinase activation. These pathways are involved in regulating cellular proliferation, differentiation, and survival (Herbst, 2004, Int Journal of radiation oncology, 59, 2, S21-S26).

EGF is preferably added to the basal culture medium at a concentration of between 5 and 500 ng/ml or of at least 5 and not higher than 500 ng/ml. A preferred concentration is at least 10, 20, 25, 30, 40, 45, or 50 ng/ml and not higher than 500, 450, 400, 350, 300, 250, 200, 150, or 100 ng/ml. A more preferred concentration is at least 50 and not higher than 100 ng/ml. An even more preferred concentration is about 50 ng/ml or 50 ng/ml.

FGF10 is a protein that belongs to the fibroblast growth factor (FGF) family of proteins. FGF family members possess broad mitogenic and cell survival activities, and are involved in a variety of biological processes, including embryonic development, cell growth, morphogenesis, tissue repair, tumor growth and invasion. FGFs stimulate cells by interacting with cell surface tyrosine kinase receptors (FGFR). Four closely related receptors (FGFR1-FGFR4) have been identified. FGFR1-FGFR3 genes have been shown to encode multiple isoforms, and these isoforms can be critical in determining ligand specificity. Most FGFs bind more than one receptor (Ornitz J Biol Chem. 1998 Feb. 27; 273 (9):5349-57). However, FGF10 and FGF7 are unique among FGFs in that they interact only with a specific isoform of FGFR2, designated FGFR2b which is expressed exclusively by epithelial cells (Igarashi, J Biol Chem. 1998 273(21):13230-5). FGF10 is a preferred FGF able to bind to FGFR2 or FGFR4.

Hepatocyte growth factor/scatter factor (HGF/SF) is a morphogenic factor that regulates cell growth, cell motility, and morphogenesis by activating a tyrosine kinase signaling cascade after binding to the proto-oncogenic c-Met receptor.

The same concentrations may be used for FGF10 and HGF. Preferred concentrations for FGF10 are 20, 50, 100, 500 ng/ml, not higher than 500 ng/ml. Preferred concentrations for HGF are 1, 10, 20, 50 ng/ml, not higher than 50 ng/ml. During culturing of stem cells, said combination of mitogenic growth factors (i.e. EGF, FGF10 and HGF) is preferably added to the culture medium when required, for example, daily or every other day. It is preferable that it is added every second day. The culture medium may be refreshed when required, for example, daily or every other day, although is preferably refreshed every fourth day.

In some embodiments, a TGF-beta inhibitor such as A83-01 is additionally present in the EM1 medium. This is particularly useful when human cells or organoids are being cultured. In some embodiments, the A83-01 is present at a concentration of between 400-600 nM, for example 450-550 nM, 470-530 nM or approximately 500 nM. In embodiments in which a TGF-beta inhibitor is present in EM1, a Notch inhibitor is preferably not present.

Preferred Expansion Media of the Invention

Preferred culture media and methods of using these are described in the Examples.

For example, an cell culture medium may comprise or consist of a basal medium to which is added: EGF and R-spondin 1 supplemented with FGF10, HGF and Nicotinamide; for example, EGF (50 ng/ml) and R-spondin 1 (1 ug/ml) supplemented with FGF10 (100 ng/ml), HGF (25-50 ng/ml) and Nicotinamide (1-10 mM). The inventors have found that this medium is preferable for long-term expansion of cells. Thus, this cell culture medium is preferred for use as an EM2 of the invention. The basal medium is preferably supplemented with B27, N2 and 200 ng/ml N-Acetylcysteine. In some embodiments, the basal medium is Advanced-DMEM/F12. However, any other suitable basal medium may be used.

Another preferred cell culture medium, and method of using this medium, is described in the examples, and comprises or consists of Advanced-DMEM/F12 preferably supplemented with B27, N2, 200 ng/ml N-Acetylcysteine, 50 ng/ml EGF, 1 µg/ml R-spondin1, 10 nM gastrin, 100 ng/ml FGF10, 10 mM Nicotinamide and 50 ng/ml HGF and 50% Wnt conditioned media and, preferably 10-100 ng/ml Noggin. Wnt conditioned media comprises Advanced DMEM, P/S, B27, N2 and also FCS. 293T cells transfected with Wnt3A expression plasmid produce Wnt. The whole medium is taken after a few days (i.e. with secreted Wnt) and used as the Wnt source.

The invention therefore provides a cell culture medium, comprising or consisting of a basal medium for animal or human cells to which is added:

Epidermal Growth Factor, an FGF able to bind to FGFR2 or FGFR4, preferably FGF10 and HGF as mitogenic growth factors, gastrin, Nicotinamide, B27, N2 and N-Acetylcystein, and preferably a BMP inhibitor more preferably Noggin and a Wnt agonist, more preferably R-spondin 1 and/or Wnt-3a.

The invention thus encompasses a first preferred culture medium comprising or consisting of a basal medium for animal or human cells to which is added:

Epidermal Growth Factor, FGF10 and HGF as mitogenic growth factors, gastrin, Nicotinamide, B27, N2 and N-Acetylcysteine, a BMP inhibitor more preferably Noggin and a Wnt agonist, more preferably R-spondin 1 and Wnt-3a.

This medium may be used as an EM1 cell culture medium of the invention to stimulate initial expansion of cells.

In some embodiments, the medium used as an EM1 cell culture medium comprises all the components of an EM2 culture medium of the invention and additionally comprises Wnt-3a and Noggin.

In embodiments in which the basal medium is supplemented with N-Acetylcysteine, B27 and N2, the following are preferably added to the culture media: EGF, R-spondin1, gastrin, FGF10, Nicotinamide and HGF and Wnt-conditioned media. Preferably, the basal medium is supplemented with N-Acetylcysteine, EGF, R-spondin1, gastrin, FGF10, Nicotinamide and HGF and Wnt-conditioned media in accordance with the quantities described hereinabove.

For example, in some embodiments the basal medium may be supplemented with 150 ng/ml to 250 ng/ml N-Acetylcysteine; preferably, the basal medium is supplemented with, about or exactly 200 ng/ml N-Acetylcysteine. For example, in some embodiments the basal medium may be supplemented with 40 ng/ml to 60 ng/ml EGF; preferably, the basal medium is supplemented with about or exactly 50 ng/ml EGF. For example, in some embodiments the basal medium may be supplemented with 0.5 µg/ml to 1.5 µg/ml R-spondin1; preferably, the basal medium is supplemented with about or exactly 1 µg/ml R-spondin1. For example, in some embodiments the basal medium may be supplemented with 5 nM to 15 nM gastrin; preferably, the basal medium is supplemented with about or exactly 10 nM gastrin. For example, in some embodiments the basal medium may be supplemented with 25-200 ng/ml FGF10, for example 70 ng/ml to 130 ng/ml FGF10; preferably, the basal medium is supplemented with about or exactly 100 ng/ml FGF10. For example, in some embodiments the basal medium may be supplemented with 5 mM to 15 mM Nicotinamide; preferably, the basal medium is supplemented with about or exactly 10 mM Nicotinamide. For example, in some embodiments the basal medium may be supplemented with 25 ng/ml to 100 ng/ml HGF, for example 35 ng/ml to 65 ng/ml HGF; preferably, the basal medium is supplemented with about or exactly and 50 ng/ml HGF. For example, in some embodiments the basal medium may be supplemented with 35% to 65% Wnt-conditioned media; preferably, the basal medium is supplemented with about or exactly 50% Wnt-conditioned media.

In some embodiments one or both of gastrin and N2 are not present in the cell culture medium.

Preferably, the basal medium is advanced-DMEM/F12.

This first culture medium (for example, EM1, EM2 or both EM1 and EM2) is preferably used during the first two weeks of the culture method of the invention. However, it may be used for a shorter time period, such as for 1, 2, 3, 5, 7, or 10 days, or a longer time period, such as 3, 4, 5, 10, 20 or more weeks, 5 months or more, for example, 6, 7, 8, 9, 10, 11, 12 months or more.

Differentiation Medium (DM):

In another aspect, there is provided a second cell culture medium which comprises or consists of a basal medium for animal or human cells to which is added: EGF, a TGF-beta inhibitor, and a Notch inhibitor. The inventors have found that this medium is useful for differentiating cells. The medium used for differentiating the cells may be referred to herein as DM.

Preferably, the second cell culture medium also comprises FGF and/or HGF.

In one embodiment, the second culture medium comprises or consists of a basal medium for animal or human cells to which is added:

Epidermal Growth Factor, FGF10 and HGF as mitogenic growth factors;

a Notch inhibitor; and a TGF-beta inhibitor.

In one embodiment, the TGF-beta inhibitor is A83-01 and/or the Notch inhibitor is DAPT. In another embodiment, the DM cell culture medium additionally comprises Dexamethasone.

A preferred second cell culture medium, and method of using this medium, is described in the examples, and comprises or consists of a basal medium to which is added: 50 ng/ml EGF, 100 ng/ml FGF10, 50 nM A8301 and 10 uM DAPT. Advanced-DMEM/F12 may be used as the basal medium as may any other suitable basal medium.

In some embodiments, the second cell culture medium does not comprise R-spondin or Wnt. In some embodiments, the second cell culture medium does not comprise a Wnt agonist. In some embodiments, the second cell culture medium does not comprise Nicotinamide. In some embodiments, the second cell culture medium does not comprise a BMP inhibitor.

The inventors have discovered that R-spondin1 and Nicotinamide both inhibit the expression of the mature hepatocyte marker CYP3A11 and yet promote the expression of the hepatoblast marker albumin. Therefore, to increase differentiation of the cells to more mature liver fates, the inventors removed R-spondin and Nicotinamide from the cell culture. The inventors have also discovered that the expression of specific biliary transcription factors is highly upregulated in expansion cultures containing R-spondin1, indicating that the culture gene expression was unbalanced towards a more biliary cell fate. Notch and TGF-beta signaling pathways have been implicated in biliary cell fate in vivo. In fact, deletion of Rbpj (essential to achieve active Notch signalling) results in abnormal tubulogenesis (Zong Y. Development 2009) and the addition of TGF-beta to liver explants facilitates the biliary differentiation in vitro (Clotman F. Genes and Development 2005). Since both Notch and TGF-beta signalling pathways were highly upregulated in the liver cultures (FIG. 9) the inventors reasoned that inhibition of biliary duct cell-fate might trigger the differentiation of the cells towards a more hepatocytic phenotype. It was found that addition of a TGF-beta inhibitor (such as A8301) and a Notch inhibitor (such as DAPT) to a differentiation medium that preferably does not contain R-spondin or Wnt, enhances the expression of mature hepatocyte markers and increases the number of hepatocyte-like cells (for example, see example 2).

Notch is a transmembrane surface receptor that can be activated through multiple proteolytic cleavages, one of them being cleavage by a complex of proteins with protease activity, termed gamma-secretase. Gamma-secretase is a protease that performs its cleavage activity within the membrane. Gamma-secretase is a multicomponent enzyme and is composed of at least four different proteins, namely, presenilins (presenilin 1 or 2), nicastrin, PEN-2 and APH-I. Presenilin is the catalytic centre of gamma-secretase. On ligand binding the Notch receptor undergoes a conformational change that allows ectodomain shedding through the action of an ADAM protease which is a metalloprotease. This is followed immediately by the action of the gamma-secretase complex which results in the release of the Notch intracellular domain (NICD). NICD translocates to the nucleus where it interacts with CSL (C-promoter-binding factor/recombinant signal-sequence binding protein Jκ/Supressor-of-Hairless/Lag1). The binding of NICD converts CSL from a transcriptional repressor to an activator which results in the expression of Notch target genes. Examples of preferred Notch inhibitors that can be used in the context of this invention are: gamma-secretase inhibitors, such as DAPT or dibenzazepine (DBZ) or benzodiazepine (BZ) or LY-411575, an inhibitor capable of diminishing ligand mediated activation of Notch (for example via a dominant negative ligand of Notch or via a dominant negative Notch or via an antibody capable of at least in part blocking the interacting between a Notch ligand and Notch), or an inhibitor of ADAM proteases.

TGF-beta signalling is involved in many cellular functions, including cell growth, cell fate and apoptosis. Signalling typically begins with binding of a TGF-beta superfamily ligand to a type II receptor which recruits and phosphorylates a type I receptor. The type 1 receptor then phosphorylates SMADs, which act as transcription factors in the nucleus and regulate target gene expression. Alternatively, TGF-beta signalling can activate MAP kinase signalling pathways, for example, via p38 MAP kinase. The TGF-beta superfamily ligands comprise bone morphogenic proteins (BMPs), growth and differentiation factors (GDFs), anti-müllerian hormone (AMH), activin, nodal and TGF-betas.

A TGF-beta inhibitor is an agent that reduces the activity of the TGF-beta signalling pathway. There are many ways of disrupting the TGF-beta signaling pathway that are known in the art and that can be used in conjunction with this invention. For example, the TGF-beta signaling may be disrupted by: inhibition of TGF-beta expression by a small-interfering RNA strategy; inhibition of furin (a TGF-beta activating protease); inhibition of the pathway by physiological inhibitors, such as inhibition of BMP by Noggin, DAN or DAN-like proteins; neutralisation of TGF-beta with a monoclonal antibody; inhibition with small-molecule inhibitors of TGF-beta receptor kinase 1 (also known as activin receptor-like kinase, ALK5), ALK4, ALK6, ALK7 or other TGF-beta-related receptor kinases; inhibition of Smad 2 and Smad 3 signaling by overexpression of their physiological inhibitor, Smad 7, or by using thioredoxin as an Smad anchor disabling Smad from activation (Fuchs, O. Inhibition of TGF-Signaling for the Treatment of Tumor Metastasis and Fibrotic Diseases. Current Signal Transduction Therapy, Volume 6, Number 1, January 2011, pp. 29-43(15)).

Various methods for determining if a substance is a TGF-beta inhibitor are known and might be used in conjunction with the invention. For example, a cellular assay may be used in which cells are stably transfected with a reporter construct comprising the human PAI-1 promoter or Smad binding sites, driving a luciferase reporter gene. Inhibition of luciferase activity relative to control groups can be used as a measure of compound activity (De Gouville et al., Br J Pharmacol. 2005 May; 145(2): 166-177).

A TGF-beta inhibitor according to the present invention may be a protein, peptide, small-molecules, small-interfering RNA, antisense oligonucleotide, aptamer or antibody. The inhibitor may be naturally occurring or synthetic. Examples of preferred small-molecule TGF-beta inhibitors that can be used in the context of this invention include the small molecule inhibitors listed in table 1:

TABLE 1

Small-molecule TGF-beta inhibitors targeting receptor kinases

| Inhibitor | Targets | IC50 (nM) | Mol Wt | Name | Formula |
|---|---|---|---|---|---|
| A83-01 | ALK5 (TGF-β R1) | 12 | 421.52 | 3-(6-Methyl-2-pyridinyl)-N-phenyl-4-(4-quinolinyl)-1H-pyrazole-1-carbothioamide | C25H19N5S |
|  | ALK4 | 45 |  |  |  |
|  | ALK7 | 7.5 |  |  |  |
| SB-431542 | ALK5 | 94 | 384.39 | 4-[4-(1,3-benzodioxol-5-yl)-5-(2-pyridinyl)-1H-imidazol-2-yl]benzamide | C22H16N4O3 |
|  | ALK4 |  |  |  |  |
|  | ALK7 |  |  |  |  |
| SB-505124 | ALK5 | 47 | 335.4 | 2-(5-benzo[1,3]dioxol-5-yl-2-tert-butyl-3Himidazol-4-yl)-6-methylpyridine hydrochloride hydrate | C20H21N3O2 |
|  | ALK4 | 129 |  |  |  |
| SB-525334 | ALK5 | 14.3 | 343.42 | 6-[2-(1,1-Dimethylethyl)-5-(6-methyl-2-pyridinyl)-1H-imidazol-4-yl]quinoxaline | C21H21N5 |
| SD-208 | ALK5 | 49 | 352.75 | 2-(5-Chloro-2-fluorophenyl)-4-[(4-pyridyl)amino]pteridine | C17H10ClFN6 |
| LY-36494 | TGR-β RI | 59 | 272.31 | 4-[3-(2-Pyridinyl)-1H-pyrazol-4-yl]-quinoline | C17H12N4 |
|  | TGF-β RII | 400 |  |  |  |
|  | MLK-7K | 1400 |  |  |  |

TABLE 1-continued

Small-molecule TGF-beta inhibitors targeting receptor kinases

| Inhibitor | Targets | IC50 (nM) | Mol Wt | Name | Formula |
|---|---|---|---|---|---|
| SJN-2511 | ALK5 | 23 | 287.32 | 2-(3-(6-Methylpyridine-2-yl)-1H-pyrazol-4-yl)-1,5-naphthyridine | C17H13N5 |

A method of the invention may comprise the use of one or more of any of the inhibitors listed in table 1. A method of the invention may comprise the use of any combination of one inhibitor with another inhibitor listed. For example, a method of the invention may comprise the use of SB-525334 or SD-208 or A83-01; or a method of the invention may comprise the use of SD-208 and A83-01; or a method of the invention may comprise the use of SD-208 and A83-01. The skilled person will appreciate that a number of other small-molecule inhibitors exist that are primarily designed to target other kinases, but at high concentrations may also inhibit TGF-beta receptor kinases. For example, SB-203580 is a p38 MAP kinase inhibitor that, at high concentrations (for example, approximate 10 uM or more) is thought to inhibit ALK5. Any such inhibitor that inhibits the TGF-beta signalling pathway can also be used in the context of this invention.

A83-01 may be added to the culture medium at a concentration of between 10 nM and 10 uM, or between 20 nM and 5 uM, or between 50 nM and 1 uM. For example, A83-01 may be added to the culture medium at approximately 500 nM. When used in an EM, A83-01 may be added to the culture medium at a concentration of between 350-650 nM, for example, 450-550 nM, more preferably approximately 500 nM. When used in the DM, A83-01 may be added to the culture medium at a concentration of between 25-75 nM, for example, 40-60 nM or approximately 50 nM.

SB-431542 may be added to the culture medium at a concentration of between 80 nM and 80 uM, or between 100 nM and 40 uM, or between 500 nM and 10 uM. For example, SB-431542 may be added to the culture medium at approximately 1 uM.

SB-505124 may be added to the culture medium at a concentration of between 40 nM and 40 uM, or between 80 nM and 20 uM, or between 200 nM and 1 uM. For example, SB-505124 may be added to the culture medium at approximately 500 nM.

SB-525334 may be added to the culture medium at a concentration of between 10 nM and 10 uM, or between 20 nM and 5 uM, or between 50 nM and 1 uM. For example, SB-525334 may be added to the culture medium at approximately 100 nM.

LY 364947 may be added to the culture medium at a concentration of between 40 nM and 40 uM, or between 80 nM and 20 uM, or between 200 nM and 1 uM. For example, LY 364947 may be added to the culture medium at approximately 500 nM.

SD-208 may be added to the culture medium at a concentration of between 40 nM and 40 uM, or between 80 nM and 20 uM, or between 200 nM and 1 uM. For example, SD-208 may be added to the culture medium at approximately 500 nM.

SJN 2511 may be added to the culture medium at a concentration of between 20 nM and 20 uM, or between 40 nM and 10 uM, or between 100 nM and 1 uM. For example, A83-01 may be added to the culture medium at approximately 200 nM.

In a further aspect, the invention provides an alternative second culture medium comprising or consisting of a basal medium for animal or human cells to which is added:

Epidermal Growth Factor, FGF10 and HGF as mitogenic growth factors;

gastrin, Nicotinamide, B27, N2 and N-Acetylcysteine.

This alternative second culture medium is useful as a differentiation medium (DM). This alternative second culture medium is preferably used after the two first weeks of culture. At this stage, it seems that a BMP inhibitor and a Wnt ligand are no longer needed. Thus, in some embodiments, the alternative second culture medium does not comprise a BMP inhibitor or a Wnt ligand. In some embodiments, the alternative second culture medium does not comprise a BMP inhibitor or a Wnt agonist.

As with the first culture medium (EM, i.e. EM1 and EM2 or EM1 or EM2), the basal medium may in some embodiments be supplemented with N-Acetylcysteine, EGF, gastrin, FGF10, Nicotinamide and HGF in accordance with the quantities described hereinabove. For example, preferably, the basal medium is supplemented with about or exactly 200 ng/ml N-Acetylcysteine. Preferably, the basal medium is supplemented with about or exactly 50 ng/ml EGF. Preferably, the basal medium is supplemented with about or exactly 10 nM gastrin. Preferably, the basal medium is supplemented with about or exactly 100 ng/ml FGF10. Preferably, the basal medium is supplemented with about or exactly 10 mM Nicotinamide. Preferably, the basal medium is supplemented with about or exactly 50 ng/ml HGF.

A first and a second cell culture medium used according to the invention allows the survival and/or proliferation and/or differentiation of epithelial stem cells or liver epithelial stem cells or isolated biliary duct or isolated liver fragments on an extracellular matrix.

A medium allowing for survival and/or proliferation is a medium which preferably induces or promotes the survival and/or proliferation of cells during at least 5, 10, 15, 20, 30, 40, 50, 60, 70, 80, 90, 100, 120, 140, 160, 180, 200 days of culture. Proliferation can be assessed using techniques known in the art such as BrdU staining, Edu staining, Ki67 staining and the use of growth curves assay can be done. For example, we have shown that from 10 biliary ducts, it is possible after 6 days to dilute to 6 wells with 10 organoids per well (60 new organoids). In each passage of 6 days we can generate around 360 organoids. By performing 1 passage/week over 32 weeks we are able to generate over 11,000 (11520) new organoid structures in only 7 months. This is important for the industry, since the availability of cells and organoids for transplantation poses a significant problem. For a mouse transplant, for example, a minimum of $10^5$ cells are required. Possibly $10^6$, or $10 \times 10^6$ might be required for a human transplant, in order for a graft to be successful.

Put another way, media used according to the invention is capable of expanding a population of stem cells to form liver organoids for at least 3, at least 4, at least 5, at least 6, at least 7, at least 8, at least 9, at least 10, at least 20, at least 30, at least 40, at least 50, at least 60, at least 70, at least 80, at least 90 or at least 100, passages under appropriate conditions.

The second medium as identified above preferably induces or promotes a specific differentiation of cells during at least five days of culture. Differentiation may be measured by detecting the presence of a specific marker associated with the liver lineage as defined herein. Differentiation may be measured by detecting the presence of a specific marker associated with the liver lineage as defined herein. Depending on the identity of the marker, the expression of said marker may be assessed by RTPCR or immunohistochemistry after at least 5, 7, 8, 9, 10, 11, 12, 13, 14, 15, 16 days of culture in a first medium or in a first subsequently in a second medium as defined herein.

A differentiation medium is a medium which preferably induces or promotes a specific differentiation of cells during at least five days of culture. Differentiation may be measured by detecting the presence of a specific marker associated with the liver lineage as defined herein.

Within the context of the invention, the term cell culture medium is synonymous with medium, culture medium or cell medium or basal medium or basal cell medium or basal cell culture medium or expansion medium or differentiation medium.

According to a still further aspect of the invention, there is provided a hermetically-sealed vessel containing a culture medium of the invention. In some embodiments, the culture medium is an expansion medium. In some embodiments, the culture medium is a differentiation medium. Hermetically-sealed vessels may be preferred for transport or storage of the culture media, to prevent contamination. The vessel may be any suitable vessel, such as a flask, a plate, a bottle, a jar, a vial or a bag.

Methods for Obtaining and/or Culturing Stem Cells

The method for obtaining and/or culturing a liver fragment or a liver organoid, comprises culturing epithelial stem cells, and/or isolated tissue fragments comprising said epithelial stem cells in contact with an extracellular matrix in the presence of one or more cell culture media according to the invention.

In some embodiments, a method for obtaining and/or culturing a liver fragment or a liver organoid comprises culturing epithelial stem cells, and/or isolated tissue fragments comprising said epithelial stem cells in contact with an extracellular matrix in the presence of EM1 medium and then EM2 medium and then DM medium.

In some embodiments, a method for obtaining and/or culturing a liver fragment or a liver organoid comprises culturing epithelial stem cells, and/or isolated tissue fragments comprising said epithelial stem cells in contact with an extracellular matrix in the presence of EM2 medium and then DM medium without the use of EM1 medium.

In some embodiments, a method for obtaining and/or culturing a liver fragment or a liver organoid comprises culturing epithelial stem cells, and/or isolated tissue fragments comprising said epithelial stem cells in contact with an extracellular matrix in the presence of EM1 medium and then DM medium without the use of EM2 medium.

The method for obtaining and/or culturing a liver fragment or a liver organoid, may comprise:

i) culturing epithelial stem cells, and/or isolated tissue fragments comprising said epithelial stem cells in contact with an extracellular matrix in the presence of a medium, the medium comprising a basal medium for animal or human cells to which is added: Epidermal Growth Factor, an FGF able to bind to FGFR2 or FGFR4, preferably FGF10 and HGF as mitogenic growth factors, Nicotinamide, and preferably, a Wnt agonist, preferably any one of R-spondin 1-4; and subsequently ii) culturing the stem cells, and/or isolated tissue fragments comprising said epithelial stem cells in contact with an extracellular matrix in the presence of a second cell culture medium as defined here (a DM medium).

In some embodiments, prior to the step i), the method comprises culturing the epithelial stem cells, and/or isolated tissue fragments comprising said epithelial stem cells in contact with an extracellular matrix in the presence of a medium comprising or consisting of a basal medium for animal or human cells to which is added EGF, a BMP inhibitor, R-spondin and Wnt. Preferably, the BMP inhibitor is Noggin and the EM1 medium is termed "ENRW" (EGF, Noggin, R-spondin and Wnt).

In one embodiment there is provided a method for obtaining and/or culturing a liver fragment or a liver organoid, wherein said method comprises:

culturing epithelial stem cells, and/or isolated tissue fragments comprising said epithelial stem cells in contact with an extracellular matrix in an EM2 culture medium as described herein, for example, a medium comprising a Wnt agonist, such as R-spondin, Epidermal Growth Factor, an FGF able to bind to FGFR2 or FGFR4, preferably FGF10, and nicotinamide. Preferably, the medium also comprises HGF.

In a further embodiment there is provided a method for obtaining and/or culturing a liver fragment or a liver organoid, wherein said method comprises:

culturing epithelial stem cells, and/or isolated tissue fragments comprising said epithelial stem cells in contact with an extracellular matrix in a medium comprising a BMP inhibitor, a Wnt agonist, Epidermal Growth Factor, a FGF able to bind to FGFR2 or FGFR4, preferably FGF10 and HGF as mitogenic growth factors, gastrin, Nicotinamide, B27, N2 and N-Acetylcysteine.

In another preferred method, after at least two weeks of culture in an EM1 medium as defined above, the culture is continued in a medium that does not comprise a BMP inhibitor and a Wnt agonist. In some embodiments, this culture is continued in an EM2 of the invention. In alternative embodiments, the culture is continued in a second medium of the invention (DM), which additionally comprises a TGF-beta inhibitor, such as A83-01, and a Notch inhibitor, such as DAPT. In some embodiments, this culture is continued in an EM2 and then a DM medium of the invention.

Therefore in a preferred method for obtaining and/or culturing a liver organoid, epithelial stem cells, and/or isolated liver tissue fragments comprising said epithelial stem cells are cultured in a first step in the first medium (EM), then subsequently in a discrete second step in the second medium (DM). The first culture step may have a duration of at least two weeks and may be longer, for example, 3 weeks or longer, 4 weeks or longer or 1, 2, 3, 4, 5, 6, 7, 8 months or longer. The second step preferably has a duration of 6 weeks or less, more preferably 1 month or less, for example 3 weeks or less, 2 weeks or less, 1 week or less. It has been found that many cells start dying after 2 weeks in DM and so preferably, the second step is 2 weeks or less or at most 1 month. Thus, it is only in less preferred embodiments, that the second step may have a duration of 8, 9, 10, 11, 12, 13, 14, 15, 16 days or 3 weeks or 1, 2, 3, 4, 5, 6 months or longer. Each step is preferably carried out using an extracellular matrix as defined herein, and using the culture media described in detail herein.

Alternatively in another embodiment, said method is carried out in the first medium, without switch to the second medium. This method may have a duration of 8, 9, 10, 11, 12, 13, 14, 15, 16 days or 3 weeks or 1, 2, 3, 4, 5, 6, 7, 8 months or longer.

In some embodiments, the step of culturing in the first medium of the invention comprises both culturing in EM1 medium and then culturing in EM2 medium. Thus, the periods described above may refer to the total period in which the cells or fragments are cultured in the EM1 and subsequently in the EM2 media. In some embodiments, the step of culturing in the EM1 culture medium may have a duration of less than 10 days, for example, less than 9, less than 8, less than 7, less than 6, less than 5, less than 4, less than 3, less than 2 or less than 1 day. In some embodiments, the step of culturing in the EM1 culture medium may have a duration of between 1 and 10 days, for example, 1-7 days, 2-6 days, 3-5 days, for example 4 or 5 days. In some embodiments, the step of culturing in the EM2 medium may have a duration of 10 days or longer, for example, 11, 12, 13, 14, 15, 16 days or longer, or 1-3 weeks or 2-4 weeks or 3-6 weeks or 1, 2, 3, 4, 5, 6 months or longer.

Preferred concentrations of each compound present in each medium have already been defined herein in the description or in the examples.

The methods described herein for obtaining and/or culturing a liver fragment or a liver organoid may also be used to obtain and/or culture a population of cells expressing Lgr5 and such methods are encompassed by the invention. A population of cells expressing Lgr5 obtained by a method of the invention is thus also provided.

As will be apparent to the skilled reader, the preferred culture methods of the invention are advantageous because feeder cells are not required. Feeder cell layers are often used to support the culture of stem cells, and to inhibit their differentiation. A feeder cell layer is generally a monolayer of cells that is co-cultured with, and which provides a surface suitable for growth of, the cells of interest. The feeder cell layer provides an environment in which the cells of interest can grow. Feeder cells are often mitotically inactivated (e.g. by irradiation or treatment with mitomycin C) to prevent their proliferation. The use of feeder cells is undesirable, because it complicates passaging of the cells (the cells must be separated from the feeder cells at each passage, and new feeder cells are required at each passage). The use of feeder cells can also lead to contamination of the desired cells with the feeder cells. This is clearly problematic for any medical applications, and even in a research context, complicates analysis of the results of any experiments performed on the cells. As noted elsewhere herein, the culture media of the invention are particularly advantageous because they can be used to culture cells without feeder cell contact, i.e. the methods of the invention do not require a layer of feeder cells to support the cells whose growth is being sponsored.

Accordingly, the compositions of the invention may be feeder cell-free compositions. A composition is conventionally considered to be feeder cell-free if the liver cells in the composition have been cultured for at least one passage in the absence of a feeder cell layer. A feeder cell-free composition of the invention will normally contain less than about 5%, less than about 4%, less than about 3%, less than about 2%, less than about 1% feeder cells (expressed as a % of the total number of cells in the composition) or preferably no feeder cells at all.

In one preferred embodiment, for example, if a liver organoid is to be used for regenerative medicine, the method may start from epithelial cells or from an isolated liver fragment. The cells or liver fragment may be autologous or allogeneic. "Autologous" cells are cells which originated from the same organism into which they are being re-introduced for cellular therapy, for example in order to permit tissue regeneration. An autologous cell does not, in principle, require matching to the patient in order to overcome the problems of immune rejection, and/or reduces the need for immune suppression interventions upon transplant. "Allogeneic" cells are cells which originated from an individual which is different from the individual into which the cells are being introduced for cellular therapy, for example in order to permit tissue regeneration, although of the same species. Some degree of patient matching may still be required to prevent the problems of rejection. Techniques for minimising tissue rejection will be known to those of skill in the art.

A preferred method of the invention encompasses a method for culturing an isolated liver fragment comprising said epithelial stem cells.

Another preferred method encompasses a method for obtaining a liver organoid from epithelial stem cells and/or isolated liver fragments comprising said epithelial stem cells.

Another preferred method encompasses a method for obtaining and culturing a liver organoid from epithelial stem cells and/or isolated liver fragments comprising said epithelial stem cells.

In a preferred method as earlier identified herein, the BMP inhibitor is selected from Noggin, DAN, and DAN-like proteins including Cerberus and Gremlin, preferably comprises or is Noggin, and/or said Wnt agonist is selected from one or more of Wnt, preferably Wnt-3a, R-spondin 1-4, Norrin, and a GSK-inhibitor, more preferably comprises or is Wnt-3a and/or R-spondin.

In another preferred method, a liver organoid originates from one single cell, preferably a cell expressing Lgr5, more preferably wherein the single cell comprises a nucleic acid construct comprising a nucleic acid molecule of interest. The cell may also express liver-specific markers such as Hnf1$\alpha$, and Hnf4.

The isolation of certain cell types expressing Lgr5 has already been described previously (see, for example, WO2009/022907 and WO2010/016766). However, liver specific stem cells expressing Lgr5 of the type disclosed herein have not previously been described. Accordingly, the invention provides a population of adult stem cells characterised by natural expression of at least Lgr5 and one or more of the following markers Hnf1$\alpha$, Hnf4a, Sox9, KRT7 and KRT19 at a significant level. This cell population also expresses markers of progenitor populations common to the small intestine and stomach, such as Cd44 and Sox9 (Barker & Huch et al Cell stem cell 2010). These are highly expressed in the stem cells according to the invention, but are not expressed in adult liver, reinforcing the self-renewal capacity of the liver cultures described herein. Cells according to this aspect of the invention may also up-regulate Wnt target genes, including for example, MMP7, Sp5 and Tnfrs19. This provides strong evidence of the requirement for an active and robust canonical Wnt signalling activity to maintain the self renewing capacity of these cultures.

By "natural expression" is meant that the cells have not been manipulated recombinantly in any way, i.e., the cells have not been artificially induced to express these markers or to modulate these markers' expression by introduction of exogenous genetic material, such as introduction of heterologous (non-natural) or stronger promoters or other regulatory sequences operably linked to either the endogenous genes or exogenously-introduced forms of the genes. Natural expression is from genomic DNA within the cells, including introns between the exon coding sequences where these exist. Natural expression is not from cDNA. Natural expression can if necessary be proven by any one of various methods, such as sequencing out from within the reading frame of the gene to check that no extraneous heterogenous sequence is present. "Adult" means post-embryonic. With respect to the stem cells of the present invention, the term "adult stem cell" means that the stem cell is isolated from a tissue or organ of an animal at a stage of growth later than the embryonic stage.

This stem cell population can also be characterised by a lack of natural expression of certain markers at any significant level, many of which are associated with cellular differentiation. Specifically, the cells of the isolated adult stem cell population do not naturally express one or more of Cd11b, CD13, CD14, AFP, Pdx1, any CYP member (e.g. CYP3A11, CYP 11A1) at a significant level. As defined herein, these markers are said be to be negative markers.

The term "expressed" is used to describe the presence of a marker within a cell. In order to be considered as being expressed, a marker must be present at a detectable level. By "detectable level" is meant that the marker can be detected using one of the standard laboratory methodologies such as PCR, blotting or FACS analysis. A gene is considered to be expressed by a cell of the population of the invention if expression can be reasonably detected after 30 PCR cycles, which corresponds to an expression level in the cell of at least about 100 copies per cell. The terms "express" and "expression" have corresponding meanings. At an expression level below this threshold, a marker is considered not to be expressed. The comparison between the expression level of a marker in a cell of the invention, and the expression level of the same marker in another cell, such as for example an embryonic stem cell, may preferably be conducted by comparing the two cell types that have been isolated from the same species. Preferably this species is a mammal, and more preferably this species is human. Such comparison may conveniently be conducted using a reverse transcriptase polymerase chain reaction (RT-PCR) experiment.

Any one of a number of physical methods of separation known in the art may be used to select the cells of this aspect of the invention and distinguish these from other cell types. Such physical methods may involve FACS and various immuno-affinity methods based upon makers specifically expressed by the cells of the invention. As described above, Lgr5, Hnf1α and Hnf4 are 3 of the cell markers expressed at high levels in the cells of the invention. Therefore, by way of illustration only, the cells of the invention may be isolated by a number of physical methods of separation, which rely on the presence of these markers.

In one embodiment, the cells of the invention may be isolated by FACS utilizing an antibody, for example, against one of these markers. As will be apparent to one skilled in the art, this may be achieved through a fluorescent labeled antibody, or through a fluorescent labeled secondary antibody with binding specificity for the primary antibody. Examples of suitable fluorescent labels includes, but is not limited to, FITC, Alexa Fluor® 488, GFP, CFSE, CFDA-SE, DyLight 488, PE, PerCP, PE-Alexa Fluor® 700, PE-Cy5 (TRI-COLOR®), PE-Cy5.5, PI, PE-Alexa Fluor® 750, and PE-Cy7. This list is provided by way of example only, and is not intended to be limiting.

It will be apparent to a person skilled in the art that FACS analysis using an anti-Lgr5 antibody will provide a purified cell population. However, in some embodiments, it may be preferable to purify the cell population further by performing a further round of FACS analysis using one or more of the other identifiable markers, preferably Hnf1α and Hnf4, but others may also be used.

In another embodiment, the cells of the invention may be isolated by immuno-affinity purification, which is a separation method well known in the art. By way of illustration only, the cells of the invention may be isolated by immuno-affinity purification directed towards c-kit. As will be apparent to one skilled in the art, this method relies upon the immobilisation of antibodies on a purification column. The cell sample is then loaded onto the column, allowing the appropriate cells to be bound by the antibodies, and therefore bound to the column. Following a washing step, the cells are eluted from the column using a competitor which binds preferentially to the immobilised anti-c-kit antibody, and permits the cells to be released from the column.

It will be apparent to a person skilled in the art that immuno-affinity purification using an immobilised antibody will provide a purified cell population. However, in some embodiments, it may be preferable to purify the cell population further by performing a further round of immuno-affinity purification using one or more of the other identifiable markers, for example Hnf4, and use an aliquot of the isolated clones to ascertain the expression of other relevant intracellular markers.

It will be apparent to a person skilled in the art that the sequential purification steps are not necessarily required to involve the same physical method of separation. Therefore, it will be clear that, for example, the cells may be purified through a FACS step using an anti-Lgr5 antibody, followed by an immuno-affinity purification step using a SSEA-1 affinity column. In certain embodiments, the cells may be cultured after isolation for at least about 15, at least about 20 days, at least about 25 days, or at least about 30 days. In certain aspects, the cells are expanded in culture longer to improve the homogeneity of the cell phenotype in the cell population.

Other features of this method are defined in the part of the description dedicated to definitions. Single-cell suspensions or small clusters of cells (2-50 cells/cluster) will normally be seeded, rather than large clusters of cells, as in known in the art. As they divide, such cells will be seeded onto a support at a density that promotes cell proliferation. Typically, when single cells are isolated the plating density of at least 1-500 cells/well is used, the surface of the well being 0.32 cm$^2$. When clusters are seeded the plating density is preferably 250-2500 cells/cm$^2$. For replating, a density of between about 2500 cells/cm$^2$ and about 5,000 cells/cm$^2$ may be used. During replating, single-cell suspensions or small cluster of cells will normally be seeded, rather than large clusters of cells, as in known in the art.

Organoids of the Invention

The cells described above grow into bodies which are herein termed "organoids". Accordingly, a liver organoid obtainable by a method of the invention is a further aspect of the invention. To the best of our knowledge, this is the first time that a liver organoid has been obtained that is functional and alive after such an extended period of time (i.e. at least 7 months of culture; see examples included herein). Functionality is preferably characterized by the presence of a liver marker as defined herein and/or by the structure of said organoid as defined herein. Since the final amount of liver organoids obtained correlates with the duration of culture, the skilled person will understand that the invention is a pioneer invention and potentially opens new possibilities in for example regenerative medicine.

For example, an organoid according to the present invention may comprise a population of cells of at least $1 \times 10^3$ cells, at least $1 \times 10^4$ cells, at least $1 \times 10^5$ cells, at least $1 \times 10^6$ cells, at least $1 \times 10^7$ cells or more. In some embodiments, each organoid comprises between approximately $1 \times 10^3$ cells and $5 \times 10^3$ cells; generally, 10-20 organoids may be grown together in one well of a 24 well plate.

Cells and organoids according to the present invention may be non-human animal or human. The inventors have shown, for the first time, that it is possible to grow and maintain both animal and human liver organoids in vitro, using the culture media and methods of the invention.

Illustrative examples of organoids generated according to the invention are given in the accompanying figures. It can be seen that organoids according to the invention may possess a cystic structure, with on the outside, a layer of cells with at least one bud and a central lumen. The organoids in the outside of the MATRIGEL™ tend to be larger than the organoids in the center of the MATRIGEL™, perhaps because they have better access to the necessary growth factors. Structurally, organoids according to the invention are often elongated in shape. They may include one or more budding structure—a single cell epithelial layer which has a structure not unlike a bile duct. Under confocal microscopy, the structures may stain positive for keratin. They may include cells with polarised nuclei and small cytoplasm. The organoids may have a section which is formed of multiple layers; such cells often tend to have their nuclei more central to the cells, i.e. not polarized.

The cells in the multilayer section may organise themselves to include a gap, or lumen between the cells.

A liver organoid preferably comprises a hepatocyte and a cholangiocyte cell, more preferably wherein at least one of the following markers could be detected: at least one hepatocyte marker such as albumin, transthyretrin, B-1 integrin and Glutamine synthetase and/or at least one of CYP3A11, FAH, tbx3, TAT and Gck and/or at least one cholangiocyte maker such as Keratin 7 and 19. The skilled person knows how to detect each of these markers (i.e. RT-PCR and/or immunohistochemistry). Preferably the expression of each of these markers is assessed as carried out in the experimental part. Each of these markers is usually expressed after at least two weeks, three weeks or one month of culture using a method of the invention. Microarray analysis of the organoids in both culture conditions showed that liver organoids resemble adult liver tissue.

In some embodiments, approximately 35% of the cells in a liver organoid express a hepatocyte surface marker, for example, 25-45%, 30-40%, 33-37%, 35% or less, or 15-35% of cells.

Preferably, cells and organoids generated according to the invention also possess hepatocyte functions, such as expressing or staining positive for the mature hepatic markers albumin, B-1 integrin, CK-8, CK-18, transthyretin (TTR), glucose 6P, Met, Glutamine synthase (Glu1), transferrin, Fand1, Fand2a, K7, K19 and cytochrome P450 isoforms 3A13 (CYP3A13), 51 (CYP51) 2D10 (CYP2D10), 2j6 (CYP2j6), 39A1 (CYP39A1), 4A10 (CYP4A10), 4F13 (CYP4F13) 4F16 (CYP4F16), CYP4B1 and 20A1 (CYP20A1). Also, embryonic liver gene AFP is in some embodiments not detected in neither of both culture conditions, as in adult liver. In some embodiments, the expression of alpha fetal protein is just above the background gene expression.

Also, the well known liver transcription factors as HNF1a, HNF1b and HNF4a are highly expressed in both conditions.

Since liver and pancreas are closely related organs, we investigated whether our liver cultures also expressed pancreas-specific genes. The pancreas is functionally divided into endocrine and exocrine pancreas. The endocrine pancreas is mainly characterized for expressing insulin, glucagon and somatostatin. The expression of these hormones is tightly regulated by a set of endocrine pancreas-specific transcription factors, the most important being Pdx1 and NeuroD. The exocrine pancreas is formed by acinar and ductal compartments responsible of producing the digestive enzymes amylase, pancreatic lipase and chymotrypsin, among others. The expression of these genes is also regulated by specific exocrine pancreatic genes as Ptf1.

The pancreas specific genes Ptf1a, pancreatic amylase (Amy2a4), pancreatic lipase (Pnlip), insulin (ins1 and ins2), glucagon (Gcg), chymotrypsin (cela1), Pdx1 and NeuroD were absent in the liver cultures here described.

In some embodiments, one or more or all of the following genes are expressed in the liver organoids at a similar level to the corresponding gene in adult liver hepatocytes: Aqp1, Bmp2, Apo3, Apol7a, Sord, C3, Ppara, Pparg, tbx3, Igf1, 1117rb, 111b, Tgfbi, Apoa1, Apoa4, Apob, Cyp26b1, Cyp27a1, Cyp2b13, Cyp2b9, Cyp2c37, Cyp2f2, Cyp2g1, Cyp2j13, Cyp3a11, Cyp4a10 and Cypf14. For example, see FIG. 16A.

In some embodiments, one or more of the following genes is expressed in the liver organoids at a similarly shut down level compared to the corresponding gene in adult liver hepatocytes: Cc12, Osmr, Icam1 and Cxcl2.

In some embodiments, one or both of the following genes is differentially expressed in both a liver organoid and newborn liver: mKi67 and cdkn3.

In some embodiments, one, two or all of the following genes are expressed at a similar level in a liver organoid and a newborn liver: cyp2j6, olfm4 and Lefty 1. For example, see FIG. 16B.

In some embodiments, a liver organoid of the invention has a ductal phenotype when cultured in expansion medium of the invention (e.g. EM1 or EM2).

In some embodiments, a liver organoid of the invention expresses adult liver markers when cultured in a differentiation medium of the invention.

In one embodiment, a liver organoid of the invention has a gene expression profile as shown in FIG. 16C.

In a particularly preferred embodiment, a mouse liver cell population or organoid of the invention has the gene expression profile as shown in FIG. 18. For example, in one preferred embodiment, a mouse liver cell population or organoid of the invention:

a) expresses at least one (e.g. 1, 2, 3, 4, 5, 6, 7, 8, 9, 10, 11), preferably all of the following stem cell markers: lgr5, lgr4, epcam, Cd44, Tnfrsf19, Sox9, Spy, Cd24a, Prom1, Cdca7 and Elf3; and/or b) does not express the following stem cell marker: lgr6; and/or c) expresses at least one (e.g. 1, 2, 3, 4, 5, 6, 7, 8, 9, 10, 11, 12, 13, 14, 15, 16, 17, 18, 19), preferably all of the following hepatocyte or cholangiocyte markers when grown in expansion medium of the invention: Hnf1a, Hnf1b, Hnf4a, Hhex, Onecut1, Onecut2, Prox1, Cdh1, Foxa2, Gata6, Foxm1, Cebpa, Cebpb, Cebpd, Cebpg, Glu1, Krt7, Krt19 and Met; and/or d) does not express at least one (e.g. 1, 2, 3, 4, 5, 6, 7, 8, 9, 10, 11, 12, 13, 14, 15, 16, 17) of the following genes when grown in expansion medium of the invention: afp, Ins1, Ins2, Gcg, Ptf1a, Cela1, Cela2a, Cela3b, Neurod1, Neurod2, Neurog1, Neurog2, Neurog3, Amy2a4, Igf1r, Igf2 and Cd34; and/or e) expresses at least one (e.g. 1, 2 or 3) of the following reprogramming genes: Klf4, Myc and Pou5f1 and/or f) does not express the following reprogramming gene: Sox2.

wherein the expression of the genes is preferably detected by measuring expression at the mRNA level, for example, using a microarray.

More preferably a mouse liver cell population or organoid of the invention has all of features a) to f) above.

In some embodiments, the gene expression profile described above for a mouse cell population or organoid of the invention is for a mouse cell population or organoid cultured in expansion medium of the invention.

In some embodiments, there is provided a human liver cell population or organoid of the invention that has the gene expression signature shown in FIGS. 19A-E. For example, a human liver cell population or organoid cultured in EM1 of the invention preferably expresses the genes indicated in FIGS. 19A-E as being expressed in EM1 cell culture medium. For example, a human liver cell population or organoid cultured in EM2 of the invention preferably expresses the genes indicated in FIGS. 19A-E as being expressed in EM2 cell culture medium. For example, a human liver cell population or organoid cultured in DM of the invention preferably expresses the genes indicated in FIGS. 19A-E as being expressed in DM cell culture medium.

For example, in one preferred embodiment, a human liver cell population or organoid of the invention:

a) expresses at least one (e.g. 1, 2, 3, 4, 5, 6, 7, 8, 9), preferably all of the following stem cell signature genes: LGR4, TACSTD1/Epcam, CD44, SOX9, SP5, CD24, PROM1, CDCA7 and ELF3; and/or b) expresses at least one (e.g. 1, 2, 3, 4), preferably all of the following reprogramming genes: KLF4, MYC, POU5F1 and SOX2; and/or c) expresses at least one (e.g. 1, 2, 3, 4, 5, 6, 7, 8, 9, 10, 11, 12, 13, 14, 15, 16, 17, 18, 19), preferably all of the following hepatocyte/cholangiocyte specific genes: HNF1A, HNF1B, HNF4A, HHEX, ONECUT1, ONECUT2, PROX1, CDH1, FOXA2, GATA6, FOXM1, CEBPA, CEBPB, CEBPD, CEBPG, GLUL, KRT7, KRT19 and MET; and/or d) does not express at least one (e.g. 1, 2, 3, 4, 5, 6), preferably all of the following hepatocyte/cholangiocyte specific genes: NEUROG2, IGF1R and CD34, AFP, GCG and PTF1A, for example, it does not express NEUROG2, IGF1R and CD34; and/or e) expresses at least one (e.g. 1, 2, 3, 4, 5, 6, 7, 8, 9, 10, 11, 12, 13, 14, 15, 16, 17, 18), preferably all of the following hepatocyte specific genes: TTR, ALB, FAH, TAT, CYP3A7, APOA1, HMGCS1, PPARG, CYP2B6, CYP2C18, CYP2C9, CYP2J2, CYP3A4, CYP3A5, CYP3A7, CYP4F8, CYP4V2 and SCARB1;

wherein the expression of the genes is preferably detected by measuring expression at the mRNA level, for example, using a microarray.

More preferably a human liver cell population or organoid of the invention has all of features a) to e) above.

In some embodiments, the genes in a human liver cell population or organoid of the invention are upregulated or downregulated relative to expression of a reference RNA as shown in FIGS. 19A-E. Preferably, the reference RNA is Universal Human Reference RNA (Stratagene, Catalog #740000). In some embodiments, a gene is upregulated or downregulated relative to the reference RNA if it is also shown in FIGS. 19A-E as being upregulated or downregulated relative to the reference RNA but the extent of upregulation or downregulation need not be the same. In other embodiments, the extent of upregulation or downregulation is +/−35%, +/−30%, +/−25%, +/−20%, +/−20%, +/−15%, +/−10%, +/−5%, +/−3 or approximately the same as shown in FIGS. 19A-E. In other embodiments, the absolute level of expression of the genes in a human organoid of the invention is +/−35%, +/−30%, +/−25%, +/−20%, +/−15%, +/−10%, +/−5%, +/−3% or approximately the same as shown in FIGS. 19A-E.

The human liver cell population or organoids of the invention also preferably express Lgr5 and/or Tnfrsf19, preferably both. In some embodiments, the human liver cell population or organoids, when cultured in expansion medium of the invention express Lgr5 and/or Tnfrsf19, preferably both. Preferably, expression of Lgr5 and/or Tnfrsfr19 is detected by RT PCR. In some embodiments, Lgr5 and/or Tnfrsf19 are present at much lower levels of expression in organoids or cells when cultured in the differentiation medium compared to their level of expression organoids or cells when cultured in the expansion medium (for example at least 2-fold, at least 3-fold, at least 4-fold, at least 5-fold, at least 10-fold, at least 15-fold lower).

Cells and organoids according to the present invention may preferably be capable of secreting albumin, for example, at a rate of between approximately 1 µg per hour per $10^6$ cells and 10 µg per hour per $10^6$ cells, preferably between 2 µg and 6 µg per hour per $10^6$ cells.

Furthermore, such cells and organoids may secrete urea. For example, in a 35 mm dish of cells, the activity of urea synthesis may be between 1 µg and 50 µg in 48 hours, preferably between 5 µg and 30 µg.

Cells and organoids according to the invention may show visible glycogen stores, for example, when stained. The capacity for cells and organoids according to the invention to synthesize glycogen actively can be tested by switching the culture media from low-glucose differentiation media to high-glucose DMEM supplemented with 10% FBS and 0.2 µM dexamethasone for two days.

Cells and organoids according to the invention may possess inducible cytochrome P450 activity (e.g. CYP1A). Such activity may be tested, for example, using an ethoxyresorufin-O-deethylase (EROD) assay (Cancer Res, 2001, 61: 8164-8170). For example, cells or organoids may be exposed to a P450 substrate such as 3-methylcholanthrene and the levels of EROD activity compared to control cells.

Morphologically, the cells appear hepatocyte-like.

A preferred liver organoid comprises or consists of a cystic structure with on the outside a layer of cells with buds and a central lumen as depicted in FIGS. 2A-B. This liver organoid may have one or more (e.g. 2, 3, or all 4) of the following characteristics: (a) having a cell density of >$5\times10^5$ cells/cm$^3$, preferably >$10\times10^5$ cells/cm$^3$; (b) having a thickness equivalent to 2-30 layers of cells, preferably a thickness equivalent to 2-15 layers of cells; (c) the cells mutually contact in three dimensions, (d) demonstrate a function inherent to healthy liver tissue, (e) have an elongated shape, with 2 defined domains, i.e. a single layered epithelial domain where highly polarized cells are detected and keratin markers are expressed (this domain resembles the bile duct domain) and the other domain constitutes the main body of the organoid and is formed by a multilayered epithelia with non-polarized cells wherein albumin expression may be detected. It is clear to the skilled person that such a liver organoid is preferably not a liver fragment and/or does not comprise a blood vessel, and/or does not comprise a liver lobule or a bile duct.

Within the context of the invention, a liver fragment is a part of an adult liver, preferably a human adult liver. Preferably a liver organoid as identified herein is therefore not a liver fragment. A liver organoid is preferably obtained using a cell from an adult liver, preferably an epithelial stem cell from an adult liver, more preferably an epithelial stem cell from an adult liver expressing Lgr5.

In some embodiments, a liver organoid comprises cells that express Lgr5. For example, in some embodiments, at least 2%, more preferably at least 5%, at least 10%, at least 20%, at least 30%, at least 40%, at least 50%, at least 60%, at least 70%, at least 80%, at least 90%, at least 95% of the cells in the liver organoid express Lgr5. Similarly, the invention provides a cell or a population of cells which express Lgr5, wherein said cells are obtained from a liver organoid of the invention. The progeny of such cells is also encompassed by the invention.

In an embodiment, a liver organoid is a liver organoid which is still being cultured using a method of the invention and is therefore in contact with an extracellular matrix. Preferably, a liver organoid is embedded in a non-mesenchymal extracellular matrix. Within the context of the invention, "in contact" means a physical or mechanical or chemical contact, which means that for separating said liver organoid from said extracellular matrix a force needs to be used.

In a preferred embodiment, a liver organoid could be cultured during at least 2, 3, 4, 5, 6, 7, 8, 9, 10 weeks or 1, 2, 3, 4, 5, 6, 7, 8, 9, 10 months or longer.

In another preferred embodiment, a liver organoid originates from a single cell, preferably expressing Lgr5, more preferably wherein the single cell comprises a nucleic acid construct comprising a nucleic acid molecule of interest.

The invention further provides the use of a culture medium according to the invention for culturing epithelial stem cells or isolated organoid structures that comprise these stem cells on an extracellular matrix, whereby said stem cells preferably do not comprise human embryonic stem cells. Preferred are human adult stem cells. Furthermore, single sorted epithelial stem cells from the liver are also able to initiate these 3 dimensional organoids in a culture medium according to the invention. The invention further provides the use of a culture medium according to the invention for culturing liver fragments comprising stem cells.

It is preferred that said stem cells are liver stem cells, or epithelial stem cells. A culture medium according to the invention allowed the establishment of long-term culture conditions under which a liver organoid is formed in which all differentiated cell types are present. Using a culture method according to the invention allowed culture periods of at least seven months, at least eight months, at least nine months, at least ten months.

The invention further provides a liver organoid, preferably comprising at least 50% viable cells, more preferred at least 60% viable cells, more preferred at least 70% viable cells, more preferred at least 80% viable cells, more preferred at least 90% viable cells. Viability of cells may be assessed using Hoechst staining or Propidium Iodide staining in FACS.

The viable cells preferably possess hepatic functions, or characteristics of hepatocytes, as described above.

Uses of Cells and Organoids of the Invention

In a further aspect, the invention provides the use of a liver cell or organoid according to the invention as described above in a drug discovery screen, toxicity assay or in regenerative medicine. The invention furthermore provides the use of the progeny of liver organoids of the invention, in toxicity assays. Such toxicity assays may be in vitro assays using a cell derived from a liver organoid or a liver organoid or part thereof. Such progeny and liver organoids are easy to culture and more closely resemble primary epithelial cells than, for example, epithelial cell lines such as Caco-2 (ATCC HTB-37), I-407 (ATCC CCL6), and XBF (ATCC CRL 8808) which are currently used in toxicity assays. It is anticipated that toxicity results obtained with liver organoids more closely resemble results obtained in patients. A cell-based toxicity test is used for determining organ specific cytotoxicity. Compounds that are tested in said test comprise cancer chemopreventive agents, environmental chemicals, food supplements, and potential toxicants. The cells are exposed to multiple concentrations of a test agent for certain period of time. The concentration ranges for test agents in the assay are determined in a preliminary assay using an exposure of five days and log dilutions from the highest soluble concentration. At the end of the exposure period, the cultures are evaluated for inhibition of growth. Data are analyzed to determine the concentration that inhibited end point by 50 percent (TC50).

For example, induction of cytochrome P450 enzymes in liver hepatocytes is a key factor that determines the efficacy and toxicity of drugs. In particular, induction of P450s is an important mechanism of troublesome drug-drug interactions, and it is also an important factor that limits drug efficacy and governs drug toxicity. Cytochrome P450 induction assays have been difficult to develop, because they require intact normal human hepatocytes. These cells have proven intractable to production in numbers sufficient to sustain mass production of high throughput assays.

For example, according to this aspect of the invention, a candidate compound may be contacted with cell or organoid as described herein, and any change to the cells or in to activity of the cells may be monitored. Examples of other non-therapeutic uses of the cells or organoids of the present invention include research of liver embryology, liver cell lineages, and differentiation pathways; gene expression studies including recombinant gene expression; mechanisms involved in liver injury and repair; research of inflammatory and infectious diseases of the liver; studies of pathogenetic mechanisms; and studies of mechanisms of liver cell transformation and aetiology of liver cancer.

For high-throughput purposes, said liver organoids are cultured in multiwell plates such as, for example, 96 well plates or 384 well plates. Libraries of molecules are used to identify a molecule that affects said organoids. Preferred libraries comprise antibody fragment libraries, peptide phage display libraries, peptide libraries (e.g. LOPAP™, Sigma Aldrich), lipid libraries (BioMol), synthetic compound libraries (e.g. LOP AC™, Sigma Aldrich) or natural compound libraries (Specs, TimTec). Furthermore, genetic libraries can be used that induce or repress the expression of one of more genes in the progeny of the adenoma cells. These genetic libraries comprise cDNA libraries, antisense libraries, and siRNA or other non-coding RNA libraries. The cells are preferably exposed to multiple concentrations of a test agent for certain period of time. At the end of the exposure period, the cultures are evaluated. The term "affecting" is used to cover any change in a cell, including, but not limited to, a reduction in, or loss of, proliferation, a morphological change, and cell death. Said liver organoids can also be used to identify drugs that specifically target epithelial carcinoma cells, but not said liver organoids.

Liver organoids according to the invention can further replace the use of cell lines such as Caco-2 cells in toxicity assays of potential novel drugs or of known or novel food supplements.

Furthermore, such liver organoids can be used for culturing of a pathogen.

Cultures comprising liver organoids are useful in regenerative medicine, for example in post-radiation and/or post-surgery repair of the liver epithelium, in the repair of the epithelium in patients suffering from chronic or acute liver failure or disease. Liver diseases include, but are not limited to Hepatocellular Carcinoma, Alagille Syndrome, Alpha-1-Antitrypsin Deficiency, Autoimmune Hepatitis, Biliary Atresia, Chronic Hepatitis, Cancer of the Liver, Cirrhosis Liver Cysts Fatty Liver, Galactosemia Gilbert's Syndrome, Primary Biliary Cirrhosis, Hepatitis A, Hepatitis B, Hepatitis C, Primary Sclerosing Cholangitis, Reye's Syndrome, Sarcoidosis, Tyrosinemia, Type I Glycogen Storage Disease, Wilson's Disease, Neonatal Hepatitis, Non-alchoholic Steato-Hepatitis, Porphyria, and Hemochromatosis.

Genetic conditions that lead to liver failure could benefit from cell-based therapy in the form of partial or full cell replacement using cells cultured according to the media and/or methods of the invention. A non-limiting list of genetic conditions that lead to liver failure includes: Progressive familial intrahepatic cholestasis, Glycogen storage disease type III, Tyrosinemia, Deoxyguanosine kinase deficiency, Pyruvate carboxylase deficiency, Congenital dyserythropoietic anemia, Polycystic Liver Disease Polycystic Kidney Disease, Alpha-1 antitrypsine deficiency, Ureum cycle defects, Organic acidemiea, lysosomal storage diseases, and Fatty Acid Oxydation Disorders. Other conditions that may also benefit from cell-based therapy include Wilson's Disease and Hereditary Amyloidosis (FAP).

Other non-hepatocyte related causes of liver failure that would require a full liver transplant to reach full therapeutic effect, may still benefit from some temporary restoration of function using cell-based therapy using cells cultured according to the media and/or methods of the invention. A non-limiting list of examples of such conditions includes: Primary Biliary Cirrhosis, Primary Sclerosing Cholangitis, Aglagille syndrome, Homozygous Familial hypercholesterolemia, Hepatitis B with cirrhosis, Hepatitis C with cirrhosis, Budd-Chiari syndrome, Primary hyperoxaluria, Autoimmune Hepatitis, and Alcoholic liver disease.

The liver organoids of the invention may be used in a method of treating a hereditary disease that involves malfunctioning hepatocytes. Such diseases may be early onset or late onset. Early onset disease include metabolite related organ failure (e.g. alpha-1-antitrypsin deficiency), glycogen storage diseases (e.g. GSD II, Pompe's disease), tyrosinemia, mild DGUOK, CDA type I, Ureum cycle defects (e.g. OTC deficiency), organic academia and fatty acid oxidation disorders. Late onset diseases include primary hyperoxaluria, familial hypercholesterolemia, Wilson's disease, Hereditary Amyloidosis and Polycystic liver disease. Partial or full replacement with healthy hepatocytes arising from liver organoids of the invention may be used to restore liver function or to postpone liver failure.

The liver organoids of the invention may be used in a method of treating chronic liver failure arising due to hereditary metabolic disease or as a result of hepatocyte infection. Treatment of a hereditary metabolic disease may involve administration of genetically modified autologous liver organoids of the invention. Treatment of hepatocyte infections may involve administration of allogeneic liver organoids of the invention. In some embodiments, the liver organoids are administered over a period of 2-3 months.

The liver organoids of the invention may be used to treat acute liver failure, for example, as a result of liver intoxication which may result from use of paracetamol, medication or alcohol. In some embodiments, the therapy to restore liver function will comprise injecting hepatocyte suspension from frozen, ready to use allogenic hepatocytes obtained from organoids of the invention. The ability to freeze suitable organoids means that the organoids can be available for immediate delivery and so it is not necessary to wait for a blood transfusion.

In the case of replacement or correction of deficient liver function, it may be possible to construct a cell-matrix structure from one or more liver organoids generated according to the present invention. It is thought that only about 10% of hepatic cell mass is necessary for adequate function. This makes implantation of organoid unit compositions into children especially preferable to whole organ transplantation, due to the relatively limited availability of donors and smaller size of juvenile organs. For example, an 8-month-old child has a normal liver that weighs approximately 250 g. That child would therefore need about 25 g of tissue. An adult liver weighs-approximately 1500 g; therefore, the required implant would only be about 1.5% of the adult liver. When organoid units according to the invention are implanted, optionally attached to a polymer scaffold, proliferation in the new host will occur, and the resulting hepatic cell mass replaces the deficient host function. The inventors have shown, for the first time, that it is possible to generate mature hepatocytes from adult liver stem cells or liver tissue fragments comprising stem cells that are suitable for transplantation into non-human animals or humans. Using the first culture medium according to the invention, the inventors have demonstrated that it is possible to maintain and expand a population of liver stem cells. Using the second culture medium according to the invention, the inventors have shown that hepatoblasts can be differentiated in vivo to mature hepatocytes suitable for transplantation purposes. Hence, the inventors provide a new source of hepatocytes for liver regeneration, replacement or correction of deficient liver function.

The inventors have also demonstrated successful transplantation of the organoids, grown by methods of the present invention, into immunodeficient mice (see example 7), with transplanted organoid-derived cells generating both cholangyocytes and hepatocytes in vivo. Therefore, in one embodiment the invention provides organoids or organoid-derived cells of the invention for transplanting into human or animals.

The use of human liver organoids for transplantation purposes is advantageous over the use of fetal or adult hepatocytes for a number of reasons. Firstly, the culture methods of the invention provide unlimited expansion of cells and hence, an unlimited supply. In particular, the inventors have shown that under the correct culture conditions (e.g. using the expansion culture medium of the invention), that Lgr5+ cells can undergo more than 1000 divisions in vitro. Therefore, Lgr5+ cells can be extracted from the liver organoids and repassaged providing a continual self-renewing source of transplantable hepatocyte and cholangyocyte-generating cells. By contrast, fetal or adult hepatocytes are derived from donor livers which only provide a single round of transplantation. Furthermore, donor cells can only be kept alive for a few days but lose their hepatocyte properties. This means the transplants must be made as soon as the donor becomes available. Organoid-derived cells, on the other hand, retain their phenotype over multiple divisions and over prolonged periods of time meaning that they are ready and available for transplantation at any stage. This could also allow the organoid-derived cells to be used as a temporary liver treatment to extend the lifespan of patients for patients on the waiting list for liver transplants. A further advantage of the liver organoids of the invention is that they can be frozen and later be defrosted without loss of function. This enables cell banking, easy storage and rapid availability for acute use. This could be useful for example, in the preparation of an "off-the-shelf" product that might be used for the treatment of acute liver toxicity. Organoids can also be grown from cells or tissue fragments taken as small biopsies from live donors minimising any ethical objections to the treatment. The donor may even be from the patient that is to be treated, which could reduce any negative side-effects associated with transplantation of foreign cells and organs and reduce the need for immunosuppressive drugs.

Accordingly, included within the scope of the invention are methods of treatment of a human or animal patient through cellular therapy. The term "animal" here denotes all mammalian animals, preferably human patients. It also includes an individual animal in all stages of development, including embryonic and foetal stages. For example, the patient may be an adult, or the therapy may be for pediatric use (e.g. newborn, child or adolescent). Such cellular therapy encompasses the administration of cells or organoids generated according to the invention to a patient through any appropriate means. Specifically, such methods of treatment involve the regeneration of damaged tissue. The term "administration" as used herein refers to well recognized forms of administration, such as intravenous or injection, as well as to administration by transplantation, for example transplantation by surgery, grafting or transplantation of tissue engineered liver derived from cells or organoids according to the present invention. In the case of cells, systemic administration to an individual may be possible, for example, by infusion into the superior mesenteric artery, the celiac artery, the subclavian vein via the thoracic duct, infusion into the heart via the superior vena cava, or infusion into the peritoneal cavity with subsequent migration of cells via subdiaphragmatic lymphatics, or directly into liver sites via infusion into the hepatic arterial blood supply or into the portal vein.

Between $10^4$ and $10^{13}$ cells per 100 kg person may be administered per infusion. Preferably, between about $1-5\times 10^4$ and $1-5\times 10^7$ cells may be infused intravenously per 100 kg person. More preferably, between about $1\times 10^4$ and $10\times 10^6$ cells may be infused intravenously per 100 kg person. In some embodiments, a single administration of cells or organoids is provided. In other embodiments, multiple administrations are used. Multiple administrations can be provided over an initial treatment regime, for example, of 3-7 consecutive days, and then repeated at other times.

In some embodiments it is desirable to repopulate/replace 10-20% of a patient's liver with healthy hepatocytes arising from a liver organoid of the invention.

It is also possible to reconstitute a liver organoid from one single cell expressing Lgr5 as defined herein. This single cell may have been modified by introduction of a nucleic acid construct as defined herein, for example, to correct a genetic deficiency or mutation. It would also be possible to specifically ablate expression, as desired, for example, using siRNA. Potential polypeptides to be expressed could be any of those that are deficient in metabolic liver diseases, including, for example, AAT (alpha antitrypsin). For elucidating liver physiology, we might also express or inactivate genes implicated in the Wnt, EGF, FGF, BMP or notch pathway. Also, for screening of drug toxicity, the expression or inactivation of genes responsible for liver drug metabolism (for example, genes in the CYP family) would be of high interest In one embodiment, the expanded epithelial stem cells may be reprogrammed into related tissue fates such as, for example, liver cells including a hepatocyte and a cholangiocyte cell. Thus far, it has not been possible to regenerate liver cells from adult stem cells. The culturing methods of the present invention will enable to analyse for factors that trans-differentiate the closely related epithelial stem cell to a liver cell, including a hepatocyte and a cholangiocyte cell.

It will be clear to a skilled person that gene therapy can additionally be used in a method directed at repairing damaged or diseased tissue. Use can, for example, be made of an adenoviral or retroviral gene delivery vehicle to deliver genetic information, like DNA and/or RNA to stem cells. A skilled person can replace or repair particular genes targeted in gene therapy. For example, a normal gene may be inserted into a nonspecific location within the genome to replace a non functional gene. In another example, an abnormal gene sequence can be replaced for a normal gene sequence through homologous recombination. Alternatively, selective reverse mutation can return a gene to its normal function. A further example is altering the regulation (the degree to which a gene is turned on or off) of a particular gene. Preferably, the stem cells are ex vivo treated by a gene therapy approach and are subsequently transferred to the mammal, preferably a human being in need of treatment. For example, organoid-derived cells may be genetically modified in culture before transplantation into patients.

The inventors have found that Lgr5 is not detectable in healthy liver, although residual Lgr5 may be detected. Thus, the invention further provides a method of diagnosing liver injury comprising detecting whether Lgr5 is expressed, wherein the expression of Lgr5 protein indicates liver injury. The invention also provides a method of monitoring the repair or regeneration of the liver by monitoring the expression of Lgr5 in the liver. Lgr5 expression may be detected by any suitable method, for example, flow cytometry, immunohistochemistry or by use of PCR methods.

The invention also provides a composition or cell culture vessel comprising cells and/or organoids according to any one of the aspects of the invention described above, and a culture medium according to any one of the aspects of the invention described above. For example, such a composition or cell culture vessel may comprise any number of cells or organoids cultured according to a method of the invention, in a culture medium as described above. For example, a preferred culture medium comprises or consists of Advanced-DMEM/F12 supplemented with B27, N2, 200 ng/ml N-Acetylcysteine, 50 ng/ml EGF, 1 µg/ml R-spondin 1, 10 nM gastrin, 100 ng/ml FGF10, 10 mM Nicotinamide and 50 ng/ml HGF and 50% Wnt conditioned media.

DEFINITIONS

A nucleic acid construct comprises a nucleic acid molecule of interest and will ensure expression of the given nucleic acid molecule in the cells wherein it had been introduced. A particularly preferred nucleic acid construct is an expression vector wherein a nucleic acid molecule encoding a polypeptide is operably linked to a promoter capable of directing expression of said nucleic acid molecule (i.e a coding sequence) in said cells. The phrase "expression vector" generally refers to a nucleic acid molecule that is capable of effecting expression of a gene/nucleic acid molecule it contains in a cell compatible with such sequences. These expression vectors typically include at least suitable promoter sequences and optionally, transcription termination signals. A nucleic acid or DNA or nucleotide sequence encoding a polypeptide is incorporated into a DNA/nucleic acid construct capable of introduction into and expression in an in vitro cell culture as identified in a method of the invention. A DNA construct prepared for introduction into a particular cell typically include a replication system recognized by said cell, an intended DNA segment encoding a desired polypeptide, and transcriptional and translational initiation and termination regulatory sequences operably linked to the polypeptide-encoding segment. A DNA segment is "operably linked" when it is placed into a functional relationship with another DNA segment. For example, a promoter or enhancer is operably linked to a coding sequence if it stimulates the transcription of the sequence. DNA for a signal sequence is operably linked to DNA encoding a polypeptide if it is expressed as a preprotein that participates in the secretion of a polypeptide. Generally, a DNA sequence that is operably linked are contiguous, and, in the case of a signal sequence, both contiguous and in reading phase. However, enhancers need not be contiguous with a coding sequence whose transcription they control. Linking is accomplished by ligation at convenient restriction sites or at adapters or linkers inserted in lieu thereof.

The selection of an appropriate promoter sequence generally depends upon the host cell selected for the expression of a DNA segment. Examples of suitable promoter sequences include eukaryotic promoters well known in the art (see, e.g. Sambrook and Russell, 2001, supra). A transcriptional regulatory sequence typically includes a heterologous enhancer or promoter that is recognised by the cell. Suitable promoters include the CMV promoter. An expression vector includes the replication system and transcriptional and translational regulatory sequences together with the insertion site for the polypeptide encoding segment can be employed. Examples of workable combinations of cell lines and expression vectors are described in Sambrook and Russell (2001, supra) and in Metzger et al. (1988) Nature 334: 31-36.

The invention is not limited to a specific polypeptide or nucleic acid molecule of interest to be expressed in a cell expressing Lgr5 as identified herein. Depending on the aim of the method, one may envisage to express a polypeptide in a liver cell and/or to inactivate the expression of a polypeptide in a liver cell. Potential polypeptides to be expressed could be all of those that are deficient in metabolic liver diseases, as eg AAT (alpha antitrypsin). For elucidating the liver physiology, we might also express or inactivate genes implicated in the Wnt, EGF, FGF, BMP or notch pathway. Also, for screening of drug toxicity, the expression or inactivation of genes responsible for liver drug metabolism (e.g. genes of the CYP family) would be of high interest.

Some aspects of the invention concern the use of a nucleic acid construct or expression vector comprising a nucleotide sequence as defined above, wherein the vector is a vector that is suitable for gene therapy. Vectors that are suitable for gene therapy are described in Anderson 1998, Nature 392: 25-30; Walther and Stein, 2000, Drugs 60: 249-71; Kay et al., 2001, Nat. Med. 7: 33-40; Russell, 2000, J. Gen. Virol. 81: 2573-604; Amado and Chen, 1999, Science 285: 674-6; Federico, 1999, Curr. Opin. Biotechnol. 10: 448-53; Vigna and Naldini, 2000, J. Gene Med. 2: 308-16; Marin et al., 1997, Mol. Med. Today 3: 396-403; Peng and Russell, 1999, Curr. Opin. Biotechnol. 10: 454-7; Sommerfelt, 1999, J. Gen. Virol. 80: 3049-64; Reiser, 2000, Gene Ther. 7: 910-3; and references cited therein. Examples include integrative and non-integrative vectors such as those based on retroviruses, adenoviruses (AdV), adeno-associated viruses (AAV), lentiviruses, pox viruses, alphaviruses, and herpes viruses.

A particularly suitable gene therapy vector includes an Adenoviral (Ad) and Adeno-associated virus (AAV) vector. These vectors infect a wide number of dividing and non-dividing cell types including liver cells. In addition adenoviral vectors are capable of high levels of transgene expression. However, because of the episomal nature of the adenoviral and AAV vectors after cell entry, these viral vectors are most suited for therapeutic applications requiring only transient expression of the transgene (Russell, 2000, J. Gen. Virol. 81: 2573-2604; Goncalves, 2005, Virol J. 2(1): 43) as indicated above. Preferred adenoviral vectors are modified to reduce the host response as reviewed by Russell (2000, supra). Safety and efficacy of AAV gene transfer has been extensively studied in humans with encouraging results in the liver, muscle, CNS, and retina (Manno et al Nat medicine 2006, Stroes et al ATVB 2008, Kaplitt, Feigin, Lancet 2009; Maguire, Simonelli et al NEJM 2008; Bainbridge et al NEJM 2008). AAV2 is the best characterized serotype for gene transfer studies both in humans and experimental models. AAV2 presents natural tropism towards skeletal muscles, neurons, vascular smooth muscle cells and hepatocytes. AAV2 is therefore a good choice of vector to target liver tissues. Other examples of adeno-associated virus-based non integrative vectors include AAV1, AAV3, AAV4, AAV5, AAV6, AAV7, AAV8, AAV9, AAV10, AAV11 and pseudotyped AAV. The use of non-human serotypes, like AAV8 and AAV9, might be useful to overcome these immunological responses in subjects, and clinical trials have just commenced (ClinicalTrials.gov Identifier: NCT00979238). For gene transfer into a liver cell, an adenovirus serotype 5 or an AAV serotype 2, 7 or 8 have been shown to be effective vectors and therefore a preferred Ad or AAV serotype (Gao, Molecular Therapy (2006) 13, 77-87).

A preferred retroviral vector for application in the present invention is a lentiviral based expression construct. Lentiviral vectors have the unique ability to infect non-dividing cells (Amado and Chen, 1999 Science 285: 674-6). Methods for the construction and use of lentiviral based expression constructs are described in U.S. Pat. Nos. 6,165,782, 6,207, 455, 6,218,181, 6,277,633 and 6,323,031 and in Federico (1999, Curr Opin Biotechnol 10: 448-53) and Vigna et al. (2000, J Gene Med 2000; 2: 308-16).

Generally, gene therapy vectors will be as the expression vectors described above in the sense that they comprise a nucleotide sequence encoding a polypeptide of the invention to be expressed, whereby a nucleotide sequence is operably linked to the appropriate regulatory sequences as indicated above. Such regulatory sequence will at least comprise a promoter sequence. Suitable promoters for expression of a nucleotide sequence encoding a polypeptide from gene therapy vectors include e.g. cytomegalovirus (CMV) intermediate early promoter, viral long terminal repeat promoters (LTRs), such as those from murine moloney leukaemia virus (MMLV) rous sarcoma virus, or HTLV-1, the simian virus 40 (SV 40) early promoter and the herpes simplex virus thymidine kinase promoter. Suitable promoters are described below.

Several inducible promoter systems have been described that may be induced by the administration of small organic or inorganic compounds. Such inducible promoters include those controlled by heavy metals, such as the metallothionine promoter (Brinster et al. 1982 Nature 296: 39-42; Mayo et al. 1982 Cell 29: 99-108), RU-486 (a progesterone antagonist) (Wang et al. 1994 Proc. Natl. Acad. Sci. USA 91: 8180-8184), steroids (Mader and White, 1993 Proc. Natl. Acad. Sci. USA 90: 5603-5607), tetracycline (Gossen and Bujard 1992 Proc. Natl. Acad. Sci. USA 89: 5547-5551; U.S. Pat. No. 5,464,758; Furth et al. 1994 Proc. Natl. Acad. Sci. USA 91: 9302-9306; Howe et al. 1995 J. Biol. Chem. 270: 14168-14174; Resnitzky et al. 1994 Mol. Cell. Biol. 14: 1669-1679; Shockett et al. 1995 Proc. Natl. Acad. Sci. USA 92: 6522-6526) and the tTAER system that is based on the multi-chimeric transactivator composed of a tetR polypeptide, as activation domain of VP16, and a ligand binding domain of an estrogen receptor (Yee et al., 2002, U.S. Pat. No. 6,432,705).

Suitable promoters for nucleotide sequences encoding small RNAs for knock down of specific genes by RNA interference (see below) include, in addition to the above mentioned polymerase II promoters, polymerase III promoters. The RNA polymerase III (pol III) is responsible for the synthesis of a large variety of small nuclear and cytoplasmic non-coding RNAs including 5S, U6, adenovirus VA1, Vault, telomerase RNA, and tRNAs. The promoter structures of a large number of genes encoding these RNAs have been determined and it has been found that RNA pol III promoters fall into three types of structures (for a review see Geiduschek and Tocchini-Valentini, 1988 Annu. Rev. Biochem. 57: 873-914; Willis, 1993 Eur. J. Biochem. 212: 1-11; Hernandez, 2001, J. Biol. Chem. 276: 26733-36). Particularly suitable for expression of siRNAs are the type 3 of the RNA pol III promoters, whereby transcription is driven by cis-acting elements found only in the 5'-flanking region, i.e. upstream of the transcription start site. Upstream sequence elements include a traditional TATA box (Mattaj et al., 1988 Cell 55, 435-442), proximal sequence element and a distal sequence element (DSE; Gupta and Reddy, 1991 Nucleic Acids Res. 19, 2073-2075). Examples of genes under the control of the type 3 pol III promoter are U6 small nuclear RNA (U6 snRNA), 7SK, Y, MRP, H1 and telomerase RNA genes (see e.g. Myslinski et al., 2001, Nucl. Acids Res. 21: 2502-09).

A gene therapy vector may optionally comprise a second or one or more further nucleotide sequence coding for a second or further polypeptide. A second or further polypeptide may be a (selectable) marker polypeptide that allows for the identification, selection and/or screening for cells containing the expression construct. Suitable marker proteins for this purpose are e.g. the fluorescent protein GFP, and the selectable marker genes HSV thymidine kinase (for selection on HAT medium), bacterial hygromycin B phosphotransferase (for selection on hygromycin B), Tn5 aminoglycoside phosphotransferase (for selection on G418), and dihydrofolate reductase (DHFR) (for selection on methotrexate), CD20, the low affinity nerve growth factor gene. Sources for obtaining these marker genes and methods for their use are provided in Sambrook and Russel (2001) "Molecular Cloning: A Laboratory Manual ($3^{rd}$ edition), Cold Spring Harbor Laboratory, Cold Spring Harbor Laboratory Press, New York.

Alternatively, a second or further nucleotide sequence may encode a polypeptide that provides for fail-safe mechanism that allows a subject from the transgenic cells to be cured, if deemed necessary. Such a nucleotide sequence, often referred to as a suicide gene, encodes a polypeptide that is capable of converting a prodrug into a toxic substance that is capable of killing the transgenic cells in which the polypeptide is expressed. Suitable examples of such suicide genes include e.g. the *E. coli* cytosine deaminase gene or one of the thymidine kinase genes from Herpes Simplex Virus, Cytomegalovirus and Varicella-Zoster virus, in which case ganciclovir may be used as prodrug to kill the IL-10 transgenic cells in the subject (see e.g. Clair et al., 1987, Antimicrob. Agents Chemother. 31: 844-849).

For knock down of expression of a specific polypeptide, a gene therapy vector or other expression construct is used for the expression of a desired nucleotide sequence that preferably encodes an RNAi agent, i.e. an RNA molecule that is capable of RNA interference or that is part of an RNA molecule that is capable of RNA interference. Such RNA molecules are referred to as siRNA (short interfering RNA, including e.g. a short hairpin RNA). Alternatively, a siRNA molecule may directly, e.g. in a pharmaceutical composition that is administered within or in the neighborhood of a cell expressing Lgr5, or of a liver cell (i.e. hepatocyte or cholangiocyte) or of a liver organoid.

A desired nucleotide sequence comprises an antisense code DNA coding for the antisense RNA directed against a region of the target gene mRNA, and/or a sense code DNA coding for the sense RNA directed against the same region of the target gene mRNA. In a DNA construct of the invention, an antisense and sense code DNAs are operably linked to one or more promoters as herein defined above that are capable of expressing an antisense and sense RNAs, respectively. "siRNA" preferably means a small interfering RNA that is a short-length double-stranded RNA that are not toxic in mammalian cells (Elbashir et al., 2001, Nature 411: 494-98; Caplen et al., 2001, Proc. Natl. Acad. Sci. USA 98: 9742-47). The length is not necessarily limited to 21 to 23 nucleotides. There is no particular limitation in the length of siRNA as long as it does not show toxicity. "siRNAs" can be, e.g. at least 15, 18 or 21 nucleotides and up to 25, 30, 35 or 49 nucleotides long. Alternatively, the double-stranded RNA portion of a final transcription product of siRNA to be expressed can be, e.g. at least 15, 18 or 21 nucleotides and up to 25, 30, 35 or 49 nucleotides long.

"Antisense RNA" is preferably an RNA strand having a sequence complementary to a target gene mRNA, and thought to induce RNAi by binding to the target gene mRNA. "Sense RNA" has a sequence complementary to the antisense RNA, and annealed to its complementary antisense RNA to form siRNA. The term "target gene" in this context preferably refers to a gene whose expression is to be silenced due to siRNA to be expressed by the present system, and can be arbitrarily selected. As this target gene, for example, genes whose sequences are known but whose functions remain to be elucidated, and genes whose expressions are thought to be causative of diseases are preferably selected. A target gene may be one whose genome sequence has not been fully elucidated, as long as a partial sequence of mRNA of the gene having at least 15 nucleotides or more, which is a length capable of binding to one of the strands (antisense RNA strand) of siRNA, has been determined. Therefore, genes, expressed sequence tags (ESTs) and portions of mRNA, of which some sequence (preferably at least 15 nucleotides) has been elucidated, may be selected as the "target gene" even if their full length sequences have not been determined.

The double-stranded RNA portions of siRNAs in which two RNA strands pair up are not limited to the completely paired ones, and may contain nonpairing portions due to mismatch (the corresponding nucleotides are not complementary), bulge (lacking in the corresponding complementary nucleotide on one strand), and the like. A non-pairing portions can be contained to the extent that they do not interfere with siRNA formation. The "bulge" used herein preferably comprise 1 to 2 non-pairing nucleotides, and the double-stranded RNA region of siRNAs in which two RNA strands pair up contains preferably 1 to 7, more preferably 1 to 5 bulges. In addition, the "mismatch" used herein is preferably contained in the double-stranded RNA region of siRNAs in which two RNA strands pair up, preferably 1 to 7, more preferably 1 to 5, in number. In a preferable mismatch, one of the nucleotides is guanine, and the other is uracil. Such a mismatch is due to a mutation from C to T, G to A, or mixtures thereof in DNA coding for sense RNA, but not particularly limited to them. Furthermore, in the present invention, a double-stranded RNA region of siRNAs in which two RNA strands pair up may contain both bulge and mismatched, which sum up to, preferably 1 to 7, more preferably 1 to 5 in number. Such non-pairing portions (mismatches or bulges, etc.) can suppress the below-described recombination between antisense and sense code DNAs and make the siRNA expression system as described below stable. Furthermore, although it is difficult to sequence stem loop DNA containing no non-pairing portion in the double-stranded RNA region of siRNAs in which two RNA strands pair up, the sequencing is enabled by introducing mismatches or bulges as described above. Moreover, siRNAs containing mismatches or bulges in the pairing double-stranded RNA region have the advantage of being stable in *E. coli* or animal cells.

The terminal structure of siRNA may be either blunt or cohesive (overhanging) as long as siRNA enables to silence the target gene expression due to its RNAi effect. The cohesive (overhanging) end structure is not limited only to the 3' overhang, and the 5' overhanging structure may be included as long as it is capable of inducing the RNAi effect. In addition, the number of overhanging nucleotide is not limited to the already reported 2 or 3, but can be any numbers as long as the overhang is capable of inducing the RNAi effect. For example, the overhang consists of 1 to 8, preferably 2 to 4 nucleotides. Herein, the total length of siRNA having cohesive end structure is expressed as the sum of the length of the paired double-stranded portion and that of a pair comprising overhanging single-strands at both ends. For example, in the case of 19 bp double-stranded RNA portion with 4 nucleotide overhangs at both ends, the total length is expressed as 23 bp. Furthermore, since this overhanging sequence has low specificity to a target gene, it is not necessarily complementary (antisense) or identical (sense) to the target gene sequence. Furthermore, as long as siRNA is able to maintain its gene silencing effect on the target gene, siRNA may contain a low molecular weight RNA (which may be a natural RNA molecule such as tRNA, rRNA or viral RNA, or an artificial RNA molecule), for example, in the overhanging portion at its one end.

In addition, the terminal structure of the "siRNA" is necessarily the cut off structure at both ends as described above, and may have a stem-loop structure in which ends of one side of double-stranded RNA are connected by a linker RNA (a "shRNA"). The length of the double-stranded RNA region (stem-loop portion) can be, e.g. at least 15, 18 or 21 nucleotides and up to 25, 30, 35 or 49 nucleotides long. Alternatively, the length of the double-stranded RNA region that is a final transcription product of siRNAs to be expressed is, e.g. at least 15, 18 or 21 nucleotides and up to 25, 30, 35 or 49 nucleotides long. Furthermore, there is no particular limitation in the length of the linker as long as it has a length so as not to hinder the pairing of the stem portion. For example, for stable pairing of the stem portion and suppression of the recombination between DNAs coding for the portion, the linker portion may have a clover-leaf tRNA structure. Even though the linker has a length that hinders pairing of the stem portion, it is possible, for example, to construct the linker portion to include introns so that the introns are excised during processing of precursor RNA into mature RNA, thereby allowing pairing of the stem portion. In the case of a stem-loop siRNA, either end (head or tail) of RNA with no loop structure may have a low molecular weight RNA. As described above, this low molecular weight RNA may be a natural RNA molecule such as tRNA, rRNA, snRNA or viral RNA, or an artificial RNA molecule.

To express antisense and sense RNAs from the antisense and sense code DNAs respectively, a DNA construct of the present invention comprise a promoter as defined above. The number and the location of the promoter in the construct can in principle be arbitrarily selected as long as it is capable of expressing antisense and sense code DNAs. As a simple example of a DNA construct of the invention, a tandem expression system can be formed, in which a promoter is located upstream of both antisense and sense code DNAs. This tandem expression system is capable of producing siRNAs having the aforementioned cut off structure on both ends. In the stem-loop siRNA expression system (stem expression system), antisense and sense code DNAs are arranged in the opposite direction, and these DNAs are connected via a linker DNA to construct a unit. A promoter is linked to one side of this unit to construct a stem-loop siRNA expression system. Herein, there is no particular limitation in the length and sequence of the linker DNA, which may have any length and sequence as long as its sequence is not the termination sequence, and its length and sequence do not hinder the stem portion pairing during the mature RNA production as described above. As an example, DNA coding for the above-mentioned tRNA and such can be used as a linker DNA.

In both cases of tandem and stem-loop expression systems, the 5' end may be have a sequence capable of promoting the transcription from the promoter. More specifically, in the case of tandem siRNA, the efficiency of siRNA production may be improved by adding a sequence capable of promoting the transcription from the promoters at the 5' ends of antisense and sense code DNAs. In the case of stem-loop siRNA, such a sequence can be added at the 5' end of the above-described unit. A transcript from such a sequence may be used in a state of being attached to siRNA as long as the target gene silencing by siRNA is not hindered. If this state hinders the gene silencing, it is preferable to perform trimming of the transcript using a trimming means (for example, ribozyme as are known in the art). It will be clear to the skilled person that an antisense and sense RNAs may be expressed in the same vector or in different vectors. To avoid the addition of excess sequences downstream of the sense and antisense RNAs, it is preferred to place a terminator of transcription at the 3' ends of the respective strands (strands coding for antisense and sense RNAs). The terminator may be a sequence of four or more consecutive adenine (A) nucleotides.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a product as defined herein may comprise additional component(s) than the ones specifically identified, said additional component(s) not altering the unique characteristic of the invention. In addition a method as defined herein may comprise additional step(s) than the ones specifically identified, said additional step(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one". The word "about" or "approximately" when used in association with a numerical value (about 10) preferably means that the value may be the given value of 10 more or less 1% of the value.

All patent and literature references cited in the present specification are hereby incorporated by reference in their entirety.

The following examples are offered for illustrative purposes only, and are not intended to limit the scope of the present invention in any way.

DESCRIPTION OF FIGURES

(FIG. 1A) DIC images of liver organoids maintained with EGF (E), R-spondin 1 (R), Noggin (N), Wnt3A conditioned media (W) or the combination of them, supplemented with FGF10, HGF and Nicotinamide. (FIG. 1B) The number of organoids was counted weekly and passaged when required. Results are shown as mean±SEM of 3 independent experiments. (FIG. 1C) gene expression analysis by RTPCR of Lgr5, Keratin 7 (K7) and Albumin (Alb) genes. (FIG. 1D) Isolated bibliary ducts growing into organoids. Differential interference contrast images from the corresponding days after seeding. Magnification 10× (days 0, 1, 3 and 5). Days 15 on magnification 4×. Cultures were passage every 4-7 days by mechanical dissociation. Cultures have been grown at least for 8 months.

(FIG. 2A) Upper panels: paraffin section of a mouse liver showing the different domains (PT=portal triad, CV=central vein). Lower panels: Paraffin section of a liver organoid showing different domains b (single layered epithelia) and h (stratified epithelia) (FIG. 2B) Right panel: Ecadherin staining in the liver organoids. Two different domains can be identified. Domain b, formed by a single layered epithelia that resembles the bile duct structures in the liver. This bile duct domain is formed by highly polarized cells that shows positive staining for pancytokeratin (PCK) (lower panel). Left panels show the presence of a second domain within the liver organoids. This h domain is formed by a stratified epithelia with non-polarized cells. The cells are organized around a central lumen and express the hepatocyte marker Alb. Magnification 10×.

(FIG. 4A) immunohistochemical and immunofluorescence analysis of the expression of the cholangiocyte marker keratin 7 (K7) and the hepatocyte markers keratin 8 (K8) and albumin (Alb). (FIG. 4B) analysis of the gene expression of hepatocyte markers: Albumin (Alb), transthyretrin (Ttr), Glutamine synthetase (Glu1), glucose 6 phosphatase (G6P) and Cytocrome p450 isoform 3A11 (CYP3A11); and cholangiocyte markers keratin 7 (K7) and Keratin 19 (K19).

(FIG. 5A) flow cytometry plot indicating the area of the sorted cells. (FIG. 5B) single cell growing into organoids at the time points indicated. Magnification 40×(day 1-3), 10× (day 16), 4×(day 21-on). (FIGS. 5C-D) representative image of the colony formation efficiency of a Lgr5GFP single sorted cells. 100 cells were seeded in triplicate and colonies were counted 10 days later.

(FIG. 6A) hit map analysis showing that the cultures present a similar profile to the adult liver but a different profile to non-liver related tissues as muscle and BAT and WAT, (FIG. 6B) List of hepatocyte markers and cholangyocyte markers in the different conditions.

FIGS. 7A-B: Mouse liver organoid culture shows stable karyotyping after long-term culture.

FIG. 7A—DIC images of liver organoids maintained in EGF (E) and R-spondin 1 (R), supplemented with FGF10, HGF and Nicotinamide (left figure, ER) or maintained in the same combination supplemented with Noggin (N) and Wnt3A conditioned media (W) (right figure, ENRW) for a period of 24 months.

FIG. 7B—Karyotype analysis of mouse liver organoids after 8 months in culture. Normal chromosomal counts (n=40, left panel figure) and polyploidy, a typical hepatocyte feature, were found (n=80, right panel figure)

FIG. 8A—Diagram depicting the genes differentially expressed during the 3 stages of liver development, from hepatoblast to mature hepatocyte.

FIG. 8B—Scheme showing the protocol used. Cultures were seeded in expansion medium EM2 (ERFHNic: EGF (E) and R-spondin 1 (R), supplemented with FGF10, HGF and Nicotinamide; ERFHNic is indicated as 'ER' in FIG. 8B) 2 days prior the experiment. Two days later, culture media was changed to either EGF (E) alone or EGF supplemented with R-spondin 1 (ER) with or without additional supplements chosen from FGF10 (F) or HGF (H) or Nicotinamide (Nic) or a combination of these at the concentrations stated in the text. Five days later cultures were split and replated at 1:4 ratio for each condition. Under these conditions, cultures have been split and replated every 7 days for a total period of 10 weeks FIG. 8C—First day after first split in each of the culture conditions tested. Results shows that EGF and R-spondin 1 combined with FGF10 or HGF or Nicotinamide or a combination of these are essential to achieve at least 1 passage.

FIG. 8D—After long-term culture, the combination of ER supplemented with FNic or ER supplemented with FHNic, both result in high passage numbers. After passage 10, the growth rate is better for the culture condition including the 3 supplemental factors; ERFHNic (FIGS. 15 A-B).

FIG. 8E—RT-PCR analysis showing the expression of different hepatocyte markers (CYP3A11, Alb, FAH) and cholangiocyte marker (K19) and stem cell marker IGR5 5 days after the withdrawal of certain factors (starting point was ERFHNic). Note that only the condition EF showed expression of all hepatocyte markers tested. HPRT was used as a housekeeping gene to normalize for gene expression.

FIG. 9: Table showing the quantification of different hepatocyte and cholangiocyte specific transcription factors in cells from three different liver culture conditions and in adult liver tissue. Also shown is the expression of the key components of the Notch and TGF-beta signalling pathways. E=EFHNic, ER=ERFHNic, ENRW=ENRWFHNic.

FIGS. 10A-F: Differentiation protocol

FIG. 10A—Scheme showing the protocol used. Cultures were seeded in expansion medium (ERFHNic: EGF (E) and R-spondin 1 (R), supplemented with FGF10, HGF and Nicotinamide; ERFHNic is indicated as 'ER' in FIG. 10A 2 days prior to the experiment. Two days later, culture media was changed to EGF (E) supplemented with either A8301 (A), or DAPT (D), or FGF10 (F) or HGF (H) or Nicotinamide (Nic) or R-spondin 1 (R) or Wnt3A or Noggin (N) or a combination of these at the concentrations shown. RNA was isolated at several time points. Mouse liver tissue was taken as positive control (+) whereas water was taken as negative control (−).

FIG. 10B—RT-PCR analysis showing the expression of the hepatocyte markers CYP3A11, Alb, FAH, tbx3, TAT and Gck 7 days after differentiation conditions. Note that only the condition EADF showed an expression of all hepatocyte markers tested. HPRT was used as a housekeeping gene to normalize for gene expression.

FIG. 10C—Time course expression analysis after differentiation conditions. At days 2, 5 and 8 days after differentiation, the expression of the hepatocyte markers CYP3A11, Alb, FAH, and the cholangyocyte marker K19, was analysed by RTPCR. Note that the expression of the liver markers CYP3A11 and FAH starts at day 5 and peaks at day 8 after. HPRT was used as a housekeeping gene to normalize for gene expression. A; A8301, D; DAPT, F; FGF10, H; HGF, De; Dexamethasone FIG. 10D—Titration experiment showing the expression of the hepatocyte markers CYP3A11, Alb, FAH, tbx3, TAT, G6P and Gck 7 days after different concentrations of the differentiation compounds A and D. HPRT was used as a housekeeping gene to normalize for gene expression.

FIG. 10E—Immunofluorescent staining for the liver markers K19, Albumin and hepatocyte surface marker. Hoeschst was use to stain nuclei.

FIG. 10F—Xgal staining on Albcreert2LacZ mice liver-derived organoids. Albumin positive cells (arrows) were detected after EADF differentiation in tamoxifen induced Albcreert2LacZ derived cultures.

FIG. 11: Human-derived liver cultures under ERFHNic culture conditions

FIGS. 12A-B: Liver response to Wnt signaling stimulation under physiological conditions or during regeneration after injury FIG. 12A: Injection of Lgr5 ligand R-spondin1 in Axin2 LacZ mice shows that liver cells are responsive to Wnt stimulation (arrows pointing X-gal positive cells). There was no Lgr5 expression so the inventors hypothesise that Lgr4 was used to initiate the response.

FIG. 12B: CCL4 injection in Axin2 LAcZ mice shows that during the regeneration response Wnt signalling is activated

Adult Lgr5-LacZ KI mice were injected with 0.8 ml/kg of the hepatotoxic compound CCL4. The pictures show that in non injected (undamaged) livers the Wnt pathway is active only in cells lining the ducts. After damage by CC14 cells also cells not lining duct have an activated Wnt pathway.

Figure 13A:
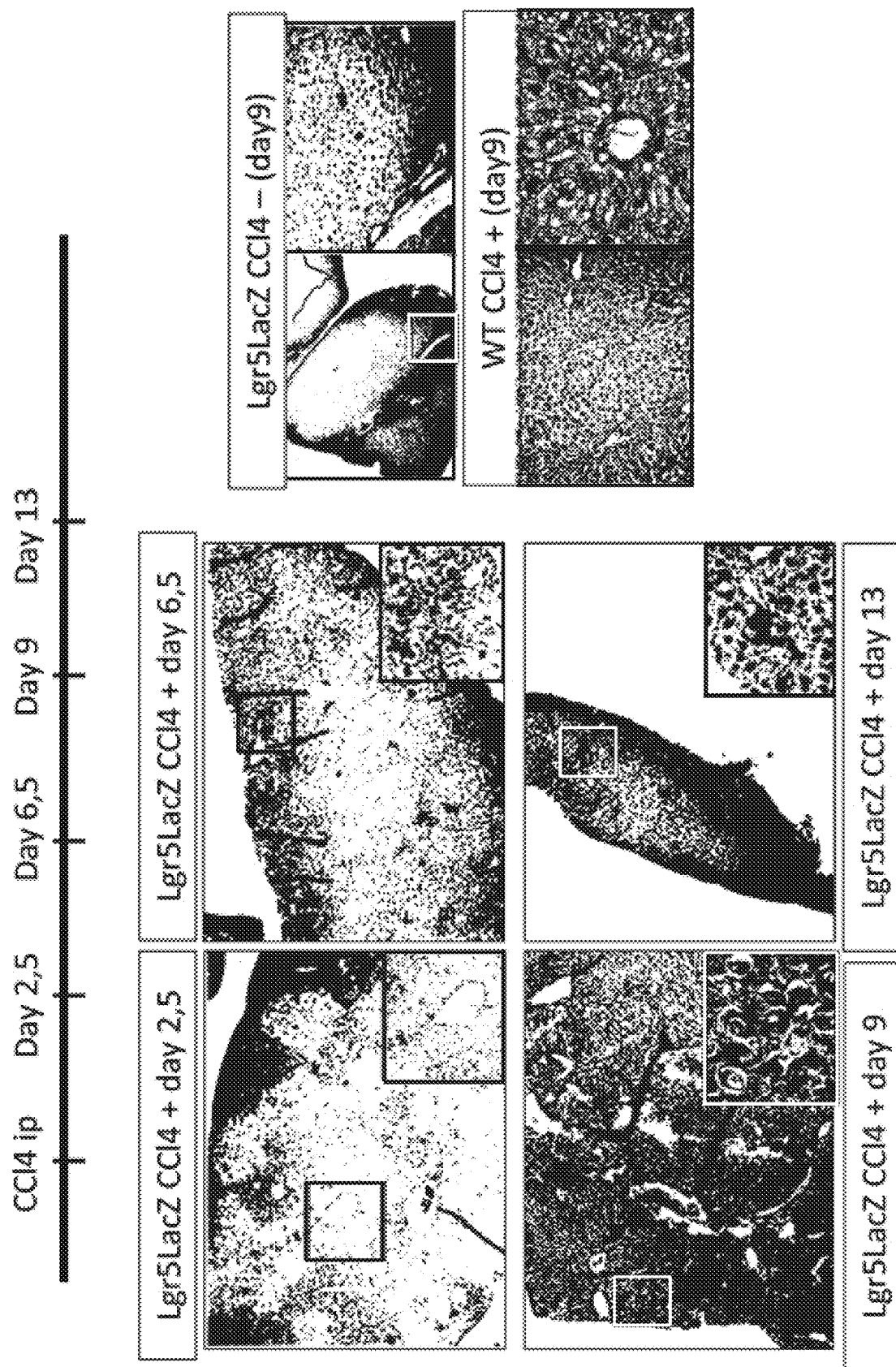
FIGS. 13A-B: Lgr5 upregulation following liver injury-regeneration model.

FIG. 13A—Time course experiment showing upregulation of Lgr5 in CCL4 damaged livers (arrows showing x-gal positive cells). Control CCL4 injected WT mice and placebo-injected Lgr5LacZ Ki mice did not show any staining (right-hand panel).

Figure 13B:
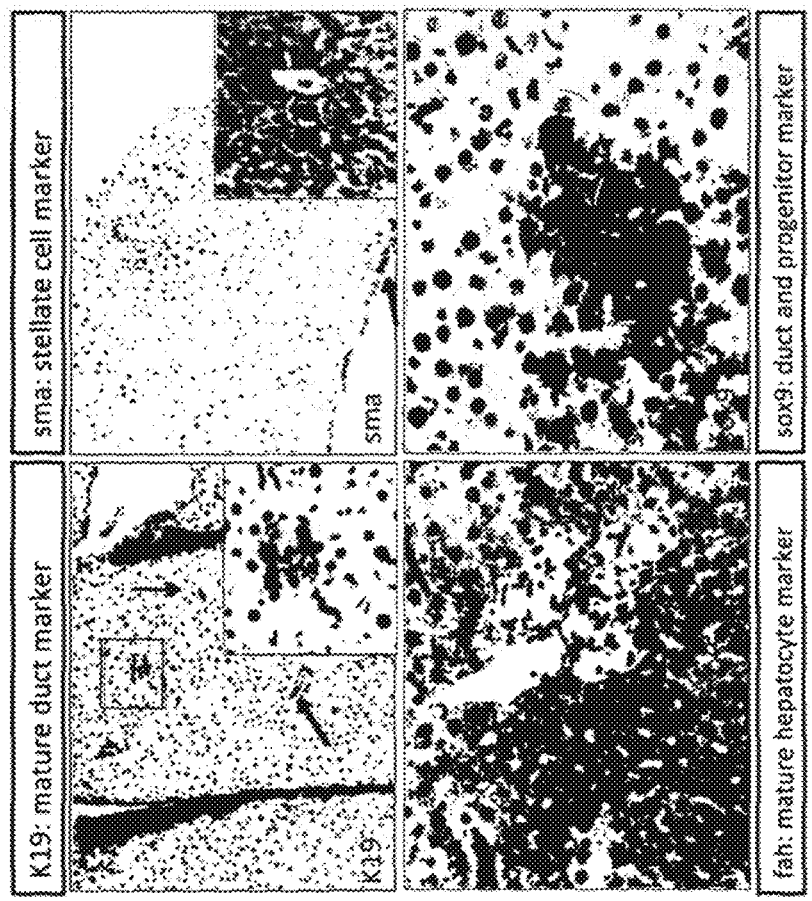

FIG. 13B—Lgr5 co-staining with liver markers.

FIG. 14: Isolated duct staining for K19

Lgr5LacZ duct isolation. K19 staining confirms that the isolated and seeded structures are indeed intrahepatic ducts.

Figure 15A:
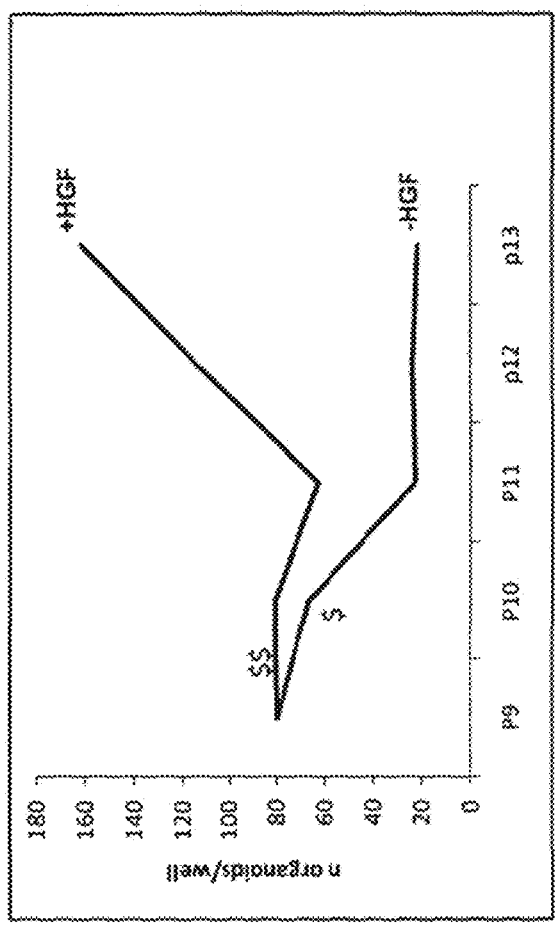
Figure 15B:
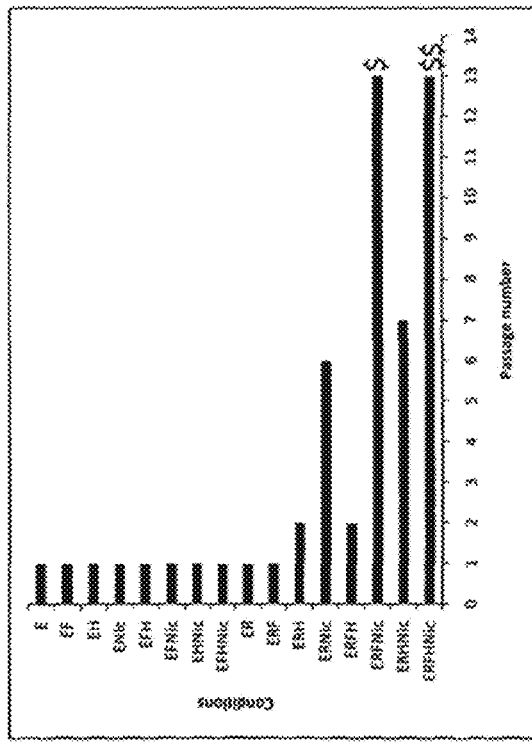

FIGS. 15A-B: Growth factor requirement

The 3 supplemental factors (FGF10, HGF and Nicotinamide) are essential for long term self-maintenance of liver cultures. After long-term culture, the combination of ER including FNic ($) or ERFHNic ($$), both result in high passage numbers. After passage 10, the growth rate is better for the culture condition including the 3 supplemental factors; ERFHNic (see FIG. 16B).

Figure 16A:
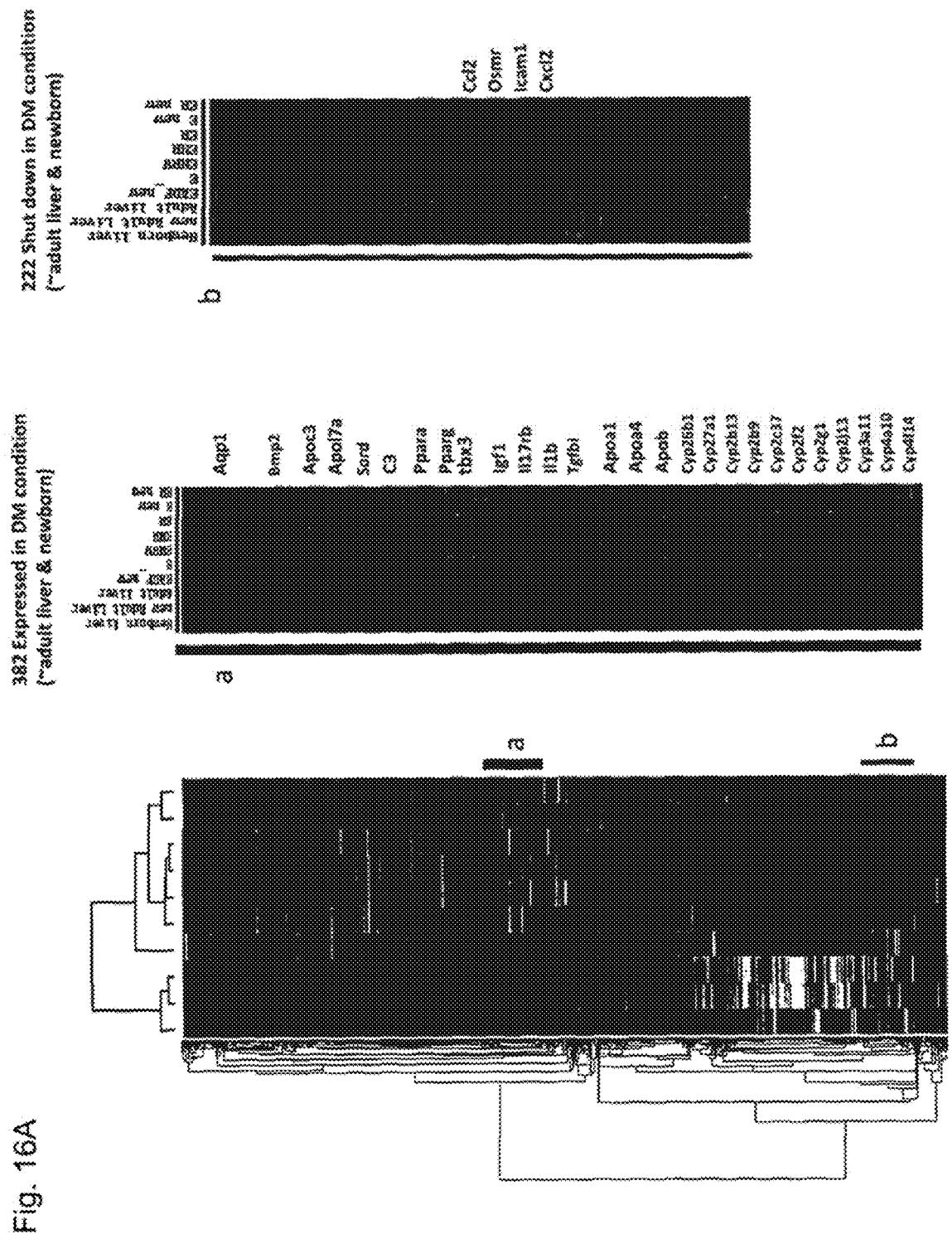
Figure 16B:
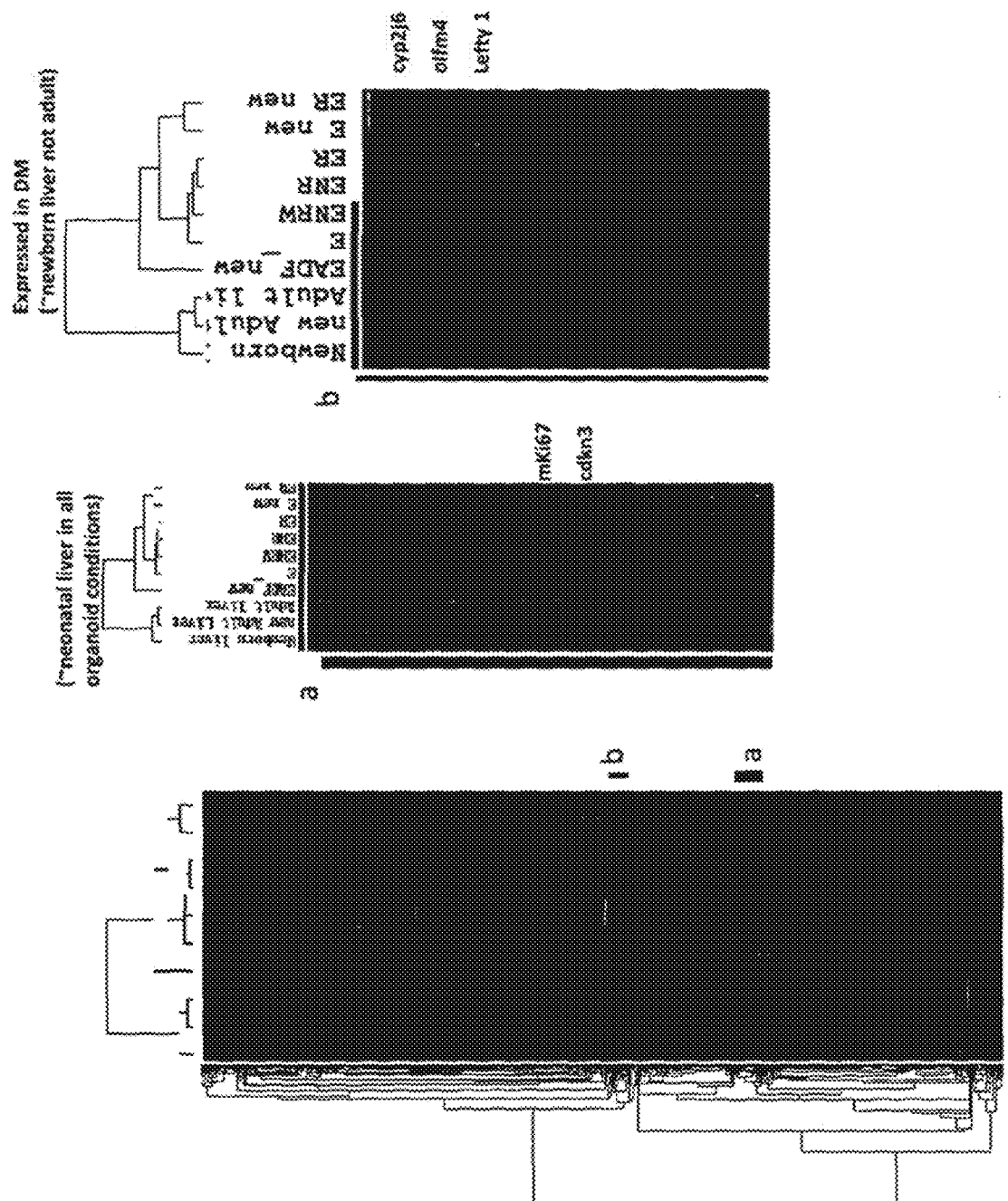

FIGS. 16A-C: Gene expression profile of mouse liver organoids under differentiation conditions resemble the adult and newborn liver profile FIG. 16A—Gene clusters showing the genes similarly expressed (a) or similarly shut down (b) between the differentiation condition EADF and adult or newborn liver.

FIG. 16B—Gene clusters showing the genes differentially expressed between the liver organoids and adult or newborn liver (a) and the genes similarly expressed between EADF and newborn liver (b).

FIG. 16C—Raw signal data from a microarray analysis, comparing the expression levels of selected ductal markers, transcription factors necessary for Ngn3 expression and endocrine markers in adult liver, adult pancreas, pancreas organoids and liver organoids in expansion media.

FIGS. 17A-D: Transplantation of the cells into mouse model of liver disease

Organoids were transplanted into the mouse model: adult FGR mice (FAH−/−RAG−/− IL2R−/−). Hepatocytes were transplanted into the mice as a control.

FIG. 17A—K19 positive cells (left top panel) and Fah positive cells (middle panel) derived from the liver organoids transplanted into FAH knock out mice. Hepatocyte transplanted control (top right panel). Lower flow Cytometry plots show that the % of hepatocyte positive cells was higher in the group that resulted in positive FAH engrafted hepatocytes.

Figure 17B:
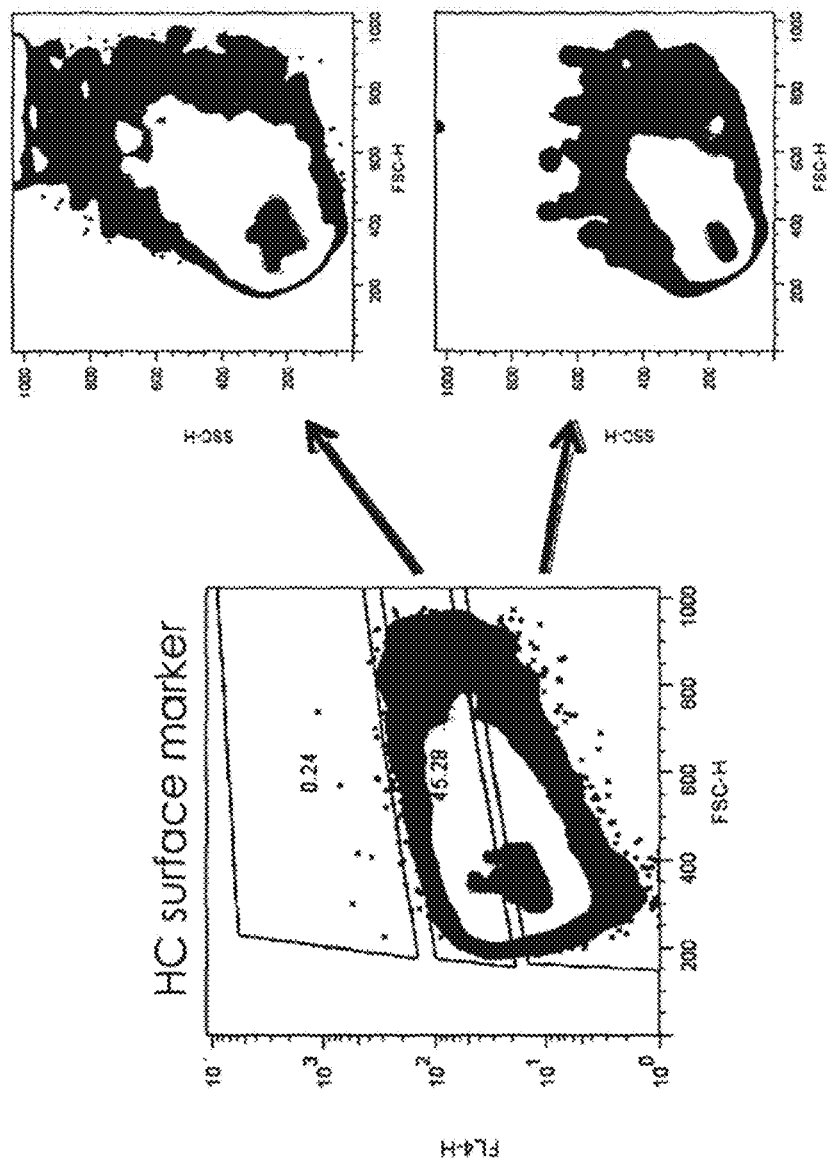

FIGS. 17B-C—Flow Cytometry analyses of cells transplanted. (FIG. 17B) Clone 1, obtained from Lgr5-GFP mouse, and (FIG. 17C) clone 2, obtained from Lgr5-lacZ mouse. The hepatocyte surface marker shows a positive subpopulation that comprises large cells and highly granular cells, i.e. cells that represent the phenotype of mature hepatocytes.

Figure 17D:
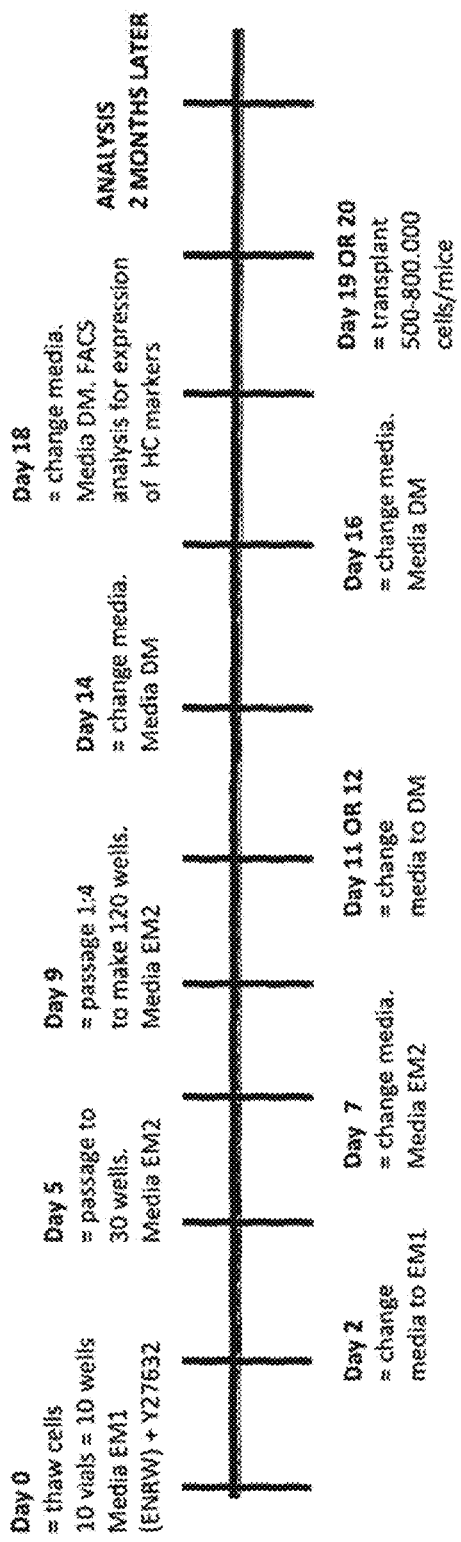

FIG. 17D—Transplantation schedule.

FIG. 18: Mouse liver signature genes

Table showing a) markers expressed in mouse liver stem cells; b) markers not expressed in mouse liver stem cells; c) hepatocyte and cholangiocyte markers expressed in mouse liver stem cell signature for mouse liver organoids in expansion media; d) hepatocyte and cholangiocyte markers not expressed in mouse liver stem cell signature for mouse liver organoids in expansion media; e) reprogramming genes expressed in mouse liver organoids; f) reprogramming genes not expressed in mouse liver organoids. The results were obtained using a liver microarray using the Universal Mouse Reference RNA (Strategene, Catalog #740100) as a reference RNA. If the absolute figures detected were less than 100, the gene was consider as undetected.

FIGS. 19A-E: Human liver signature genes

Table showing results of liver mircroarray of human organoids. From left to right, the results are shown for a) expansion medium EM1, b) expansion medium EM2, c) differentiation medium, d) adult liver.

The numbers (log 2) in the left four columns are the result of a comparison between the sample and a reference (commercial) RNA sample which is used for all arrays. The relative expression of mRNA in each sample compared to the RNA present in the reference sample is shown. The reference RNA used was Universal Human Reference RNA (Stratagene, Catalog #740000). Thus, negative numbers in these columns do not relate to real expression levels it just means there is less of that RNA then in the Reference sample. The 4 columns on the right are absolute figures. If they are below 100, they are considered as undetected.

EXAMPLES

Example 1—an Expansion Medium for Liver Organoid Growth and Expansion

Figure 1A:
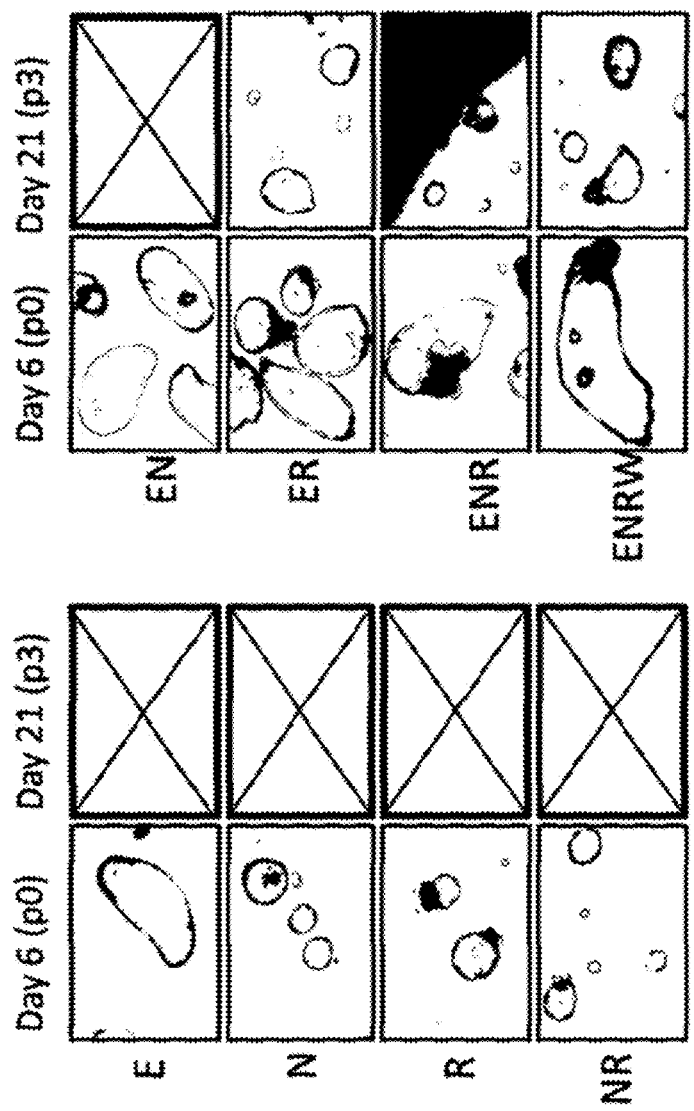
FIGS. 1A-D: Liver organoids growth factor requirement.
Figure 1B:
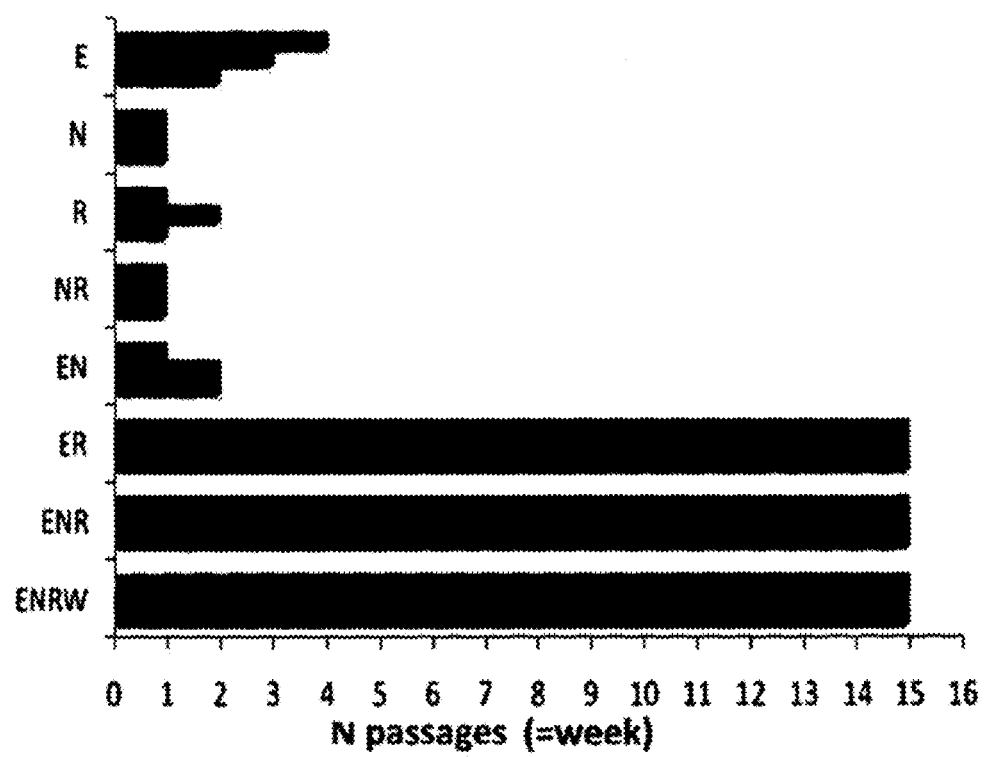
Figure 1C:
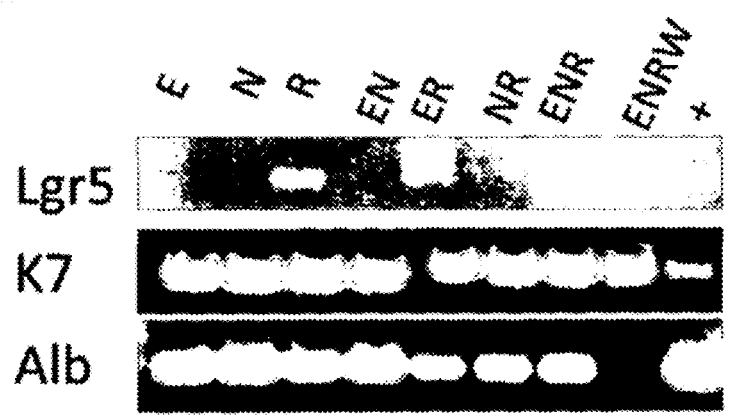
Figure 1D:
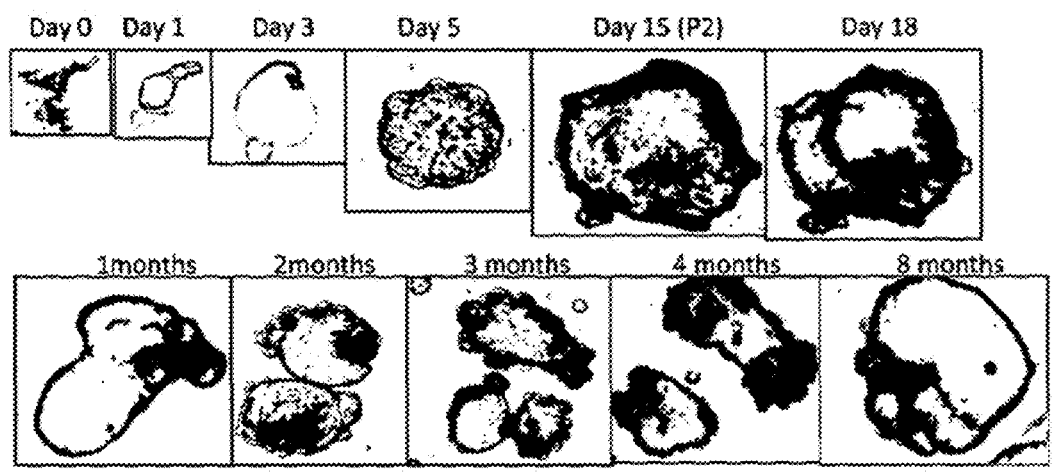
Figure 2A:
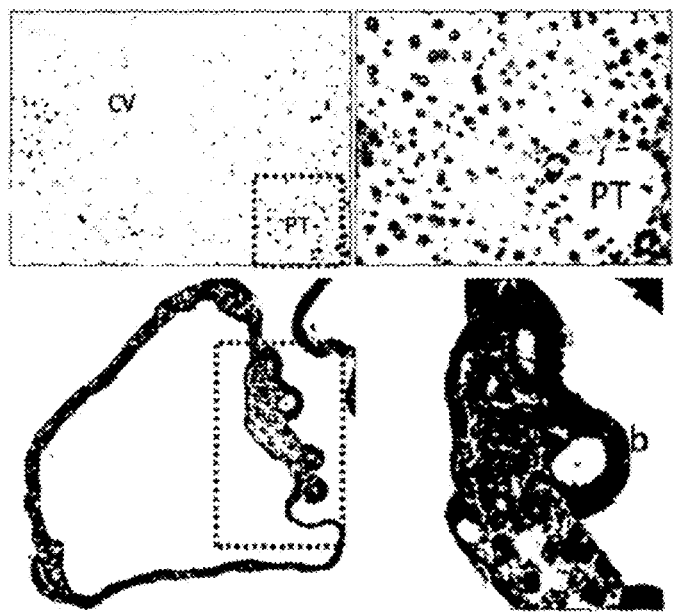
FIGS. 2A-B: Morphology of liver organoids.
Figure 2B:
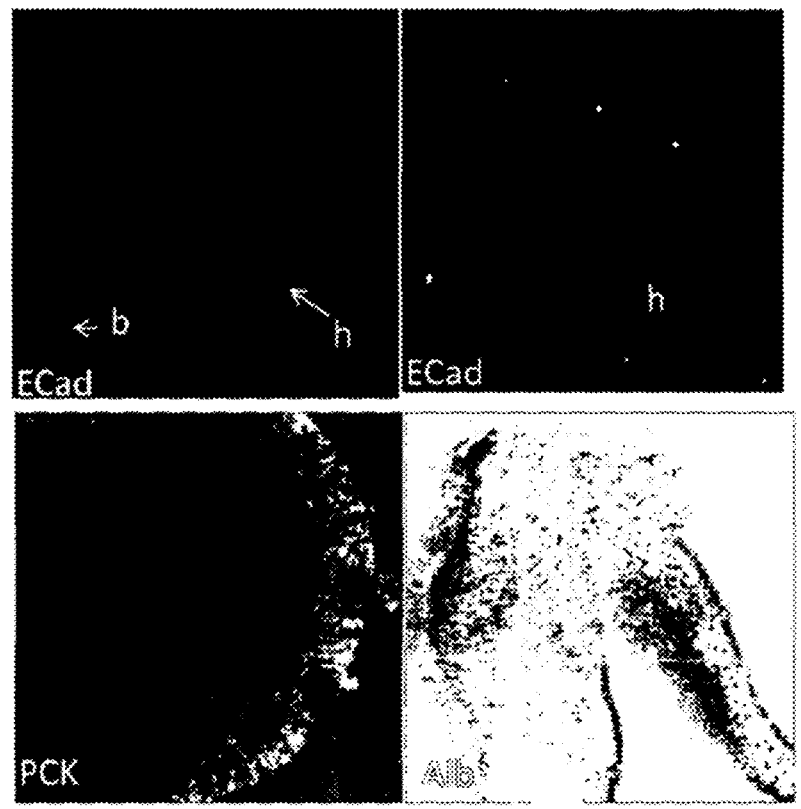

After isolation, biliary ducts (see FIGS. 1A-D) were suspended in MATRIGEL™ and cultured in different growth factor conditions. The combination of EGF (50 ng/ml) and R-spondin 1 (1 ug/ml) supplemented with FGF10 (100 ng/ml), HGF (25-50 ng/ml) and Nicotinamide (1-10 mM), (ERFHNic) were essential for the long term maintenance of the cultures, indicating that Wnt signalling and EGF signalling are strictly required to maintain adult liver progenitor proliferation in vitro. The addition of Noggin (100 ng/ml) and Wnt conditioned media (50%) also showed long term maintenance of the cultures (see FIGS. 1A and 1B). Under these conditions that supported long-term maintenance, Lgr5 expression as well as hepatocyte markers (Albumin) and cholangiocyte markers (K7) were detected by RT-PCR (see FIG. 1C). Under these conditions liver organoids have been weekly passaged by mechanical or enzymatic dissociation, at 1:8 dilution, and have been grown for many months (FIG. 1D).

Figure 3:
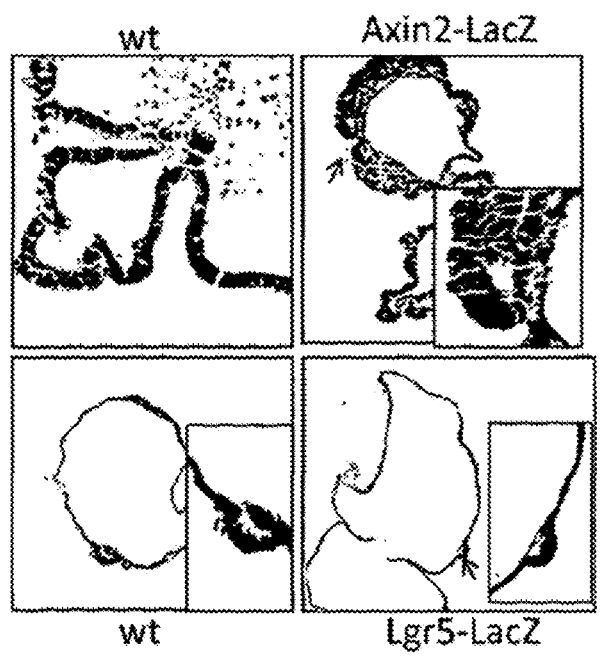
FIG. 3: Wnt signalling in the liver cultures. Lac Z expression was detected in cultures derived from Lgr5-LacZ or Axin2 LacZ mice. No positive staining was detected in liver cultures derived from a B16 mice. Magnification 4×, inset 20×.
Figure 4A:
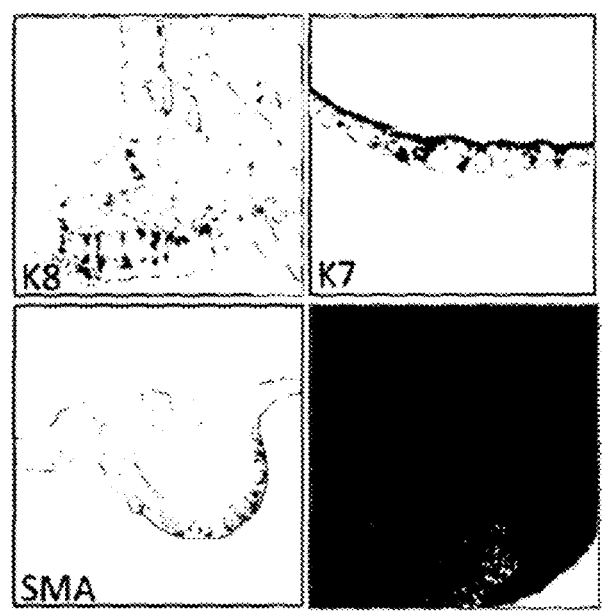
FIGS. 4A-B: Expression of liver differentiating markers.
Figure 4B:
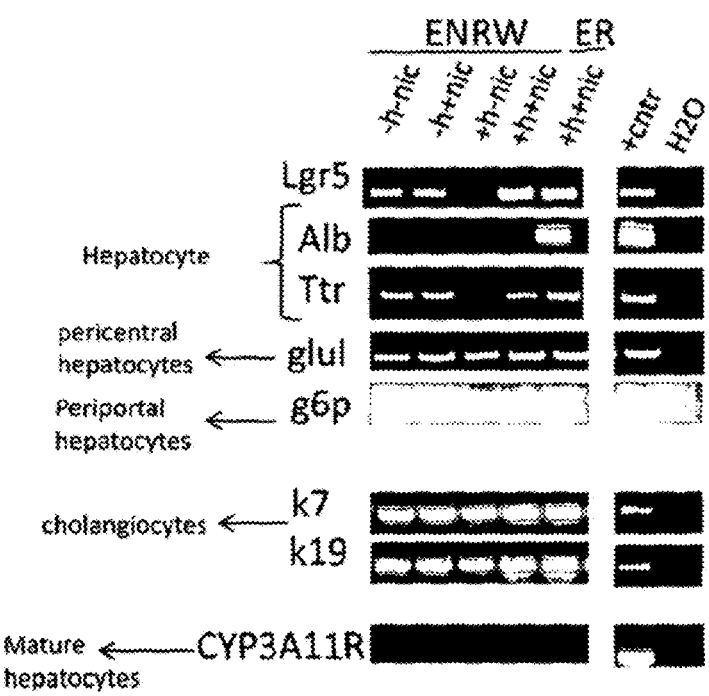

We analysed the expression of the Wnt target genes Axin2 and Lgr5 in the cultures. Cultures of both Axin2LacZ and Lgr5-LacZ livers revealed the presence of Axin2- and Lgr5-positive cells in the liver organoids 1 month after seeding, thus confirming that the Wnt signalling is active and required for culture growth (FIG. 3). The liver cultures also express hepatocyte markers (e.g. albumin, transthyretrin, Glutamine synthetase) and cholangiocyte makers (Keratin 7 and 19) (see FIGS. 4A-B).

Figure 5A:
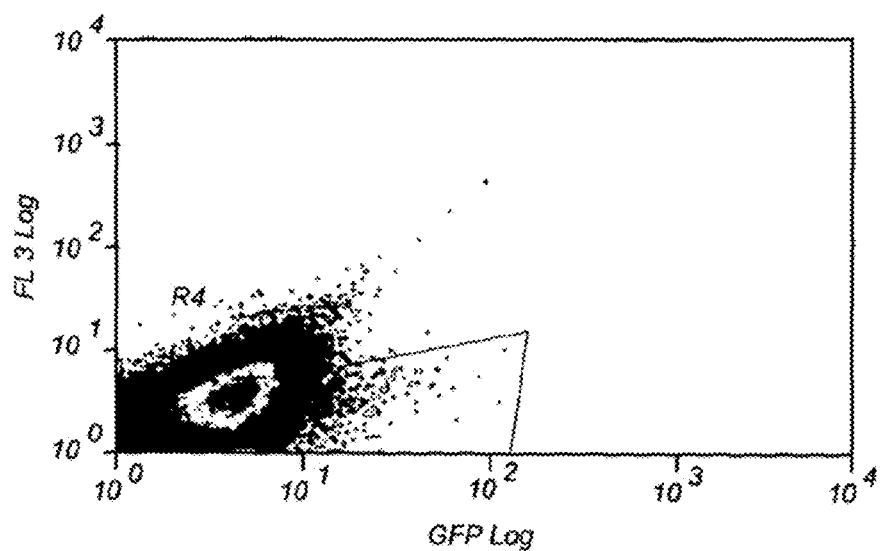
FIGS. 5A-D: Liver single cell cultures.
Figure 5B:
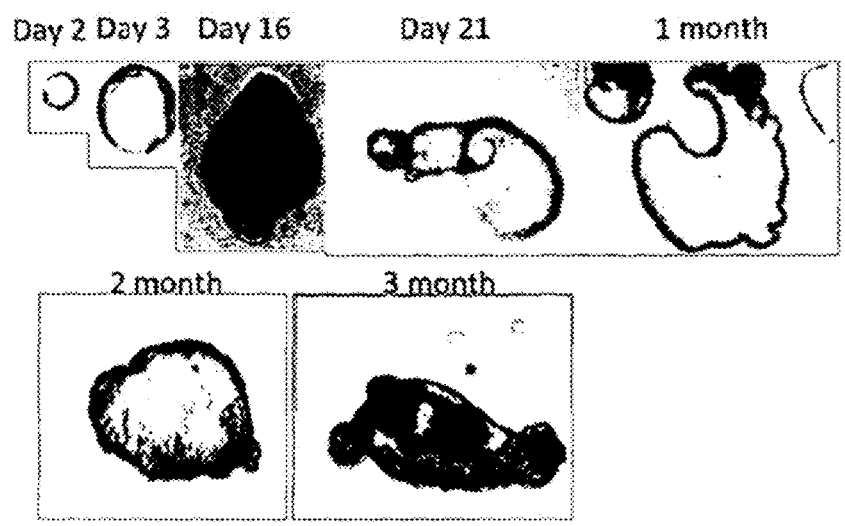
Figure 5C:
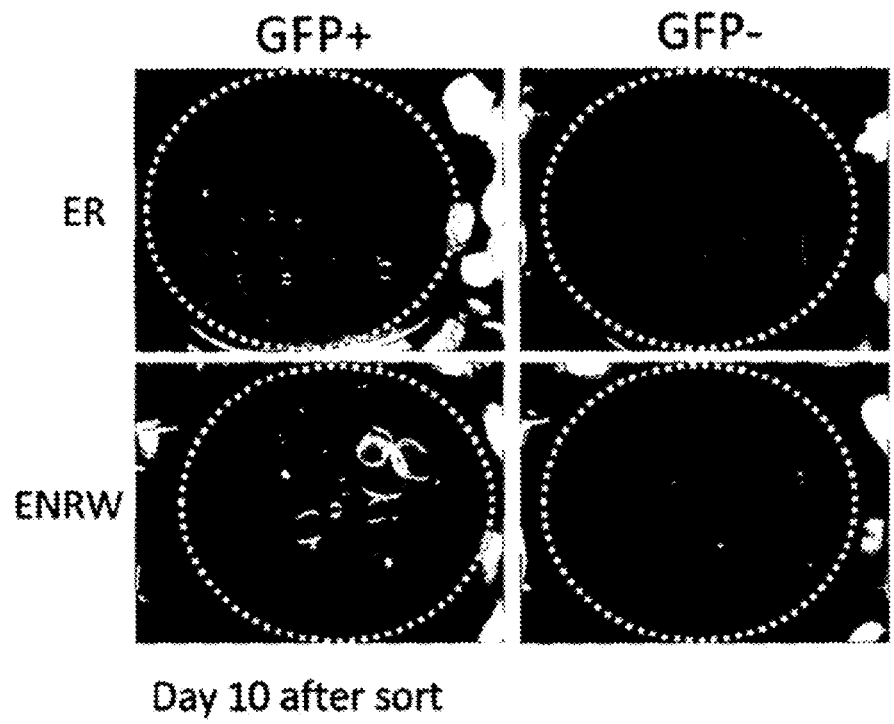
Figure 5D:
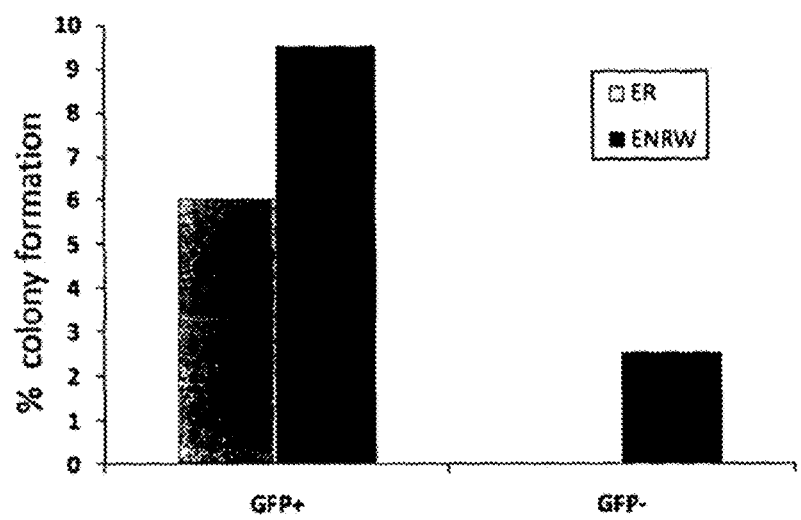

When single Lgr5 cells from a Lgr5LacZ or Lgr5GFP mouse were sorted, single colonies grew into organoids. These cultures also express markers of cholangiocyte and hepatocyte lineages and have been maintained and regularly split into 1:6-1:8 for more than 4 months (see FIGS. 5A-B). Interestingly, only the cultures derived from Lgr5 positive cells grew into organoids (FIGS. 5C-D). These data indicate that Lgr5 cells are progenitor cells of these cultures and able to propagate progeny of the 2 different liver lineages.

Figures 6A, 6B:
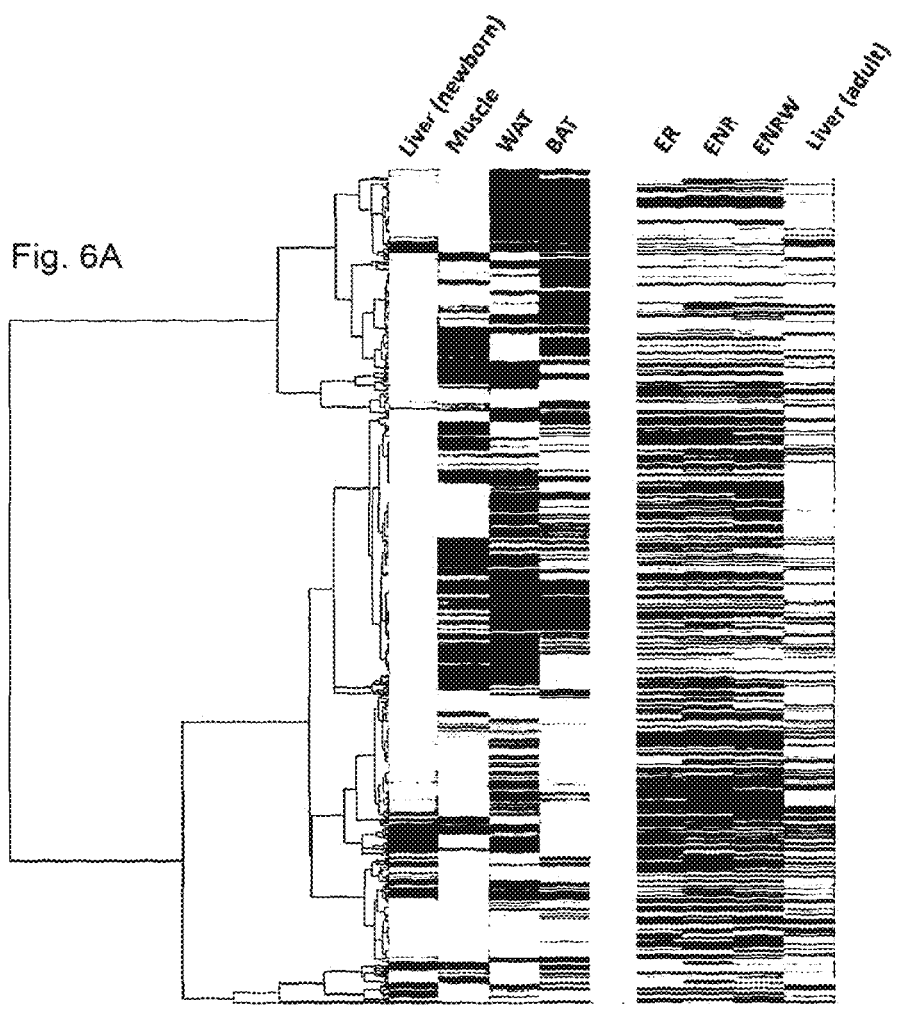
FIGS. 6A-B: Microarray analysis of the liver cultures. Analysis of the gene expression profile of adult liver tissue and liver organoid cultures maintained for 1 month in the ER or ER media supplemented with Noggin (ENR) or with noggin and Wnt (ENRW). The genetic profile was compared between the different samples and the genetic profile of Brow adipose tissue (BAT) white adipose tissue (WAT), muscle and new born liver.

Having established that the liver organoids are derived from Lgr5+ve cells we set out to determine their individual gene signature as compared to the adult liver signature. RNA was isolated from adult liver and from liver organoids grown in ER or ENRW media supplemented with FGF10, Nicotinamide and Hepatocyte Growth Factor. The genetic signature of the adult liver and the 2 liver culture conditions was subsequently derived via comparative gene expression profiling in respect to the expression of a Universal RNA reference. The use of the same reference RNA for the hybridization to all the samples allowed us to compare the 3 independent samples among them (adult liver, ER and ENRW). The heat map analysis revealed that the expression profile of both culture conditions highly resemble the adult liver tissue expression profile, whereas they do not share the same profile when compared to muscle or adipose tissue profile (see FIGS. 6A-B). Among the similar gene expression profile between the adult liver and the liver cultures, liver specific genes as HNF1a, HNF1b, HNF4, Alb, Glu1, Met, G6P, Fand1, Fand2a, CYP4B1, K7 and K19 are detected. The heat map analysis reveals that both culture conditions present similar expression pattern among each other and when compared to the adult liver sample. However, when analyzing the data in detail, we can observe that the condition without Wnt and without noggin shows a more differentiated pattern that the condition including both growth factors. This is in agreement with the data shown in FIG. 1 C where hepatocyte differentiation (by means of albumin expression) is almost absent in the presence of Wnt. This result would indicate that Wnt is favouring the self-renewal of the culture in detriment of the differentiation.

Also, in both culture conditions as well as in the adult liver, non-specific adult liver genes as AFP, and non-liver transcription factors as Pdx1 or NeuroD can be detected.

It is remarkable that, in both culture conditions but not in the adult liver, the stem cell marker Lgr5 was one of the most highly enriched genes in the liver culture signature. Also, cell markers of progenitor populations in small intestine and stomach as Cd44 and Sox9 (Barker & Huch et al Cell stem cell 2010) were highly expressed in both culture conditions but not in adult liver, indicating again the self-renewal capacity of the liver cultures as well as the quiescent status of the normal adult liver.

Additionally, apart from Lgr5, multiple Wnt target genes were also highly upregulated in the liver cultures compared to the adult liver including MMP7, Sp5 and Tnfrs19, among others, providing strong evidence of the requirement of an active and robust canonical Wnt signaling activity to maintain the self renewing capacity of the cultures.

Example 2—an Improved Differentiation Medium

Under ER or ENRW conditions the liver cultures self-renew, and can be maintained and expanded in a weekly basis, for up to 1 year (FIG. 7A). The karyotypic analysis after 1 year shows no evidence of chromosomal aberrations. More than 66% of the cells analysed presented normal chromosomal counts and 13% of them also showed polyploidy, a characteristic trait of hepatocytes (FIG. 7B).

Figure 8A:
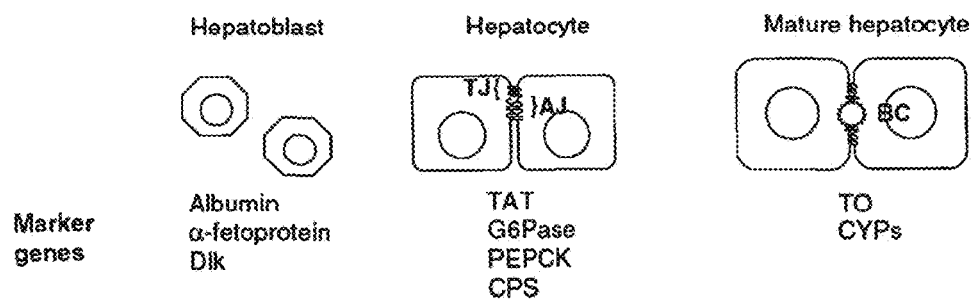
FIGS. 8A-E: Supplemental factors FGF10, HGF and Nicotinamide; effect on growth and differentiation.

The combination of EGF (50 ng/ml) and R-spondin 1 (1 ug/ml) supplemented with FGF10 (100 ng/ml), HGF (25-50 ng/ml) and Nicotinamide (1-10 mM), were preferable for the long term maintenance of the cultures. Under these conditions, we obtained long-lived cell cultures that express biliary duct and some hepatoblast or immature-hepatocyte markers (Glu1, Albumine). However, the number of cells positive for these hepatocyte markers was very low. Under these culture conditions, no mature hepatocyte markers (e.g. p450 Cytochromes) were detected. These results suggest that the culture conditions described here facilitate the expansion of liver progenitors able to generate hepatocyte-like cells, albeit at lower numbers, but not fully mature hepatocytes (FIG. 8A).

Figure 8B:
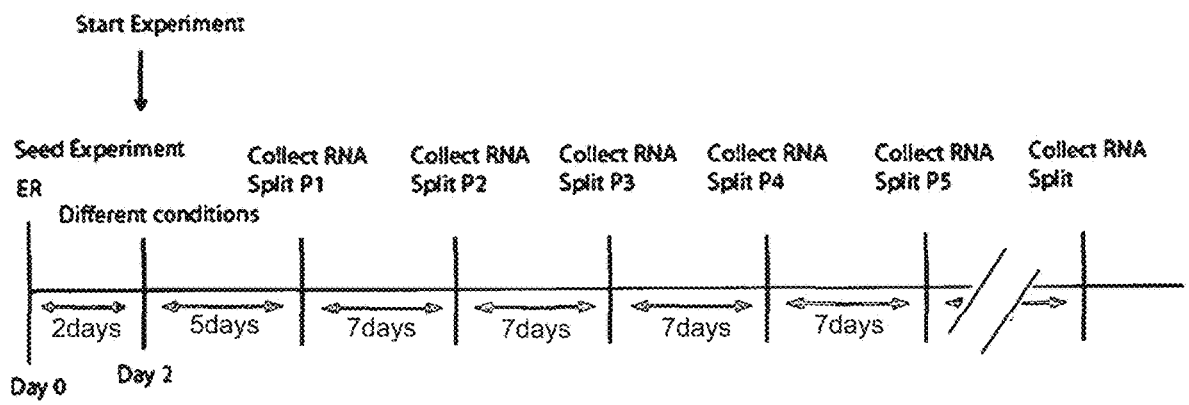

To enhance the hepatocytic nature of the cultures and obtain mature hepatocytes in vitro, we first determined whether the three supplemental factors (FGF10, HGF and Nicotinamide) added to EGF and R-spondin1 were exerting either a positive or negative effect on the hepatocyte expression, as well as on the self-renewal of the culture. We generated liver organoid cultures and cultured them either with EGF or EGF and R-spondin1 plus FGF10 or HGF or Nicotinamide or the combination of these, and we split the cultures once a week for a total period of 10 weeks. At each time-point we also analysed the expression of several mature hepatocyte markers (FAH, CYP3A11) and hepatoblast markers (albumin) (FIG. 8B).

Figure 8C:
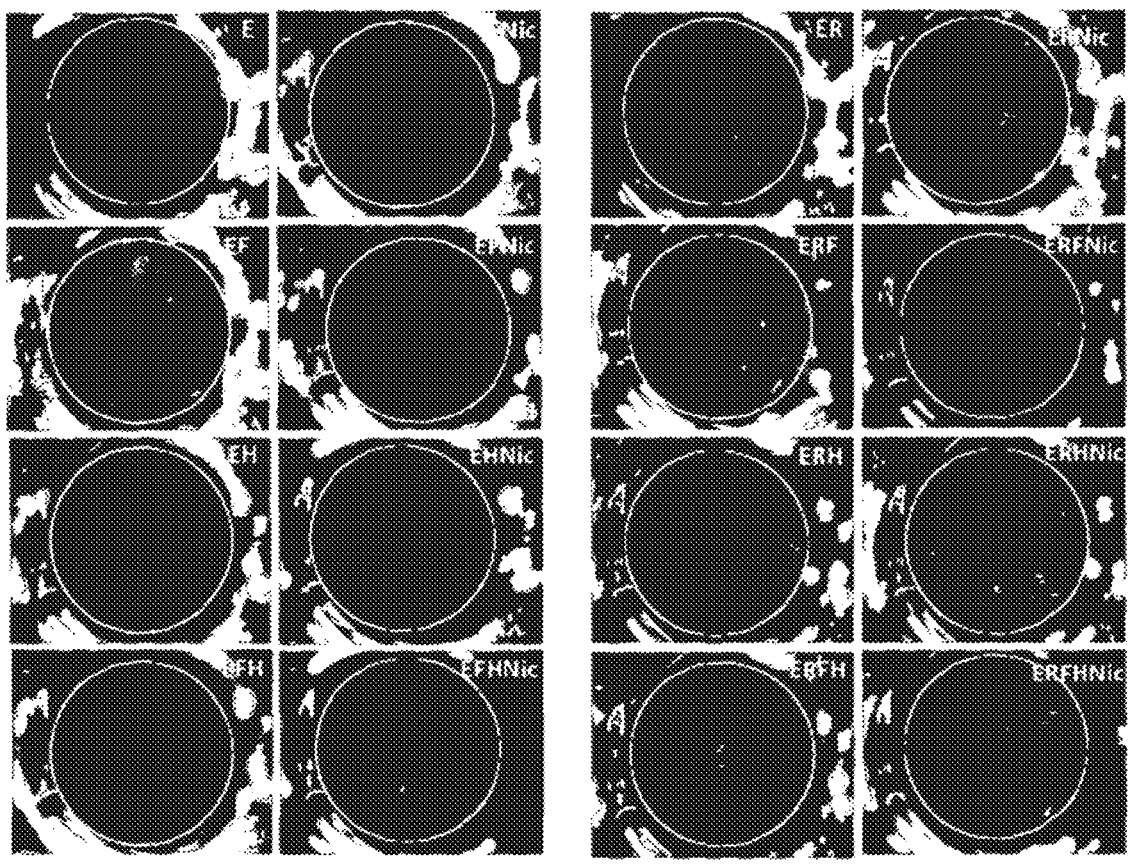
Figure 8D:
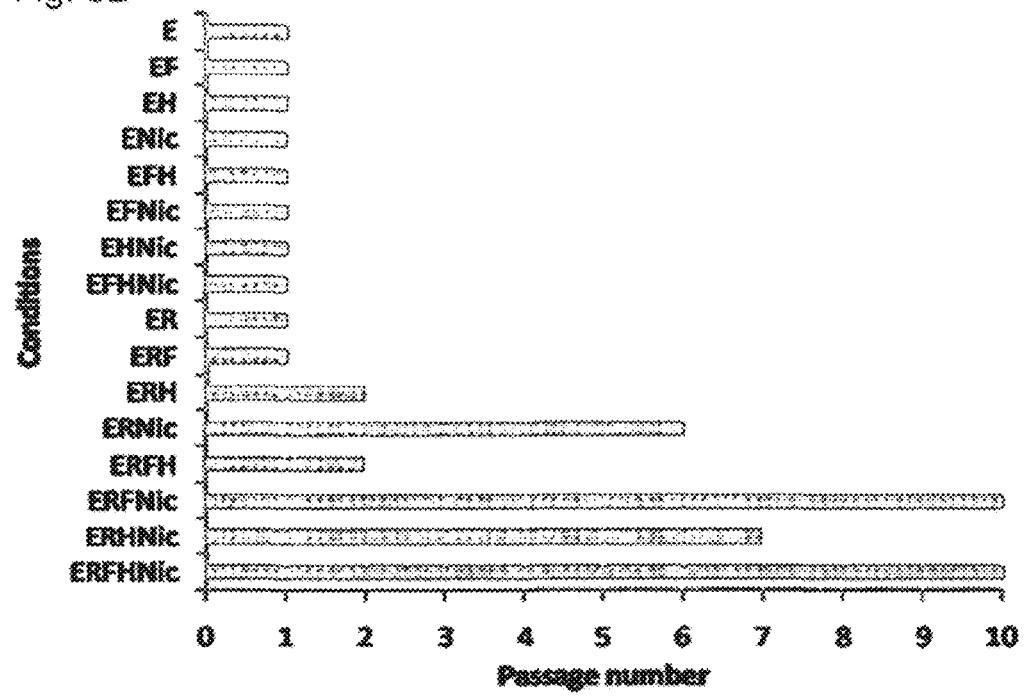
Figure 8E:
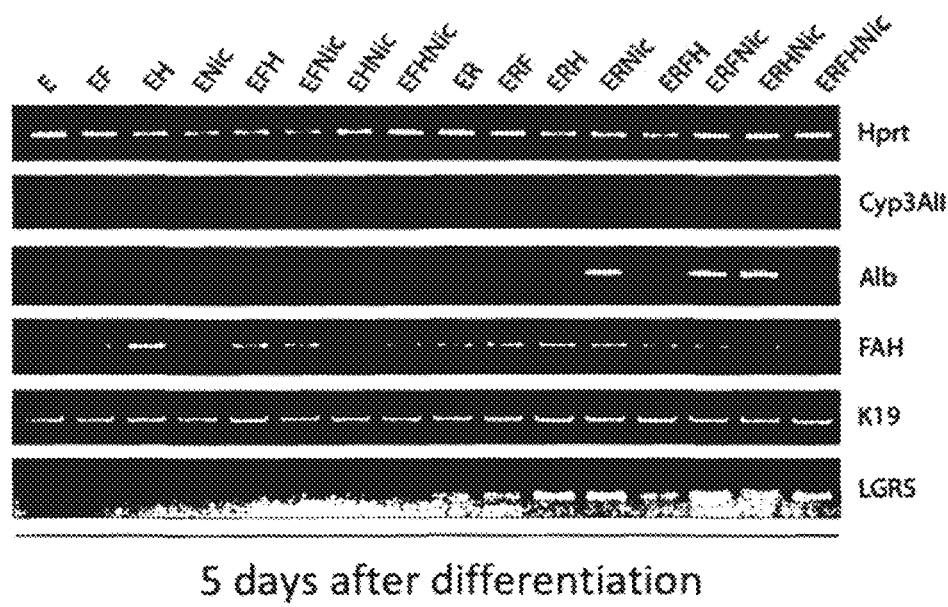

In agreement with the data in FIGS. 1A-D (see example 1), we observed that R-spondin1 and Nicotinamide combined with FGF10 are essential for the growth and self-renewal of the liver cultures (FIGS. 8C-D). R-spondin1 and Nicotinamide both inhibit the expression of the mature marker CYP3A11 and yet promote the expression of the hepatoblast marker albumin. The addition of either FGF10 or HGF to media containing only EGF (without R-spondin1 and without nicotinamide), facilitated the expression of the mature marker CYP3A11, albeit at very low levels (FIG. 8E). To identify additional compounds that might facilitate hepatocyte differentiation, we used two different approaches, both based upon base conditions of: EGF+HGF and/or FGF10.

The first approach involved testing a series of compounds in addition to the EGF+FGF10 or HGF condition. A complete list of the compounds analysed is shown in table 2.

TABLE 2

| Compounds | Signal | | Concentration | Result | |
|---|---|---|---|---|---|
| | | | | Alb | CYP3AII |
| Exendin4 | Glucagon like peptide 2 analog | Sigma E7144 | 0.1-1 uM | | |
| Retinoic Acid | RAR-RXR receptor ligand | Sigma | 25 nM | | |
| Retinoic Acid + Exendin 4 | | | | | |
| Sonic Hedgehog | | Invitrogen C25II | 500-100 ng/ml | | |
| BMP4 | BMP signaling | Peprotech 120-05 | 20 ng/ml | | |
| DAPT | Gamma-secretase inhibitor | Sigma D5942 | 10 nM | | |
| A8301 | Alk5/4/7 inhibitor | Tocris Bioscience 2939 | 50 nM | | |
| DAPT + A8301 | | | | +++ | +++ |
| FGF4 | FGFR1,2 ligand | Peprotech | 50 ng/ml | | |
| FGF1 | FGFR1,2,3,4 ligand | Peprotech 450-33A | 100 ng/ml | | |
| Dexamethasone | | Sigma D4902 25MG | 10 μM-1 mM | | |
| Oncostatin M (OSM) | | R&D systems 495-MO-025 | 10-1000 ng/ml | | |
| FGF4 + OSM + Dexa | | peprotech | 100 ng/ml | | |
| IGF | | | | | |
| Valproic acid | histone deacetylase inhibitor and regulator of ERK, PKC Wnt/β-catenin pathways | Stemgent 04-0007 | 250 μM | | |
| Sodium Butyrate | histone deacetylase inhibitor | Stemgent 04-0005 | 250 μM | | |
| BIX01294 | G9a HMTase inhibitor | Stemgent 04-0002 | 1 μM | | |
| RG 108 | DNA methyltransferase inhibitor | Stemgent 04-0001 | 1 μM | | |
| TSA | | | 100 nM | + | − |
| Hydrocortisone | glucocorticoid | Sigma H6909 | 5 nM | | |
| Oncostatin M (OSM) | | R&D systems 495-MO-025 | 10-1000 ng/ml | | |
| ARA | | Sigma A 0937 | 500 nM | | |
| R 59022 | Diacylglycerol kinase inhibitor | Sigma D 5919 | 500 nM-50 nM | + | + |
| Arterenol bitrartre: — | andrenoreceptor agonist | sigma A 0937 | 500 nM-50 nM-5 nM | | |
| LIF | | | $10^3$ | | |

TABLE 2-continued

| Compounds | Signal | Concentration | | Result | |
| --- | --- | --- | --- | --- | --- |
| | | | | Alb | CYP3AII |
| PD 035901 | MEK1 inhibitor | Axon Medchem cat n 1386 | 500 nM | | |
| CHIR99021 | GSK3 inhibitor | Axon Medchem cat n 1408 | 3 uM | | |
| DMSO | | | 1% | | |
| L-Ascobic acid | | Sigma 077K13021 | 1 mM | | |
| VEGF | | Peprotech | | | |
| MATRIGEL ™ 50% | | | | | |
| MATRIGEL ™ 20% | | | | | |
| VEGF + DEXA | | | | | |

The second approach took into account knowledge from published developmental studies regarding the expression of the transcription factors essential to achieve biliary and hepatocyte differentiation in vivo. A comparative analysis of the expression of transcription factors in the organoids under E or ER or ENRW conditions supplemented with FGF10, HGF and Nicotinamide is shown in FIGS. 8A-E. All the transcription factors required for Hepatocyte specification were present, besides tbx3 and prox1. However, we also noticed that the expression of specific biliary transcription factors was highly upregulated in the cultures containing R-spondin1 (R), indicating that the culture gene expression was unbalanced towards a more biliary cell fate.

Figure 10A:
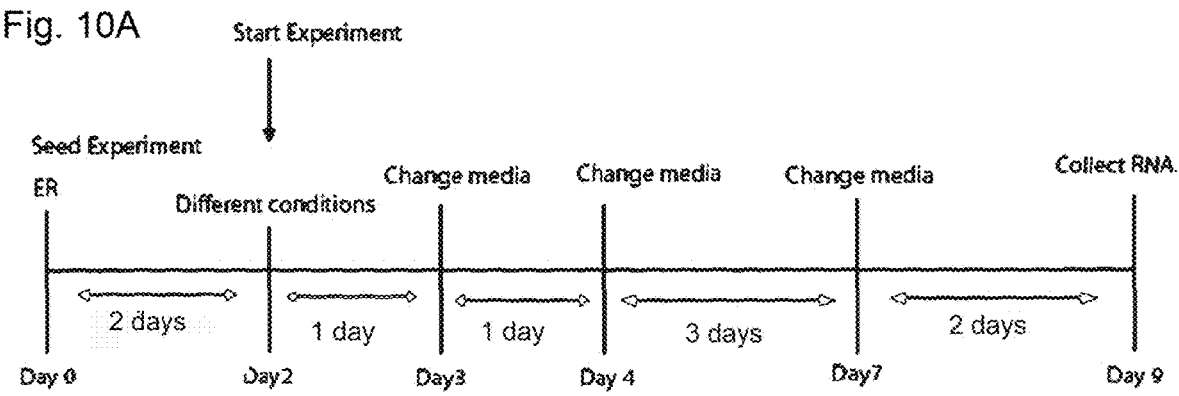

Notch and TGF-beta signaling pathways have been implicated in biliary cell fate in vivo. In fact, deletion of Rbpj (essential to achieve active Notch signalling) results in abnormal tubulogenesis (Zong Y. Development 2009) and the addition of TGF-beta to liver explants facilitates the biliary differentiation in vitro (Clotman F. Genes and Development 2005). Since both Notch and TGF-beta signalling pathways were highly upregulated in the liver cultures (FIG. 9) we reasoned that inhibition of biliary duct cell-fate might trigger the differentiation of the cells towards a more hepatocytic phenotype. A8301 was selected as an inhibitor of TGF-beta receptor ALK5, 4, and 7 and DAPT as inhibitor of the gamma-secretase, the active protease essential to activate the Notch pathway. We first cultured the cells for 2 days in the expansion conditions (ER media) and at day 2 (FIG. 10A) we started the differentiation conditions by adding the combination of the different compounds. Media was changed every other day, and the expression of differentiated markers was analysed 8-9 days later. The ER and ENRW conditions were used as negative control.

Figure 10B:
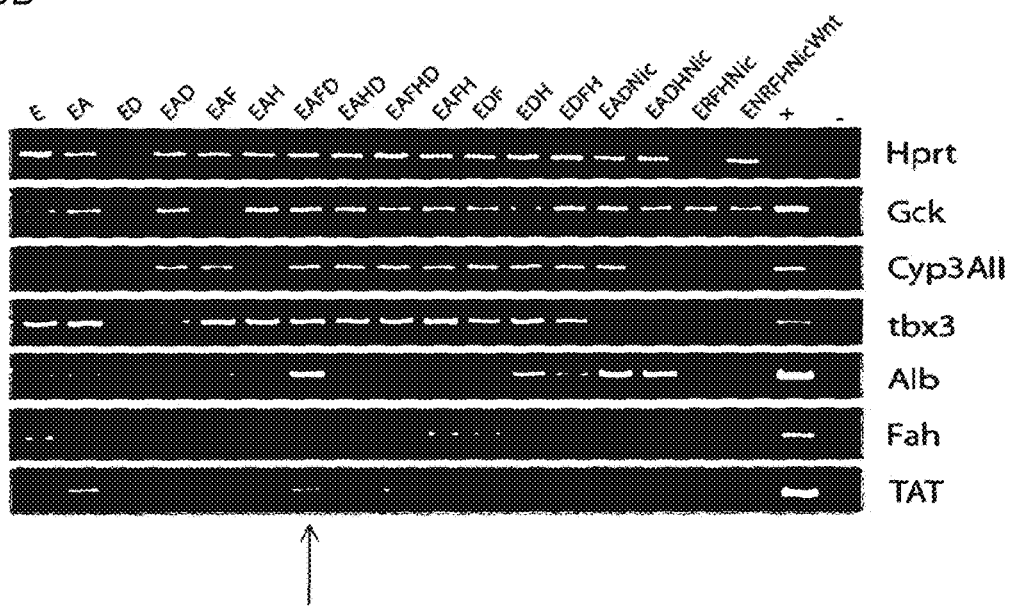
Figure 10C:
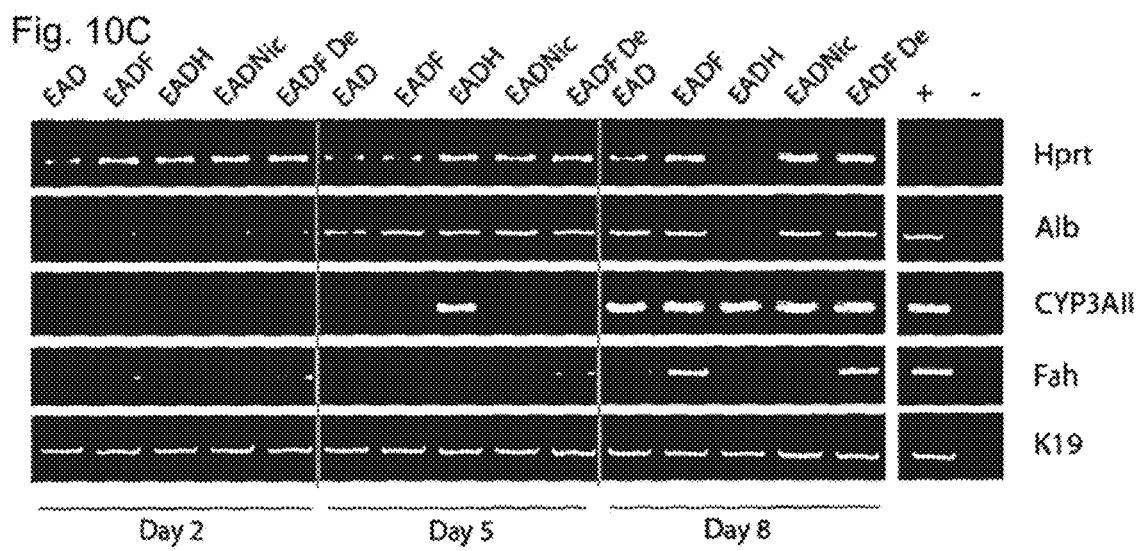
Figure 10D:
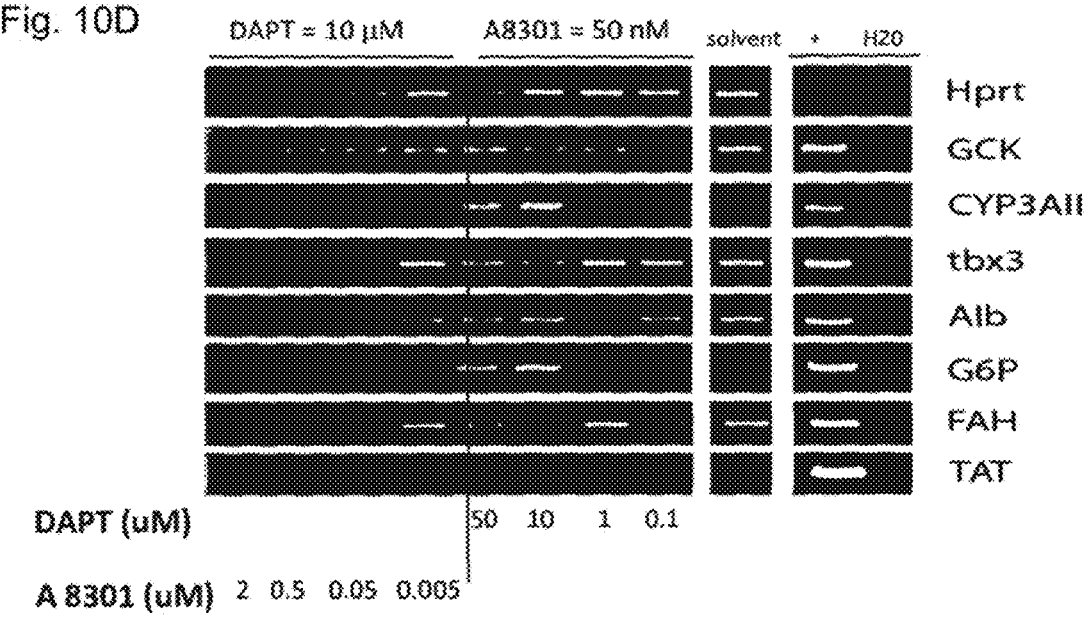

The combination of EGF+FGF10 with DAPT and A8301 resulted in surprisingly large enhancement of expression of the hepatocyte markers analysed (CYP3A11, TAT, Albumin) (FIG. 10B). The effect was already detectable by day 5 and peaked at days 8-9 (FIG. 10C). The maximal concentration efficiency was achieved at 10 uM (DAPT) and 50 nM (A8301) (FIG. 10D) respectively. The addition of dexamethasone (a known hepatocyte differentiation molecule) did not result in any improvement in gene expression. The combination of EGF, FGF10, A8301 and DAPT not only enhances the expression but also increases the number of hepatocyte-like cells, as assessed by immunofluorescent against the hepatocyte markers albumin and 2F8, and Xgal staining on AlbCreLacZ derived organoids (FIGS. 10E-F). Therefore, we can conclude that the aforementioned differentiation protocol facilitates the generation of hepatocyte-like cells in vitro from liver stem cell cultures.

Example 3—Human Liver Organoids

Using these expansion conditions (ERFHNic and ENRWFHNic) we have also been able to expand human biliary-derived cultures (FIG. 11) with the addition of 500 uM TGF beta inhibitor (A83-01) to the expansion medium.

Material and Methods (for Examples 1-3)

Liver Culture-Biliary Duct Isolation

Isolated adult liver tissue was washed in cold Advanced-DMEM/F12 (Invitrogen) and then, the tissue was chopped into pieces of around 5 mm animals and further washed with cold dissociation buffer (collagenase, dispase, FBS in DMEM media). The tissue fragments were incubated with the dissociation buffer for 2 h at 37° C. Then, the tissue fragments were vigorously suspended in 10 ml of cold isolation buffer with a 10 ml pipette. The first supernatant containing death cells was discarded and the sediment was suspended with 10-15 ml of dissociation buffer. After further vigorous suspension of the tissue fragments the supernatant is enriched in biliary ducts. This procedure is repeated until enough biliary ducts are obtained.

Isolated biliary ducts are pelleted and mixed with 50 µl of MATRIGEL™ (BD Bioscience), seeded on 24-well tissue culture plates and incubated for 5-10 min at 37° C. until complete polymerization of the MATRIGEL™. After polymerization, 500 µl of tissue culture media are overloaded.

Media composition: Advanced-DMEM/F12 supplemented with B27, N2, 200 ng/ml N-Acetylcysteine, 50 ng/ml EGF, 1 µg/ml R-spondin1, gastrin: 10 nM, FGF10 100 ng/ml, Nicotinamide 10 mM and HGF: 50 ng/ml and 50% Wnt conditioned media.

The entire medium was changed every 2 days. After 1 week, Wnt conditioned media is withdrawal and the formed organoids removed from the MATRIGEL™ using a 1000 µl pipette and were dissociated mechanically into small fragments and transferred to fresh MATRIGEL™. Passage was performed in 1:4 split ratio once or twice per week. Under these conditions cultures have been maintained for at least 6 month.

Reagents

Human Hepatocyte Growth Factor (HGF) was purchased from Peprotech, EGF invitrogen, R-Spondin Nuvelo, Noggin peprotech, FGF10 Peprotech, gastrin Sigma Aldrich, nicotinamide Sigma.

Microarray

For the expression analysis of Lgr5-derived liver cultures, RNA was isolated using a Qiagen RNAase kit, from adult liver or from liver cultures cultured in media without Wntcm and Noggin (ER) or with Wntcm and Noggin (ENRW). 150 ng of total RNA was labelled with low RNA Input Linear Amp kit (Agilent Technologies, Palo Alto, Calif.). Universal mouse Reference RNA (Agilent) was differentially labelled and hybridized to either adult liver tissue or ER or ENRW treated cultures. A 4X44K Agilent Whole Mouse Genome dual colour Microarrays (G4122F) was used. Labelling, hybridization, and washing were performed according to Agilent guidelines.

Example 4—Lgr5 Expression is Upregulated Following Liver Injury

In the liver, Wnt signalling is active in central vein areas. We have recently observed that Wnt signaling plays a key role in liver metabolism (Boj et al. personal communication). In the liver duct cells, Wnt signalling is activated following liver injury (Hu et al 2007, Gastroenterology, 133(5): 1579-91). Similarly, using the Axin2-LacZ allele, which represents a faithful, general reporter for Wnt signalling, we also have observed upregulation of Wnt signaling in the whole liver parenquima after injection of the Wnt agonist Rspo1 (see FIG. 12A) or following liver injury by the hepatotoxic compound carbon tetrachloride (CC14) (see FIG. 12B).

The Wnt target gene Lgr5 marks stem cells in several actively self-renewing tissues, but has not previously been reported to be expressed upon injury. Our previously described Lgr5-LacZ knockin mice (Barker et al, 2007, Nature 449 (7165): 1003-7) show that Lgr5 is essentially undetectable in healthy liver although a residual mRNA expression is detected by qPCR. Following injection of CC14 on Lgr5-LacZ knockin mice (see Barker et al, 2007, supra for LacZ mice and Furuyama K et al., Nat Genetics, 43, 34-41, 2001 for description of CC14 method), we observed a clear expression of the reporter in newly formed bud structures in the liver (see FIG. 13A), peaking at day 6.5 after injury and being maintained up to day 9 to show a clear decay once the liver is completely regenerated at day 13 after injury (see FIG. 13A, top right panel). No expression of the reporter was detected in wild-type littermates undergoing similar injury protocol (see FIG. 13A, bottom right panel).

The appearance of Lgr5 expression at sites of active regeneration, suggested that Lgr5 might herald de novo activation by Wnt of regenerative stem cells/progenitors upon injury. Indeed, we found that the novo appearing Lgr5 cells do not express markers of mature liver cells (K19 or FAH) or stellate cells (SMA) but instead, they are positive for the recently described liver progenitor marker Sox9 (FIG. 13B). This means that Lgr5+ cells, which are the starting point for obtaining in vitro organoids, can be obtained from liver fragments by inducing liver injury or by stimulating Wnt signalling with R-spondin. The induction of Lgr5 expression in liver cells by injury or by R-spondin may be carried out in vivo before the cells are obtained, ex vivo in an isolated liver, or in vitro in a liver fragment or population of liver cells.

Example 5—Long-Term Expansion of Liver Organoid Cultures

In example 1, it was found that the combination of EGF (50 ng/ml) and R-spondin 1 (1 ug/ml) supplemented with FGF10 (100 ng/ml), HGF (25-50 ng/ml) and Nicotinamide (1-10 mM), were preferable for the long term maintenance of the cultures. We now also have evidence that the three supplemental factors (FGF10, HGF and Nicotinamide) added to EGF and R-spondin1 are all necessary for the expansion of the cultures for longer than 3 months. To assess that, we isolated biliary ducts from the liver parenquima, as shown in FIG. 14 (K19 staining was used to confirm the identity of the isolated structures), and generated liver organoid cultures by culturing them with: i) EGF; or ii) EGF and R-spondin1 plus FGF10 or HGF or Nicotinamide; or iii) EGF and R-spondin1 plus FGF10 and HGF and Nicotinamide (ERFHNic). We have split the cultures once a week for a total period of 14 weeks. Results confirmed, as reported in examples 1 and 2, that EGF, R-spondin1 and Nicotinamide combined with FGF10 are essential for the growth and self-renewal of the liver cultures. After 10 passages, the cultures lacking HGF showed a growth disadvantage compared to the cultures supplemented with HGF. Although still viable, the proliferation ratio decreased to 1:2-1:4 compared to the 1:6-1:8 of the cultures supplemented with the complete combination (FGF10, HGF, and Nicotinamide). After 15 passages, the cultures with ERFNic not supplemented with HGF were no longer viable. Therefore, these results suggest that HGF is essential for maintaining a good proliferating rate after long-term maintenance (FIGS. 15A-B).

Example 6—Markers Expressed in Liver Organoids Under Differentiation Conditions Using the differentiation protocol described in example 2, we were able to detect a hepatoblast marker (albumin) and a hepatocyte surface marker in the liver organoids. To quantify the number of these hepatocyte-like cells, we performed flow cytometry analysis of the cultures using a hepatocyte surface marker. We observed that, whereas in the expansion culture condition almost no hepatocyte surface marker-positive cells were detected, after differentiation, up to 35% of the cells were positive for this hepatocyte surface marker (see FIGS. 17B-C).

We then analysed the gene expression profile of the mouse liver organoids under these differentiation conditions (FIGS. 16A-C and FIGS. 1A-D, we see strong upregulation of eg Alb, FAH, and TAT and the Cyp3 genes). We found that the gene expression of the mouse liver organoids after differentiation resemble that of mature mouse hepatocytes and/or mouse liver.

Example 7—Transplantation of Liver Organoids into Mice

Cells were taken from the organoids that had been grown using ERFHNic expansion conditions and EAFD differentiation conditions and were transplanted into immunodeficient strain of mice deficient in the tyrosine catabolic enzyme fumarylacetoacetate hydrolase (FAH), a mouse model for Tyrosinemia type I human disease (Azuma et al. 2007, Nature Biotech, 25(8), 903-910). The transplantation schedule is shown in FIG. 17D. Preliminary results show that scattered FAH positive cells can be found in the liver parenquima of the FAH deficient mice, indicating that liver cells derived from the organoid cultures have engrafted into the recipient livers (see FIG. 17A, right-hand side). Furthermore, significantly increased numbers of K19 positive cells were also detected in the livers of the recipient mice. This suggests that the organoid-derived transplanted cells are able to generate both lineages in vivo: hepatocytes (as demonstrated by the FAH marker) and cholangyocytes (as demonstrated by the K19 marker) (see FIG. 17A, left top panel). This was further supported by flow cytometry analysis of transplanted cells that had come from two separate clones from two separate cultures (FIGS. 17B and 17C respectively). The Lgr5+ cells were transduced with a virus containing GFP and flow cytometry analysis was carried out after differentiation. Cells that were positive for the hepatocyte surface marker show a larger scatter indicating larger cells, which represent granularity and maturity i.e. mature hepatocyte cells. The cells that were negative for the hepatocyte surface marker resulted in less scattering indicating smaller cells i.e. less mature progenitors. Therefore, all cell types are present (mature and immature cells) in a differentiating culture. The rest of the differentiated cells, so the cells not used for FACS analysis were used for the transplantation experiments.

Example 8

Organoids from mouse liver cultured in accordance with a method of the invention were analysed using microarray analysis to determine which genes are expressed and which genes are not expressed.

Example 9

Organoids from human liver cultured using the EM1, EM2 and DM media of the invention and human liver were analysed using oligonucleotide microarray analysis to determine which genes are expressed and which genes are not expressed. A significantly different gene expression profile was noticeable between the genes expressed in expansion media, the genes expressed in differentiation medium and the genes expressed in adult liver. The trend for hepatocyte gene expression is roughly the same as for in the mouse but the differentiation of the organoids was less than in the mouse liver organoids. This may be due to use of the human cell used.

As often happens in an analysis using an oligonucleotide microarray, Lgr5 and Tnfrsf19 were not detected. However, they were found to be present in organoids cultured in the expansion medium.

Materials & Methods (for Examples 4 to 7)

Animal Treatment

Two-Eight month old Lgr5LacZ or Axin2-LacZ or WT littermates BL6/Balbc Flmice received an intraperitoneal injection of 0.8 ml/kg of CCL4 dissolved in corn oil (n=) or corn oil alone (n=). Mice were sacrificed 2 or 5 or 9 or 13 days later and the liver was isolated and further processed for RNA or bgalactosidase staining.

ß-Galactosidase (lacZ) Staining

Liver tissues were isolated and immediately incubated for 2 hours in a 20-fold volume of ice-cold fixative (1% Formaldehyde; 0.2% Gluteraldehyde; 0.02% NP40 in PBS0) at 4° C. on a rolling platform. The fixative was removed and the tissues washed twice in washing buffer (PBS0; 2 mM $MgCl_2$; 0.02% NP40; 0.1% NaDeoxycholate) for 20 minutes at room temperature on a rolling platform. The β-galactosidase substrate (5 mM $K3FE(CN)_6$; 5 mM $K4Fe(CN)_6 \cdot 3H_2O$; 2 mM $MgCl_2$; 0.02% NP40; 0.1% NaDeoxycholate; 1 mg/ml X-gal in PBS0) was then added and the tissues incubated in the dark at 37° C. for 2 h and overnight at room temperature. The substrate was removed and the tissues washed twice PBS0 for 20 minutes at room temperature on a rolling platform. The tissues were then fixed overnight in a 20-fold volume of 4% Paraformaldehyde (PFA) in PBS0 at 4° C. in the dark on a rolling platform. The PFA was removed and the tissues washed twice in PBS0 for 20 minutes at room temperature on a rolling platform.

The stained tissues were transferred to tissue cassettes and paraffin blocks prepared using standard methods. Tissue sections (4 μM) were prepared and counterstained with neutral red.

R-Spondin1 Treatment

Axin2-lacZ mice aged 6-8 weeks were injected IP with 100 μg of purified human R-spondin1 and sacrificed 48 hours later for LacZ expression analysis in the liver.

RT-PCR

RNA was extracted from gastric cell cultures or freshly isolated tissue using the RNeasy Mini RNA Extraction Kit (Qiagen) and reverse-transcribed using Moloney Murine Leukemia Virus reverse transcriptase (Promega). cDNA was amplified in a thermal cycler (GeneAmp PCR System 9700; Applied Biosystems, London, UK) as previously described (Huch et al., 2009). Primers used are shown in Table 3 below.

TABLE 3

Primers for RT-PCR

| Gene name | Gene Symbol | Sequence | PCR product (bp) |
|---|---|---|---|
| cytochrome P450, family 3, subfamily a, polypeptide 11 | CYP3A11 | fw TGGTCAAACGCCTCTC CTTGCTG<br>rv ACTGGGCCAAAATCCC GCCG | 100 |
| Glucose-6-phoshatase | G6P | fw GAATTACCAAGACTCC AGG<br>rv TGAGACAATACTTCCG GAGG | 581 |
| Keratin 19 | Krt19 | fw GTCCTACAGATTGACA ATGC<br>rv CACGCTCTGGATCTGT GACA | 549 |
| Albumin | Alb | fw GCGCAGATGACAGGGC GGAA<br>rv GTGCCGTAGCATGCGG GAGG | 358 |
| t-box 3 | Tbx3 | fw AGCGATCACGCAACGT GGCA<br>rv GGCTTCGCTGGGACAC TTAGATCT | 441 |
| Prospero-related-homeobox protein 1 | Prox1 | fw TTCAACAGATGCATTA CC<br>rv TCTTTGCCCGCGATGA TG | 270 |
| Fumarylacetoacetate-hydrolase | Fah | fw ACGACTGGAGCGCACG AGAC<br>rv AGGGCTGGCTGTGGCA GAGA | 183 |
| Tyrosine amino-transferase | Tat | fw TTTGGCAGTGGCTGAA AGGCA<br>rv GGGCCCAGGATCCGCT GACT | 258 |
| Tryptophan2,3-dioxygenase | Tdo2 | fw ACTCCCCGTAGAAGGC AGCGA<br>rv TCTTTCCAGCCATGCC TCCACT | 583 |

TABLE 3 -continued

Primers for RT-PCR

| Gene name | Gene Symbol | Sequence | PCR product (bp) |
|---|---|---|---|
| Leucine-rich repeat-containing G-protein coupled receptor 5 | Lgr5 | fw GGAAATGCTTTGACAC ACATTC<br>rv GGAAGTCATCAAGGTT ATTATAA | 413 |
| Transthyretin | TTR | fw ATGGTCAAAGTCCTGG ATGC<br>rv AATTCATGGAACGGGG AAAT | 220 |
| Glucokinase | Gck | fw AAGATCATTGGCGGAA AG<br>rv GAGTGCTCAGGATGTT AAG | 193 |
| hypoxanthine phosphoribosyl-transferase | Hprt | fw AAGCTTGCTGGTGAAA AGGA<br>rv TTGCGCTCATCTTAGG CTTT | 186 |

Imunohistochemistry

Immunostaining procedure used here was previously described in Huch et al. 2009. Briefly, five-micrometer sections were deparaffinized, rehydrated, and tissue sections were permeabilized using PBS-T (PBS; Tween20 0.1%). When required, sections were treated with 10 mMcitrate buffer (pH 6.0) for antigen retrieval, blocked using Universal blocking buffer (BioGenex)) and incubated with the primary antibody. Then, sections were washed twice with PBS and incubated with peroxidase conjugated secondary antibodies. DAB+(DAKO) was used as a chromogen substrate. Sections were counterstained with Mayer's hematoxylin and visualized on a Leica DMR microscope. The primary antibodies used were rabbit anti-Sox9 (1:600; 1 h at RT, Millipore), mouse anti-SMA (1:1000, overnight at 4° C., Sigma), rabbit anti-FAH (1:5000; overnight 37° C., gift from M. Grompe), rabbit anti-K19 (1:500; overnight 4° C., gift from M. Grompe). The peroxidase conjugated secondary antibodies used were Mouse or Rabbit Brightvision (Immunologic).

Immunofluorescence

For whole mount staining, organoids or isolated biliary ducts were fixed with acetone (organoids) or PFA4% (biliary ducts) for 30 min, washed once with PBS, permeabilized with PBS 0.3% Triton-X100 for 5 min, blocked using Universal blocking solution (Power block HK085-5KE BioGenex) and incubated overnight with the primary antibodies diluted in PBS1% FBS. Following several washes in PBS, samples were incubated with the secondary antibody. Nuclei were stained with Hoescht33342. Images were acquired using confocal microscopy (Leica, SP5). Three-dimensional reconstruction was performed using Volocity Software (Improvision). The primary antibodies used were rabbit anti-K19 (1:500; gift from M. Grompe), rat anti-hepatocyte surface marker (1:50, gift M. Grompe), goat anti-albumin (1:50, santa Cruz). The secondary antibodies used were all raised in donkey and conjugated to different Alexa fluorofores (donkey anti-goat 568, donkey anti rat-488, donkey anti rabbit-647, Molecular probes).

Flow Cytometry

Dissociated cells were resuspended at $1 \times 10^4$ cells per milliliter in 1 ml of DMEM+2% FBS prior to the addition of MIC1-1C3 hybridoma supernatant at a 1:20 dilution or OC2-2F8 hybridoma supernatant at a 1:50 dilution, and incubated for 30 min at 4° C. After a wash with cold Dulbecco's Phosphate Buffered Saline (DPBS), cells were resuspended in DMEM+2% FBS containing a 1:200 dilution of APC-conjugated goat anti-rat secondary antibody adsorbed against mouse serum proteins (Jackson Immunoresearch). Propidium iodide staining was used to label dead cells for exclusion. Cells were analyzed and sorted with a Cytopeia inFluxV-GS (Becton-Dickenson).

Transplantation Assay

The injection of sorted cell populations to the spleen and the withdrawal of NTBC to induce hepatocyte selection were performed as described previously (Overturf et al. 1996). Drug withdrawal was done in periods of 3 wk, followed by readministration until normal weight was restored in the recipient animals.

The invention claimed is:

1. A method for differentiating liver epithelial stem cells, wherein the method comprises culturing the epithelial stem cells in the presence of a culture medium comprising a basal medium for animal or human cells, and further comprising a ligand of an Epidermal Growth Factor (EGF) receptor, a Notch inhibitor, and a Transforming Growth Factor (TGF)-beta inhibitor.

2. The method according to claim 1, wherein the culture medium further comprises an FGF and/or HGF.

3. The method according to claim 1, wherein the ligand of an EGF receptor is EGF.

4. The method according to claim 1, wherein the Notch inhibitor is selected from:
 a. a gamma-secretase inhibitor;
 b. an inhibitor capable of diminishing ligand mediated activation of Notch; and
 c. an inhibitor of A Disintegrin And Metalloproteinase (ADAM) proteases.

5. The method according to claim 4, wherein the gamma-secretase inhibitor is DAPT, dibenzazepine (DBZ), benzodiazepine (BZ), or LY-411575.

6. The method according to claim 4, wherein the Notch inhibitor is tert-Butyl (2S)-2-[[(2S)-2-[[2-(3,5-difluorophenyl)acetyl]amino]propanoyl]amino]-2-phenylacetate (DAPT).

7. The method according to claim 1, wherein the TGF-beta inhibitor is an inhibitor of Activin Receptor-like Kinase 5 (ALK5), Activin Receptor-like Kinase 4 (ALK4), and/or Activin Receptor-like Kinase 7 (ALK7) signaling.

8. The method according to claim 7, wherein the TGF-beta inhibitor is selected from A83-01, SB-431542, SB-505124, SB-525334, SD-208, LY-36494, SJN-2511.

9. The method according to claim 8, wherein the TGF-beta inhibitor is A83-01.

10. The method according to claim 1, wherein the culture medium further comprises dexamethasone.

11. The method according to claim 10, wherein the dexamethasone is at a concentration of between 10 μM and 1 mM.

12. The method according to claim 1, wherein: the ligand of an EGF receptor is EGF at a concentration of about 50 ng/ml; the TGF-beta inhibitor is A83-01 at a concentration of about 500 nM; and/or the Notch inhibitor is DAPT at a concentration of about 10 μM.

13. The method according to claim 1, wherein the basal medium for animal or human cells is selected from Dulbecco's Modified Eagle Media (DMEM), Minimal Essential Medium (MEM), Knockout-DMEM (KO-DMEM), Glasgow Minimal Essential Medium (G-MEM), Basal Medium Eagle (BME), DMEM/Ham's F12, Advanced DMEM/Ham's F12, Iscove's Modified Dulbecco's Media and Minimal Essential Media (MEM), Ham's F-10, Ham's F-12, Medium 199, and RPMI 1640 Media.

14. The method according to claim 13, wherein the basal medium for animal or human cells comprises Advanced-DMEM/F12, and optionally further comprises gastrin, N-acetylcystein and/or B27.

15. The method according to claim 1, wherein the culture medium does not comprise one or more of the components selected from the list: a Wnt agonist, nicotinamide, and a BMP inhibitor.

16. The method according to claim 1, wherein the method further comprises contacting the cells with an extracellular matrix.

17. The method according to claim 16, wherein the extracellular matrix is a basement membrane preparations from Engelbreth-Holm-Swarm mouse sarcoma cells, or wherein the extracellular matrix is a synthetic extracellular matrix material.

18. A method according to claim 1, wherein the liver epithelial stem cells:
  a. express Lgr5; and/or
  b. do not naturally express one or more of Cd11b, CD13, CD14, Alpha Fetoprotein (AFP), Pdx1, a Cytochrome P450 (CYP) member at a significant level.

19. A method according to claim 1, wherein the differentiated cells:
  a. express one or more of Cd11b, CD13, CD14, AFP, Pdx1, a CYP member at a significant level; and/or
  b. express one or more of Tyrosine Aminotransferase (TAT) and/or Albumin; and/or
  c. express K19 and/or Fumarylacetoacetate Hydrolase (FAH); and/or
  d. do not express Lgr5.

* * * * *

UNITED STATES PATENT AND TRADEMARK OFFICE
CERTIFICATE OF CORRECTION

PATENT NO. : 11,034,935 B2
APPLICATION NO. : 15/665363
DATED : June 15, 2021
INVENTOR(S) : Huch Ortega et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 91 days.

Signed and Sealed this
Tenth Day of January, 2023

Katherine Kelly Vidal
*Director of the United States Patent and Trademark Office*